United States Patent
Ehmke et al.

(10) Patent No.: US 12,201,332 B2
(45) Date of Patent: Jan. 21, 2025

(54) BONE PLATE WITH MOVABLE JOINT

(71) Applicant: Acumed LLC, Hillsboro, OR (US)

(72) Inventors: Larry W. Ehmke, Portland, OR (US);
Brian R. Conley, Portland, OR (US);
Andrew W. Seykora, Portland, OR (US); Gregory D. Hutton, Beaverton, OR (US)

(73) Assignee: Acumed LLC, Hillsboro, OR (US)

( * ) Notice: Subject to any disclaimer, the term of this patent is extended or adjusted under 35 U.S.C. 154(b) by 0 days.

(21) Appl. No.: 18/387,333

(22) Filed: Nov. 6, 2023

(65) Prior Publication Data

US 2024/0065738 A1 Feb. 29, 2024

Related U.S. Application Data

(60) Division of application No. 17/464,108, filed on Sep. 1, 2021, now Pat. No. 11,844,555, which is a continuation of application No. 16/140,362, filed on Sep. 24, 2018, now Pat. No. 11,123,116, which is a continuation-in-part of application No. 16/001,867, (Continued)

(51) Int. Cl.
| | |
|---|---|
| *A61B 17/80* | (2006.01) |
| *A61B 17/88* | (2006.01) |
| *A61B 17/00* | (2006.01) |
| *A61B 17/56* | (2006.01) |

(52) U.S. Cl.
CPC .......... *A61B 17/80* (2013.01); *A61B 17/8009* (2013.01); *A61B 17/8023* (2013.01); *A61B 17/8057* (2013.01); *A61B 17/8061* (2013.01); *A61B 17/8085* (2013.01); *A61B 17/8863* (2013.01); *A61B 2017/00526* (2013.01); *A61B 2017/567* (2013.01); *A61B 17/8004* (2013.01)

(58) Field of Classification Search
CPC . A61B 17/8023; A61B 17/80; A61B 17/8061; A61B 17/8004
See application file for complete search history.

(56) References Cited

U.S. PATENT DOCUMENTS

| | | | |
|---|---|---|---|
| 4,706,659 | A | 11/1987 | Matthews et al. |
| 6,238,396 | B1 | 5/2001 | Lombardo |
| (Continued) | | | |

FOREIGN PATENT DOCUMENTS

| | | |
|---|---|---|
| DE | 3840466 A1 | 6/1990 |
| EP | 2928389 A1 | 10/2015 |
| (Continued) | | |

OTHER PUBLICATIONS

Japanese Office Action corresponding to Japanese Application No. 2020-567006; report dated Dec. 24, 2021; (15 pages).

(Continued)

*Primary Examiner* — Olivia C Chang
(74) *Attorney, Agent, or Firm* — K&L Gates LLP

(57) ABSTRACT

System, including methods and devices, for fixing bone. The system may include a bone plate having two or more plate members connected to one another with one or more movable joints. Each joint may permit the orientation of the plate members to be adjusted relative to one another in a single plane or two or more nonparallel planes. The joint may have a movable configuration and a fixed configuration. Methods of creating the bone plate are also provided.

20 Claims, 30 Drawing Sheets

Related U.S. Application Data filed on Jun. 6, 2018, now Pat. No. 11,219,466, and a continuation-in-part of application No. 15/990,633, filed on May 26, 2018, now Pat. No. 10,610,368, and a continuation-in-part of application No. 15/216,646, filed on Jul. 21, 2016, now Pat. No. 10,080,596, and a continuation-in-part of application No. 14/792,522, filed on Jul. 6, 2015, now Pat. No. 10,159,515, and a continuation-in-part of application No. 14/746,722, filed on Jun. 22, 2015, now Pat. No. 10,117,685, said application No. 15/216,646 is a continuation-in-part of application No. 14/706,922, filed on May 7, 2015, now Pat. No. 9,526,542, and a continuation-in-part of application No. 14/566,350, filed on Dec. 10, 2014, now Pat. No. 9,433,451, which is a continuation-in-part of application No. 14/565,116, filed on Dec. 9, 2014, now Pat. No. 9,433,448, said application No. 15/216,646 is a continuation-in-part of application No. 14/565,105, filed on Dec. 9, 2014, now Pat. No. 9,463,055, and a continuation-in-part of application No. 14/565,116, filed on Dec. 9, 2014, now Pat. No. 9,433,448, said application No. 14/566,350 is a continuation-in-part of application No. 14/565,105, filed on Dec. 9, 2014, now Pat. No. 9,463,055.

(60) Provisional application No. 62/110,220, filed on Jan. 30, 2015, provisional application No. 62/020,691, filed on Jul. 3, 2014, provisional application No. 62/016,883, filed on Jun. 25, 2014, provisional application No. 61/989,662, filed on May 7, 2014, provisional application No. 61/914,180, filed on Dec. 10, 2013, provisional application No. 61/913,593, filed on Dec. 9, 2013, provisional application No. 61/913,611, filed on Dec. 9, 2013.

(56) References Cited

U.S. PATENT DOCUMENTS

| | | | |
|---|---|---|---|
| 8,025,681 B2 | 9/2011 | Colleran et al. | |
| 2007/0276392 A1 | 11/2007 | Beyar et al. | |
| 2009/0082813 A1* | 3/2009 | Long | A61B 17/80 606/151 |
| 2009/0275947 A1* | 11/2009 | Graham | A61B 17/8061 606/280 |
| 2011/0218534 A1 | 9/2011 | Prandi et al. | |
| 2013/0165935 A1 | 6/2013 | Griffiths et al. | |
| 2014/0081269 A1* | 3/2014 | Biedermann | A61B 17/80 606/71 |
| 2016/0095636 A1* | 4/2016 | Wiederkehr | A61B 17/8033 606/281 |

FOREIGN PATENT DOCUMENTS

| | | |
|---|---|---|
| JP | 2005152650 A | 6/2005 |
| JP | 2015536736 A | 12/2015 |

OTHER PUBLICATIONS

Extended European Search Report corresponding to related European Application No. 19814141.8, mailed May 20, 2022, 10 pages.

* cited by examiner

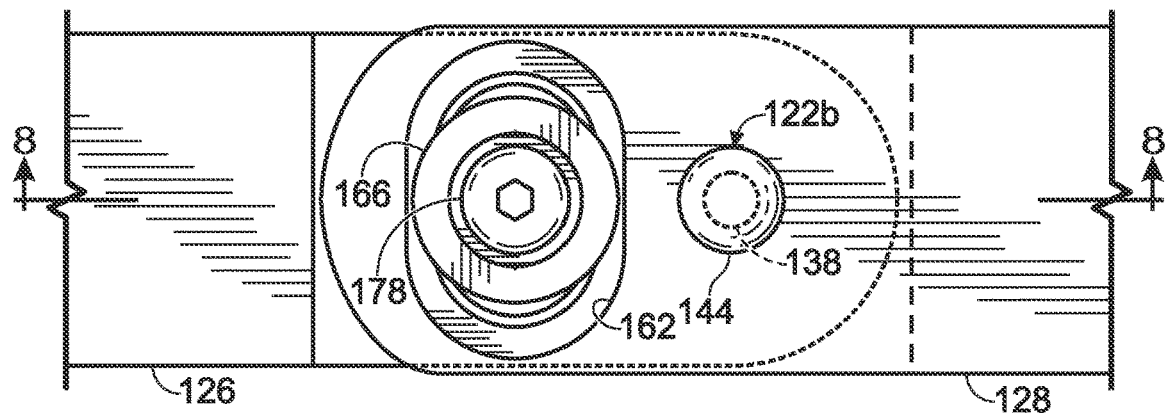
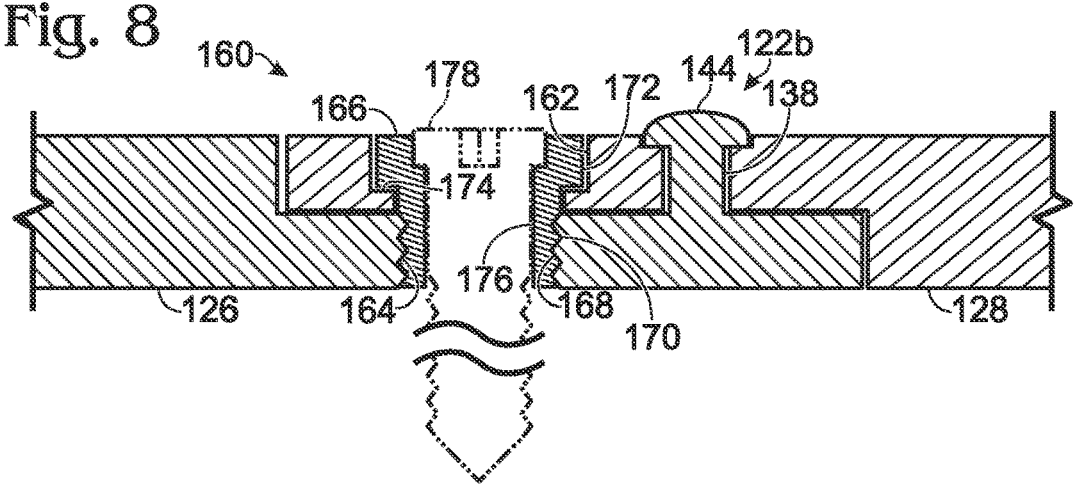
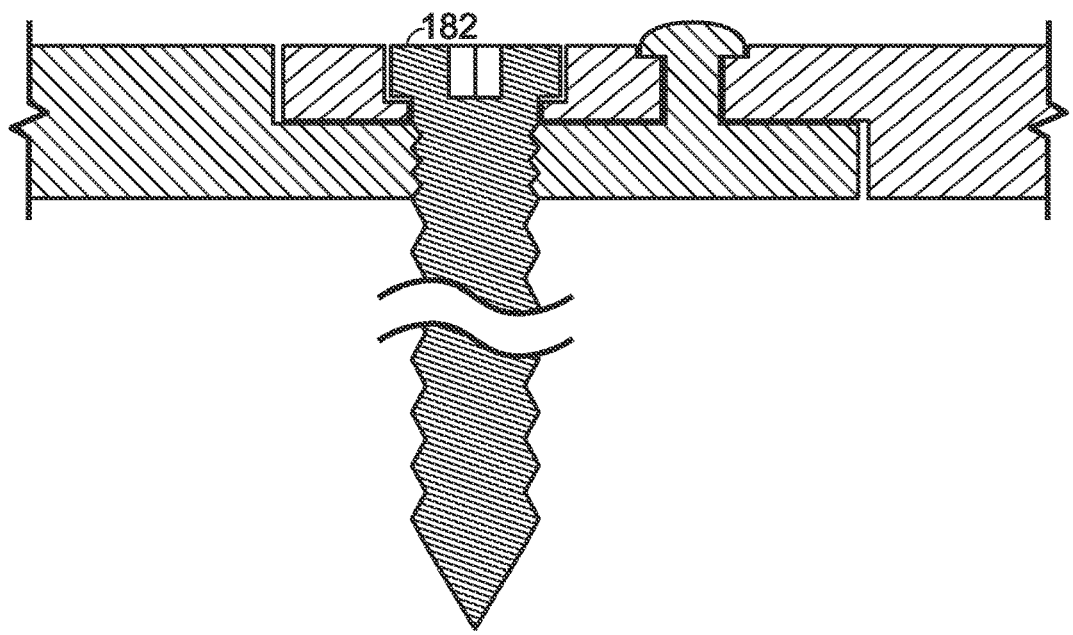

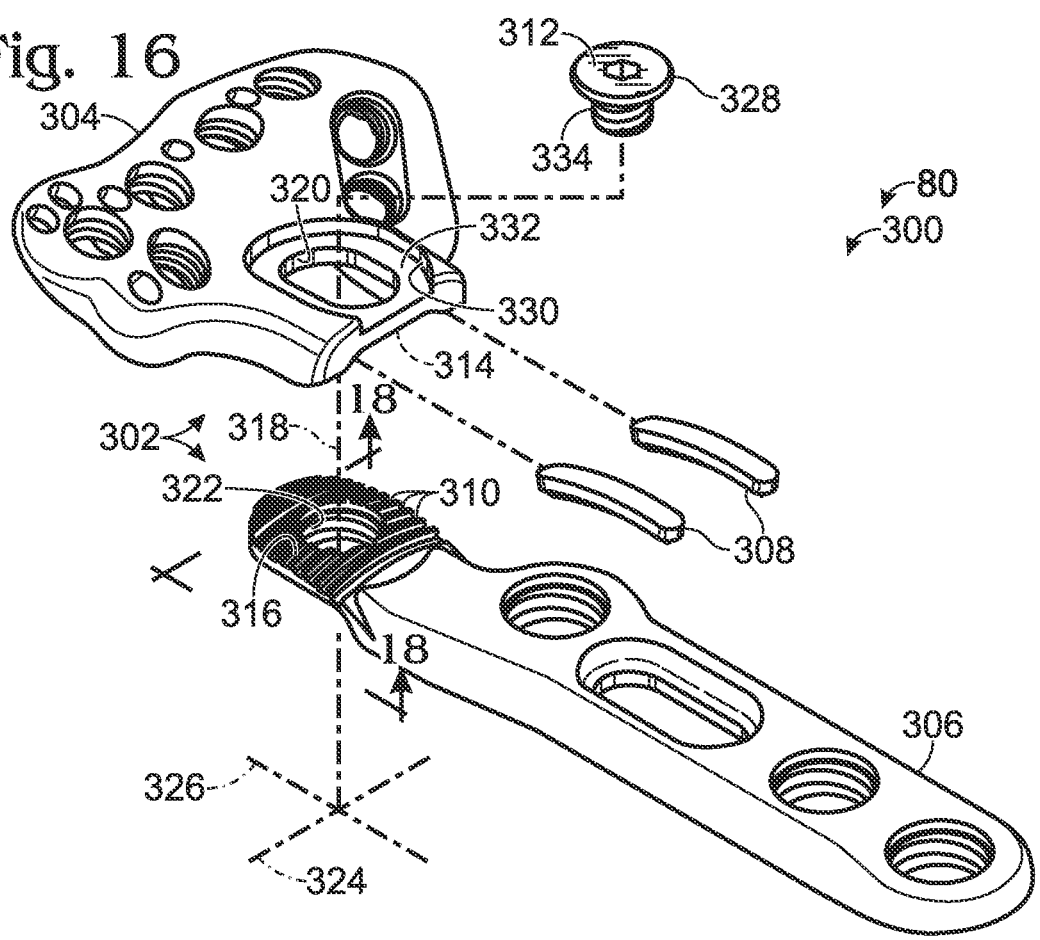

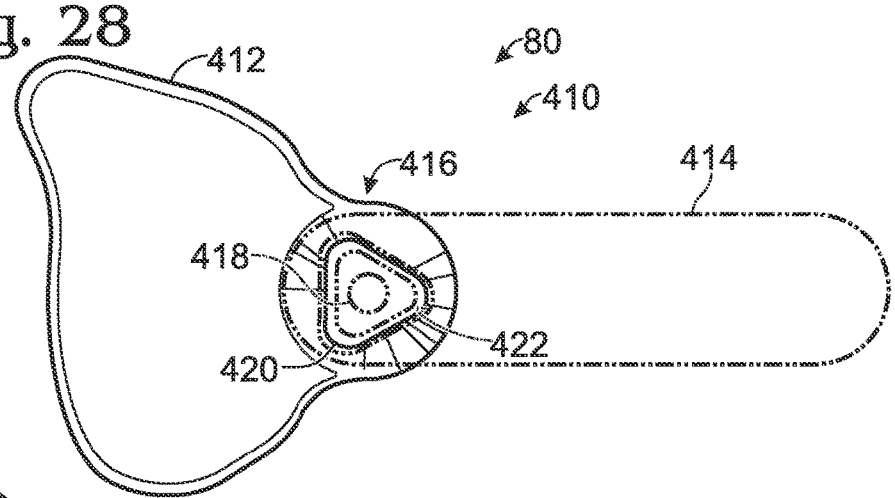
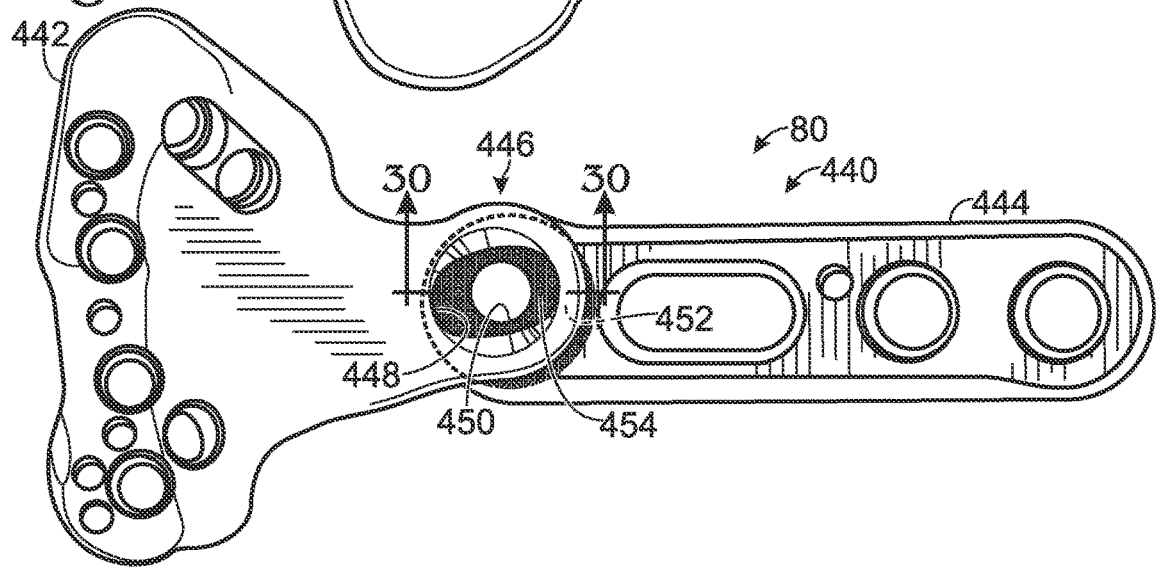
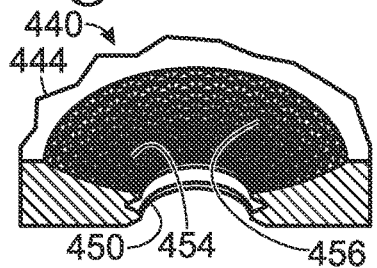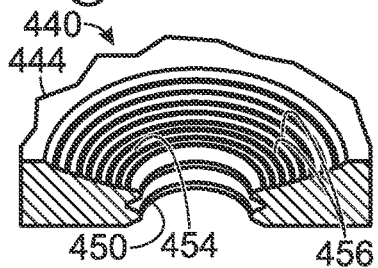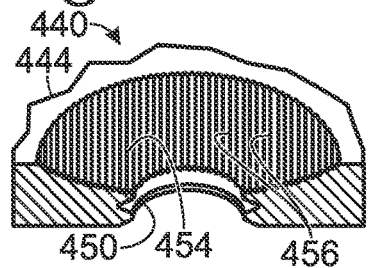
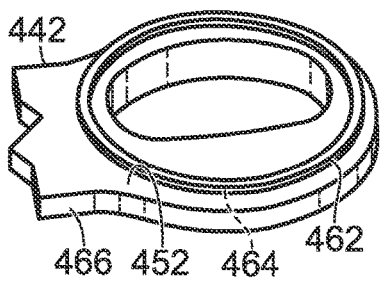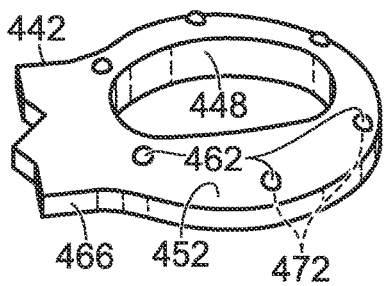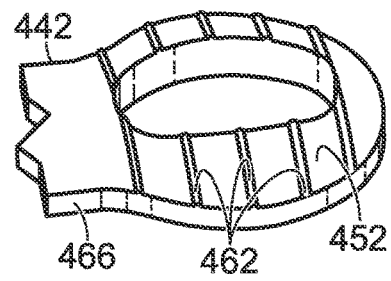

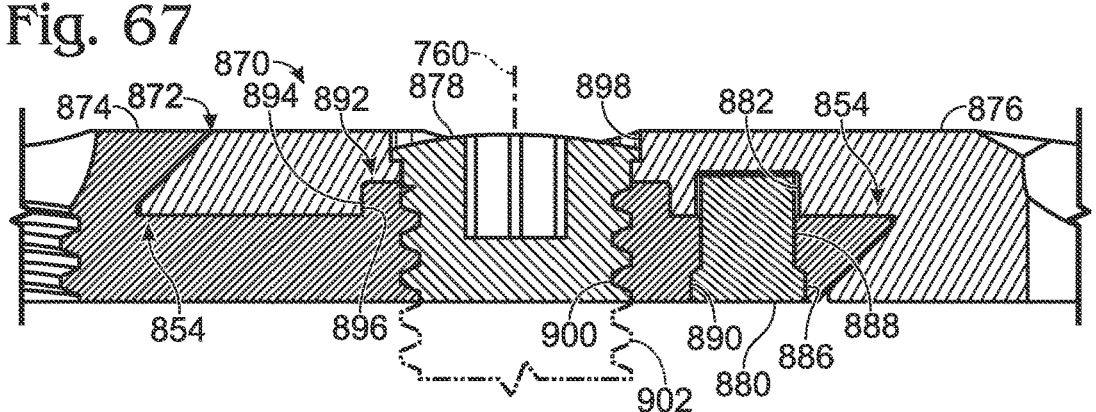
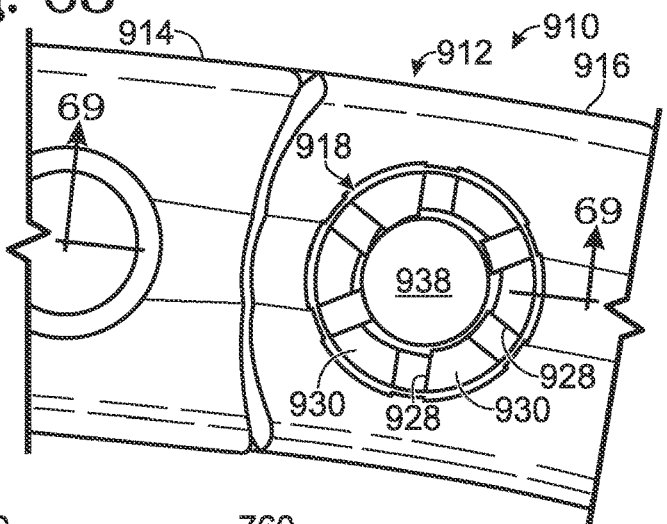
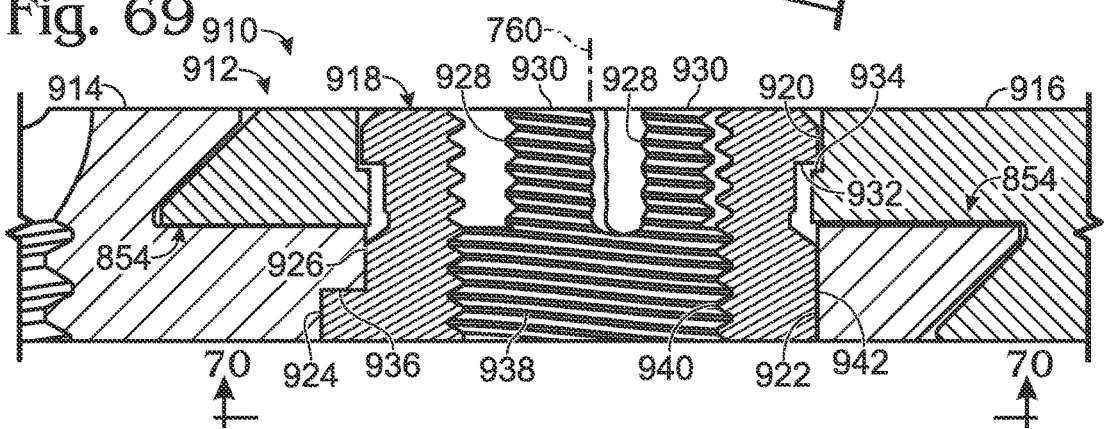
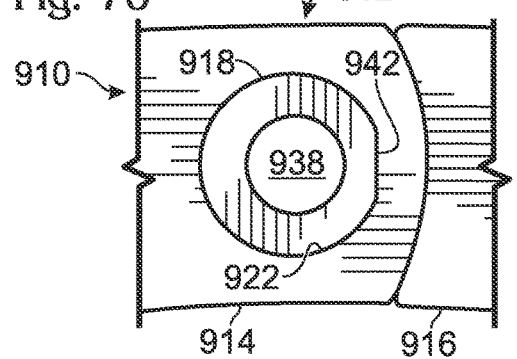

BONE PLATE WITH MOVABLE JOINT

CROSS-REFERENCES TO PRIORITY APPLICATIONS

This application is a divisional of U.S. patent application Ser. No. 17/464,108, filed Sep. 1, 2021, which is a continuation of U.S. patent application Ser. No. 16/140,362, filed Sep. 24, 2018, now U.S. Pat. No. 11,123,116, which is a continuation-in-part of the following U.S. patent applications: Ser. No. 14/746,722, filed Jun. 22, 2015, now U.S. Pat. No. 10,117,685; Ser. No. 14/792,522, filed Jul. 6, 2015, now U.S. Pat. No. 10,159,515; Ser. No. 15/216,646, filed Jul. 21, 2016, now U.S. Pat. No. 10,080,596; Ser. No. 15/990,633, filed May 26, 2018 now U.S. Pat. No. 10,610,368; and Ser. No. 16/001,867, filed Jun. 6, 2018, now U.S. Pat. No. 11,219,466.

Ser. No. 14/746,722, in turn, is based upon and claims the benefit under 35 U.S.C. § 119(e) of U.S. Provisional Patent Application Ser. No. 62/016,883, filed Jun. 25, 2014.

Ser. No. 14/792,522, in turn, is based upon and claims the benefit under 35 U.S.C. § 119(e) of U.S. Provisional Patent Application Ser. No. 62/020,691, filed Jul. 3, 2014; and U.S. Provisional Patent Application Ser. No. 62/110,220, filed Jan. 30, 2015.

Ser. No. 15/216,646, in turn, is a continuation-in-part of the following U.S. patent applications: U.S. patent application Ser. No. 14/565,105, filed Dec. 9, 2014, now U.S. Pat. No. 9,463,055; U.S. patent application Ser. No. 14/565,116, filed Dec. 9, 2014, now U.S. Pat. No. 9,433,448; U.S. patent application Ser. No. 14/566,350, filed Dec. 10, 2014, now U.S. Pat. No. 9,433,451; and U.S. patent application Ser. No. 14/706,922, filed May 7, 2015, now U.S. Pat. No. 9,526,542.

U.S. patent application Ser. No. 14/565,105, in turn, is based upon and claims the benefit under 35 U.S.C. § 119(e) of U.S. Provisional Patent Application Ser. No. 61/913,593, filed Dec. 9, 2013.

U.S. patent application Ser. No. 14/565,116, in turn, is based upon and claims the benefit under 35 U.S.C. § 119(e) of U.S. Provisional Patent Application Ser. No. 61/913,611, filed Dec. 9, 2013.

U.S. patent application Ser. No. 14/566,350, in turn, is a continuation-in-part of U.S. patent application Ser. No. 14/565,105, filed Dec. 9, 2014 and U.S. patent application Ser. No. 14/565,116, filed Dec. 9, 2014, with priority claims as listed above, and is based upon and claims the benefit under 35 U.S.C. § 119(e) of U.S. Provisional Patent Application Ser. No. 61/914,180, filed Dec. 10, 2013.

U.S. patent application Ser. No. 14/706,922, in turn, is based upon and claims the benefit under 35 U.S.C. § 119(e) of U.S. Provisional Patent Application Ser. No. 61/989,662, filed May 7, 2014.

Each of these priority applications is incorporated herein by reference in its entirety for all purposes.

INTRODUCTION

The human skeleton is composed of 206 individual bones that perform a variety of important functions, including support, movement, protection, storage of minerals, and formation of blood cells. These bones can be grouped into two categories, the axial skeleton and the appendicular skeleton. The axial skeleton consists of 80 bones that make up the body's center of gravity, and the appendicular skeleton consists of 126 bones that make up the body's appendages. The axial skeleton includes the skull, vertebral column, ribs, and sternum, among others, and the appendicular skeleton includes the long bones of the upper and lower limbs, and the clavicles and other bones that attach these long bones to the axial skeleton, among others.

To ensure that the skeleton retains its ability to perform its important functions, and to reduce pain and disfigurement, fractured bones should be repaired promptly and properly. Typically, fractured bones are treated using a fixation device that reinforces the bone and keeps bone fragments aligned during healing. Fixation devices may take a variety of forms, including casts for external fixation and bone plates for internal fixation, among others. Bone plates are implantable devices that can be mounted on bone with the plate spanning a fracture. To use a bone plate to repair a fractured bone, a surgeon (1) selects an appropriate plate, (2) reduces (sets) the fracture, and (3) attaches the plate to opposite sides of the fracture using suitable fasteners, such as bone screws, so that pieces of the bone are fixed relative to one another.

The bone plate often is formed integrally as one piece and then is bent intraoperatively by a surgeon to custom-fit the bone plate to a subject's bone. However, bending a unitary bone plate has various disadvantages. For example, bending can be time-consuming, can weaken the bone plate, may be difficult to control for small changes to the plate shape, and/or can be particularly challenging for in-plane deformation of the bone plate where the plate is generally most resistant to deformation.

Bone plates having two or more discrete plate segments connected to one another by at least one joint are known. These jointed bone plates solve various problems posed by one-piece bone plates. However, jointed bone plates need to be improved to compete effectively with the simplicity and familiarity of a unitary bone plate.

SUMMARY

The present disclosure provides a system, including methods and devices, for fixing bone. The system may include a bone plate having two or more plate members connected to one another with one or more movable joints. Each joint may permit the orientation of the plate members to be adjusted relative to one another in a single plane or two or more nonparallel planes. The joint may have a movable configuration and a fixed configuration. Methods of creating the bone plate are also provided.

BRIEF DESCRIPTION OF THE DRAWINGS

FIG. 7 is a fragmentary plan view of an exemplary bone plate having a hinge joint that is lockable with a locking member located at a position spaced from the pivot axis of the hinge joint, in accordance with aspects of the present disclosure.

FIG. 8 is a longitudinal sectional view of the bone plate of FIG. 7, taken generally along line 8-8 of FIG. 7 through the hinge joint and the locking member.

FIG. 9 a longitudinal sectional view taken as in FIG. 8 with the hinge joint locked with a different locking member.

FIG. 16 is an exploded view of another exemplary bone plate for fixation of the distal radius, with the bone plate having a multi-axis joint connecting a head to a shaft of the bone plate, and with the multi-axis joint having a pair of deformable elements and a set of teeth that deform the deformable elements as the joint is locked by manipulation of a connector.

FIG. 28 is a simplified plan view of yet another exemplary bone plate for fixation of the distal radius, with the bone plate having a multi-axis joint formed at an interface between a head plate member and a shaft plate member of the bone plate, and with the range of motion permitted by the joint governed by a triangular stop region, in accordance with aspects of the present disclosure.

FIG. 29 is a plan view of selected aspects of still another exemplary bone plate for fixation of the distal radius and having a multi-axis joint, taken in the absence of a connector for the joint, in accordance with aspects of the present disclosure.

FIG. 30 is a fragmentary sectional view of a shaft plate member of the bone plate of FIG. 29, taken generally along line 30-30 around the multi-axis joint and illustrating an exemplary pattern created by voids formed in a surface of the joint.

FIG. 31 is a fragmentary sectional view of another exemplary shaft plate member for the bone plate of FIG. 29, taken generally as in FIG. 30 and illustrating another exemplary pattern created by voids formed in a surface of the joint.

FIG. 32 is a fragmentary sectional view of yet another exemplary shaft plate member for the bone plate of FIG. 29, taken generally as in FIG. 31 and illustrating yet another exemplary pattern created by voids formed in a surface of the joint.

FIG. 33 is a fragmentary sectional view of a head plate member of the bone plate of FIG. 29, taken generally around the multi-axis joint with the head plate member generally inverted with respect to FIG. 29 and illustrating an exemplary joint surface including a protrusion for contact with any of the joint surfaces of FIGS. 30-32.

FIGS. 34 and 35 are fragmentary sectional views of other exemplary head plate members for the bone plate of FIG. 29, taken as in FIG. 33 and illustrating other exemplary joint surfaces including a protrusion for contact with any of the joint surfaces of FIGS. 30-32.

FIG. 67 is a fragmentary sectional view of the bone plate of FIG. 66, taken generally along line 67-67 of FIG. 66 through the joint after installation of a connector in a pair of aligned apertures defined by the plate members, in accordance with aspects of the present disclosure.

FIG. 68 is fragmentary plan view of an exemplary bone plate having an open hinge joint in which a connector having flexible locking tabs is held in place by a snap-fit attachment, in accordance with aspects of the present disclosure.

FIG. 69 is fragmentary sectional view of the bone plate of FIG. 68, taken generally along line 69-69 of FIG. 68.

FIG. 70 is a fragmentary, bottom view of the bone plate of FIG. 68, taken generally along line 70-70 of FIG. 69.

DETAILED DESCRIPTION

Figure 1:
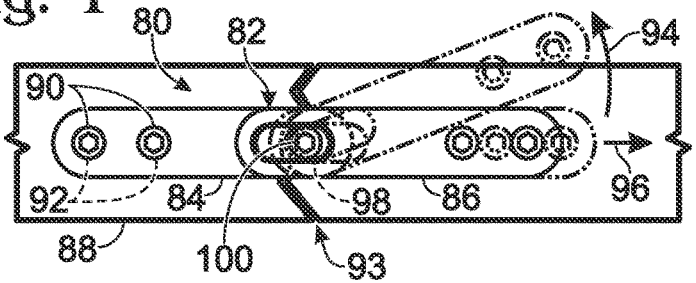
FIG. 1 is a schematic view of an exemplary bone plate having a movable joint connecting a pair of plate members and attached to a broken bone, and illustrating exemplary plate member movements permitted by a joint of the present disclosure.

The present disclosure provides a system, including methods and devices, for fixing bone. The system may include a bone plate having two or more plate members connected to one another with one or more movable joints. Each joint may permit the orientation of the plate members to be adjusted relative to one another in a single plane or two or more nonparallel planes. The joint may have a movable configuration and a fixed configuration. Methods of creating the bone plate are also provided.

Each joint may permit in-plane motion and/or out-of-plane motion (e.g., bending and/or twisting) of a pair of plate members connected to each other at the joint. The joint also or alternatively may permit adjustment of the length of the bone plate, via displacement of the plate members relative to one another at the joint. Each joint may or may not be lockable to create a rigid coupling of the plate members to one another (a fixed configuration), such as by compression applied at the joint with a discrete connector and/or via installation/adjustment of one or more fasteners disposed at one or more positions spaced from the joint.

In some embodiments, each joint may be a hinge joint. The hinge joint may be bracketed by a pair of locking through-holes configured to receive locking bone screws, with the bone plate optionally including at least two hinge joints and/or marked to indicate an axial zone for overlap with a fracture.

An exemplary bone plate is provided. The bone plate may include a pair of plate members connected to one another by a hinge joint defining a pivot axis. The plate members may be rotatable relative to one another in-plane about the pivot axis. The plate members may or may not be permanently connected to one another. In some embodiments, one of the plate members has an integrally-formed axle disposed in an aperture of the other plate member to create the hinge joint. The axle may be captured in the aperture, to permanently connect the plate members, by deforming the axle to create a retainer, or by welding a retainer to the axle, among others. The hinge joint may not be adjustable off-bone between movable and fixed configurations, and may require at least one tool for applying torque to rotate the plate members. In some embodiments, the bone plate may define a through-hole that is coaxial with the pivot axis and configured to receive a fastener that attaches the hinge joint to bone. The through-hole may or may not have an internal thread. In some embodiments, a pin in a slot determines the permitted range of rotation of the plate members about the pivot axis. In some embodiments, the plate members may have complementary features that create an interface. Portions of one of the plate members may be located directly under and directly over a portion of the other plate member at the interface, along a line parallel to the pivot axis, which may increase the bending strength of the bone plate at the hinge joint. In some embodiments, the plate members may be connected to one another with a discrete connector. The connector may be in threaded engagement with one of the plate members and may be manipulated to change the hinge joint between movable and fixed configurations. The connector may have a head under a shaft, and may have a left-handed external thread. Removal of the connector may be obstructed by a flange of one of the plate members, to permanently connect the plate members to one another. In some embodiments, the connector may have a snap-fit attachment to the plate members. A locking member may be receiving in an opening of the connector, and adjusted to radially expand a region of the connector to place the hinge joint in a fixed configuration.

In some embodiments, the bone plate may include a multi-axis joint having joint surfaces formed by a pair of plate members. At least one of the plate members may include a body and a discrete deformable element. The deformable element may form at least part of one joint surface. The deformable element may be deformed by contact with the other joint surface, when the joint is placed in a fixed configuration. In some embodiments, the deformable element may extend into a void defined by the other joint surface, before and/or after the joint is placed in a fixed configuration. In some embodiments, a protrusion defined by the other joint surface may deform the deformable element when the joint is placed in a fixed configuration.

In some embodiments, the bone plate may include a multi-axis joint having joint surfaces formed by a first plate member and a second plate member. The joint surface of the first plate member may include a protrusion, and the joint surface of the second plate member may define one or more voids. Each protrusion may deform and/or be deformed by the joint surface of the second plate member when the joint is placed in a fixed configuration, such that the protrusion extends into or more deeply into at least one void.

In some embodiments, the bone plate may include a multi-axis joint connecting a pair of plate members. The joint may have a movable configuration that allows an orientation of the plate members to be continuously adjusted in a first plane and discretely adjusted in a second plane that is transverse (e.g., orthogonal) to the first plane. The joint may include complementary, spherical surface regions and a ratchet. The ratchet may or may not selectively restrict rotation in one of two opposite rotational directions in the second plane. One of the plate members may form a tab. Movement of the tab may be stopped by contact with the other plate member to define a range of permitted rotation in the first plane. Alternatively, or in addition, the tab may be visible from above the bone plate and may be an indicator of the orientation of the plate members in the first plane.

In any embodiment of a bone plate having a multi-axis joint, the joint may have a limited range of motion, which may be determined by a projection of one plate member extending into an aperture defined by another plate member. The aperture also may receive part of a connector that connects the plate members to one another.

In any embodiment of a bone plate having a multi-axis joint, the bone plate may include a connector that connects the plate members to one another. The connector may have a head under a shaft. The connector may include an external, left-handed thread. The shaft may form a driver interface for a suitable driver to adjust the connector from above the bone plate.

Further aspects of the fixation systems are described in the following sections: (I) overview of bone plates with movable joints, (II) bone plates with single-axis joints, (III) bone plates with multi-axis joints, (IV) bone plates with single joints for out-of-plane angular adjustment, (V) bone plates with joints to adjust translational offset, (VI) methods of bone fixation, and (VII) examples.

I. OVERVIEW OF BONE PLATES WITH MOVABLE JOINTS

This section provides an overview of bone plates with movable joints; see FIG. 1.

FIG. 1 shows a schematic view of an exemplary bone plate 80 having a movable joint 82 (also called a movable connection) connecting a pair of plate members 84, 86. Each plate member may be mounted (e.g., separately mounted) to a bone 88 using one or more fasteners 90 (such as screws, pins, wires, rivets, etc.). Each fastener may be received in a through-hole (interchangeably termed an opening) defined by the plate member, and extends into the bone. (The plate member interchangeably may be called a plate, a plate piece, or a mounting member.) Bone 88 may have at least one discontinuity, such as a fracture 93 or cut, spanned by the bone plate. Joint 82 may overlap the discontinuity, as shown here, or may be offset along the bone from the discontinuity. Bone plate 80 interchangeably may be termed a fixation device or a bone plate assembly.

Exemplary relative movements of plate members 84, 86 that may be permitted by movable joint 82 are illustrated in phantom and identified by motion arrows 94, 96. The plate members may be movable relative to one another in at least one plane and/or about at least one rotation axis, indicated by a rotation arrow 94, to change the angular orientation of the plate members relative to one another. Rotation may be in-plane or out-of-plane with respect to a plane defined by the bone plate, and may be about a long axis of the bone plate and/or plate member or about another axis. The plate members also or alternatively may be adjustable relative to one another along at least one displacement axis, indicated by a displacement arrow 96. The displacement axis may or may not be linear, to provide net translational displacement without or with rotation of the plate members relative to one another.

Rotation or movement of plate members relative to one another that is "in-plane" occurs in a plane that is at least generally parallel to a plane defined by one or more of the plate members. The in-plane movement may, for example, be within about 20, 10, 5, 2, or 1 degree(s) of perfectly parallel to the plane defined by the one or more of the plate members. Single-axis joints (e.g., hinge joints) and multi-axis joints may permit in-plane rotation.

Each rotation axis (and/or plane in which rotation occurs) may have any suitable position and orientation with respect to the bone plate. The rotation axis may be fixed or variable with respect to one or both plate members. If variable, the position of the rotation axis may change before or during rotation of the plate members to change their angular orientation. The rotation axis may or may not pass through bone plate 80 and/or joint 82. Whether or not the rotation axis passes through the bone plate or joint, the rotation axis may have any suitable relationship to a plane (e.g., a length-width plane) and/or a long axis defined by the bone plate and/or at least one plate member. The rotation axis may be transverse (e.g., substantially or at least generally perpendicular), or substantially or at least generally parallel to the plane or long axis. For example, the rotation axis may be within about 20, 10, 5, 2, or 1 degree(s) of perfectly parallel or perfectly perpendicular.

Each translational displacement axis may have any suitable orientation with respect to the bone plate. The displacement axis may be at least generally or substantially parallel, transverse (e.g., perpendicular), or oblique to the plane and/or long axis defined by the bone plate and/or at least one plate member. Accordingly, net movement of the plate members relative to one another parallel to the displacement axis may change a longitudinal offset and/or a transverse offset of the plate members relative to one another. Both offsets can be changed at the same time if the displacement axis is oblique to each of the characteristic orthogonal axes defined by the bone plate or a plate member thereof. In any event, the transverse offset may be adjustable in a plane at least generally or substantially parallel to a plane defined by the bone plate and/or at least one plate member, and/or in a plane that is oblique or at least generally or substantially perpendicular to the plane defined by the bone plate.

The bone plate may have any suitable number of plate members, and number and position(s) of movable joints connecting the plate members to one another (e.g., connecting the plate members end-to-end). For example, the bone plate may have 2, 3, 4, or more plate members and/or 1, 2, 3, or more movable joints. In some embodiments, the bone plate may have N plate members and N−1 movable joints. If the bone plate has more than one movable joint, the joints may have any suitable position relative to one another, such as spaced along the long axis of the bone plate from one another, or spaced obliquely or perpendicular to the long axis. Each movable joint may be located at any suitable position with respect to a pair of plate members that are connected to one another by the joint. The joint may be located near the end of each of the plate members or may be spaced substantially from the opposite ends of at least one of the plate members.

The plate members may or may not be permanently connected to one another at a movable joint. A permanent connection between plate members may be created during manufacture of a bone plate, such that the plate members always remain connected to one another during normal handling and installation. Plate members that are permanently connected to one another are designed never to be accidentally disassembled by a user. The plate members cannot be completely separated from one another without damaging the bone plate (e.g., by cutting, breaking, plastically deforming, melting, or the like, a region of the bone plate), or without the use of one or more tools unrelated to installation or adjustment of the bone plate. A bone plate with plate members that are permanently connected to one another at a hinge joint offers the advantage of a hinged bone plate without the risk of dropping or losing a piece of the hinge joint (e.g., a connector) during surgery.

Each plate member may have any suitable structure. The plate member may or may not be elongate. The plate member may have an outer surface (interchangeably termed an outer side or top side) opposite an inner surface (interchangeably termed an inner side or bottom side). The plate members collectively may form an outer surface (interchangeably termed a top surface) and an inner surface (interchangeably termed a bottom surface) of the bone plate. The inner surface and the outer surface of the bone plate (and each plate member) respectively face toward and away from a bone when the bone plate is attached to the bone. The inner surface may be configured to contact bone. Each plate member may be one piece, with no parts that move relative to one another without deformation of the plate member. The one-piece plate member may be formed integrally, such that the entire plate member is continuous (monolithic). The plate member has a length, a width, and a thickness, where the thickness is less than the length and width, such as less than 50%, 20%, or 10% of the length and/or width. The length is generally greater than the width, but in some embodiments the length and width may be equal.

Each plate member may define at least one opening 92 having any suitable structure and position. Each opening 92 may be a through-hole (interchangeably termed an aperture) that extends through the plate member from the outer surface to the inner surface thereof. The through-hole may have a closed perimeter (completely bounded circumferentially) or an open perimeter. The through-hole or other opening may define an axis that is substantially perpendicular or oblique to the plane of the plate member. Each through-hole or other opening may or may not be elongated in the plane of the plate member. Accordingly, the through-hole may or may not be circular. The through-hole or other opening may or may not have attachment structure formed by a wall thereof that allows a fastener, such as an externally threaded fastener, to be attached to the plate member at the through-hole. The attachment structure may, for example, be an internal thread or at least one linear lip.

The plate member may have any suitable number of openings 92. If the plate member has two or more openings, the openings may be distributed in a direction along and/or across the bone plate from one another.

Each movable joint 82 may have any suitable structure. The joint may be formed at a region of overlap of a pair of the plate members, where the plate members overlap one another and respective joint surfaces of the plate members face and contact one another. The joint surfaces may be at least generally complementary to one another, with one joint surface being concave and the other joint surface convex. In some embodiments, one or more both joint surfaces may include surface features that improve the stability of the locked joint by resisting slippage of the joint surfaces relative to one another. The surface features may include one or more protrusions and/or one more voids, each of which may or may not be deformable. In some embodiments, the surface features may include a uniform array of projections and/or recesses, such as a set of teeth defined by one or both joint surfaces. In some embodiments, the surface features of one joint surface may be complementary to one or more of the surface features of the other joint surface, such that the joint surfaces can be mated with one another to resist slippage. In some embodiments, the joint surfaces can be mated in a plurality of discrete registers that are offset from one another by the spacing of the surface features of at least one of the joint surfaces. For example, one of the joint surfaces may define a plurality of teeth and the other joint surface may form at least one tooth. The teeth of the one joint surface can mate with the at least one tooth of the other joint surface in a plurality of different and discrete registers. Each of the teeth may be symmetrical or asymmetrical in cross section. If symmetrical, the teeth may permit movement of the joint surfaces relative to one another in both opposite rotational or translational displacement directions of the joint. If asymmetrical, the teeth of the joint surfaces may collectively form a ratchet that selectively permits movement of the joint surfaces in only one of two opposite rotational or displacement directions of the joint. In some embodiments, the joint surfaces may define surface features that are not complementary to each other, and the surface features may deform, particularly when the joint is compressed.

One of both joint surfaces of a joint may be formed at least partially by a one-piece body of one of the plate members. The body also may define one or more through-holes to receive fasteners. In some embodiments, a joint surface may be formed by the body of one of the plate members and at least one deformable element 98 (also called an anti-slip element) associated with the body. The deformable element may be softer than the body of both plate members and may be deformed selectively by contact with the other joint surface. For example, the deformable element may be formed of polymer and each body of metal, or the deformable element may be formed of a softer metal and each body of a harder metal, among others. In any event, the deformable element may deform when the joint is compressed, to resist slippage of the plate members relative to one another. Surface features of at least one of the joint surfaces may facilitate deformation of the deformable element. For example, one or more of the surface features (e.g., one or more ridges) may form or deepen one or more indentations in the deformable element when the joint is compressed. The deformable element may be disposed at least partially in a recess formed in one of the joint surfaces and may project out of the recess toward the other joint surface, for contact therewith. The deformable element may be an insert that is formed separately and then attached to one of the plate member bodies, or the deformable element may be formed in contact with one of the bodies, such as by overmolding or otherwise applying a material to the body to create the deformable element. The deformable element alternatively may be considered to be distinct from the plate member. Accordingly, the deformable element may be firmly attached to one of the plate members of a joint and movable with respect to the other plate member of the joint.

Bone plate 80 may include a discrete connector 100 that connects the plate members to one another at the joint. The connector may be described as a locking member (which may, in some embodiments, be described as a fastener and/or a lock screw) that controls whether joint 82 is in a movable configuration or a fixed (locked) configuration. The terms "movable" and "fixed" are relative terms. A fixed configuration requires substantially more force to produce movement of plate members relative to one another, such as at least about 5, 10, 25, 50, or 100 times as much force, among others. In the fixed configuration, the bone plate may become rigid at the joint, with the plate members rigidly coupled to one another, so that the bone plate can function like a traditional (non-jointed) bone plate. The connector may extend from one plate member to another plate member through the joint surfaces of the plate members. For example, the connector may define a pivot axis of the joint (i.e., may be coaxial to the pivot axis) or may be offset from the pivot axis. Each plate member may define an aperture to receive a portion of the connector. In some embodiments, the connector may have an external thread for attaching the connector to one of the plate members at an aperture thereof. The connector may be rotatable to adjust a compression of the plate members at the joint, thereby determining whether the joint is fixed or movable. In some indications, the joint may not lockable, for example, where the deforming forces act in a different plane than the adjustment capability, such as for clavicle fixation. Movement at the locked joint may be restricted by any suitable mechanism including any combination of friction, obstruction, interfitment, or the like.

II. BONE PLATES WITH SINGLE-AXIS JOINTS

This section describes exemplary bone plates with hinge joints that permit in-plane angular adjustment of plate members relative to one another; see FIGS. 2-14B (and also see Examples 1 and 3 of Section VII).

FIGS. 2-6 show an exemplary bone plate 120 having a pair of hinge joints 122a, 122b arranged along the long axis of the bone plate and permanently connecting plate members 124, 126, and 128 to one another. (Plate member 126 is a central plate member, and plate members 124 and 128 are end plate members.) Each hinge joint resists out-of-plane bending and torsional forces, while permitting movement, indicated at 130 in FIG. 2, about a single pivot axis arranged transverse (e.g., orthogonal) to a plane defined by the bone plate and/or at least one plate member of the hinge joint. This pivotal movement permits adjustment of the longitudinal shape of the bone plate by in-plane motion of the plate members, to allow a surgeon to customize the bone plate to the longitudinal shape of a subject's bone. In some embodiments, bone plate 120 may have only two plate members connected by a single hinge joint (or four or more plate members connected by three or more joints). Bone plate 120 may be used to fix a clavicle or any other suitable bone, such as a femur, tibia, fibula, radius, ulna, humerus, rib, or the like (also see Section VI).

Figure 2:
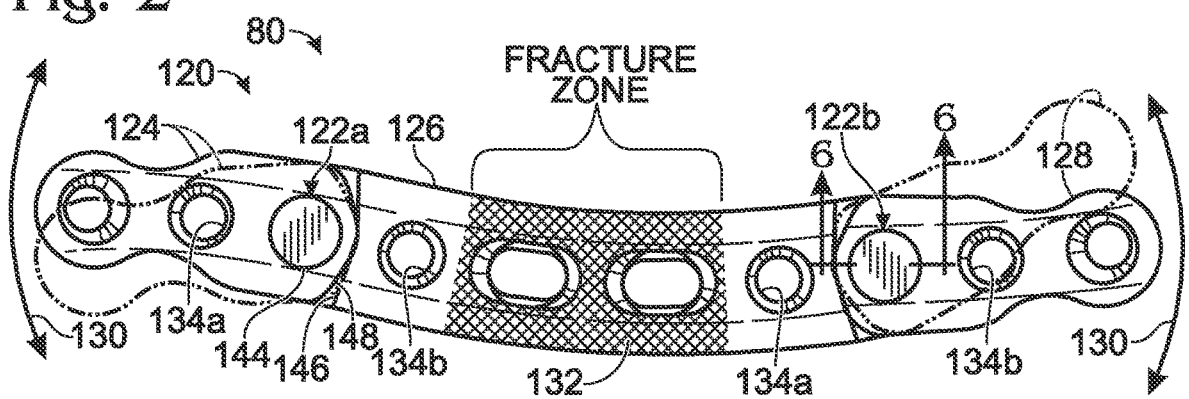
FIG. 2 is a plan view of an exemplary bone plate for fixation of a clavicle and having a pair of rotatable joints spaced along the bone plate from one another, with each joint being a hinge joint that is movable about a rotation axis arranged transverse to a plane defined by the bone plate, to allow adjustment of the longitudinal shape of the bone plate, in accordance with aspects of the present disclosure.
Figure 3:
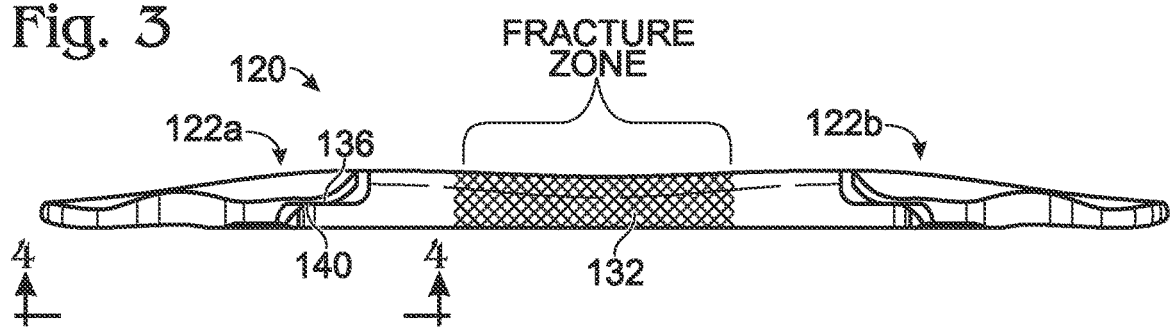
FIG. 3 is a lateral view of the bone plate of FIG. 2.
Figure 4:
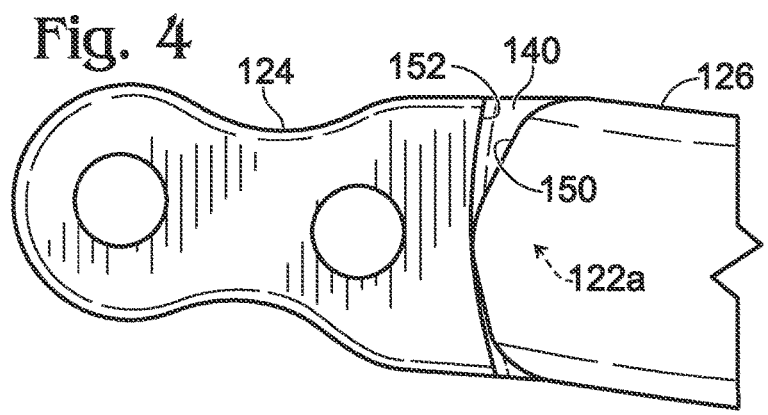
FIG. 4 is a bottom, fragmentary view of an end portion of the bone plate of FIG. 2, taken generally along line 4-4 of FIG. 3.
Figure 5:
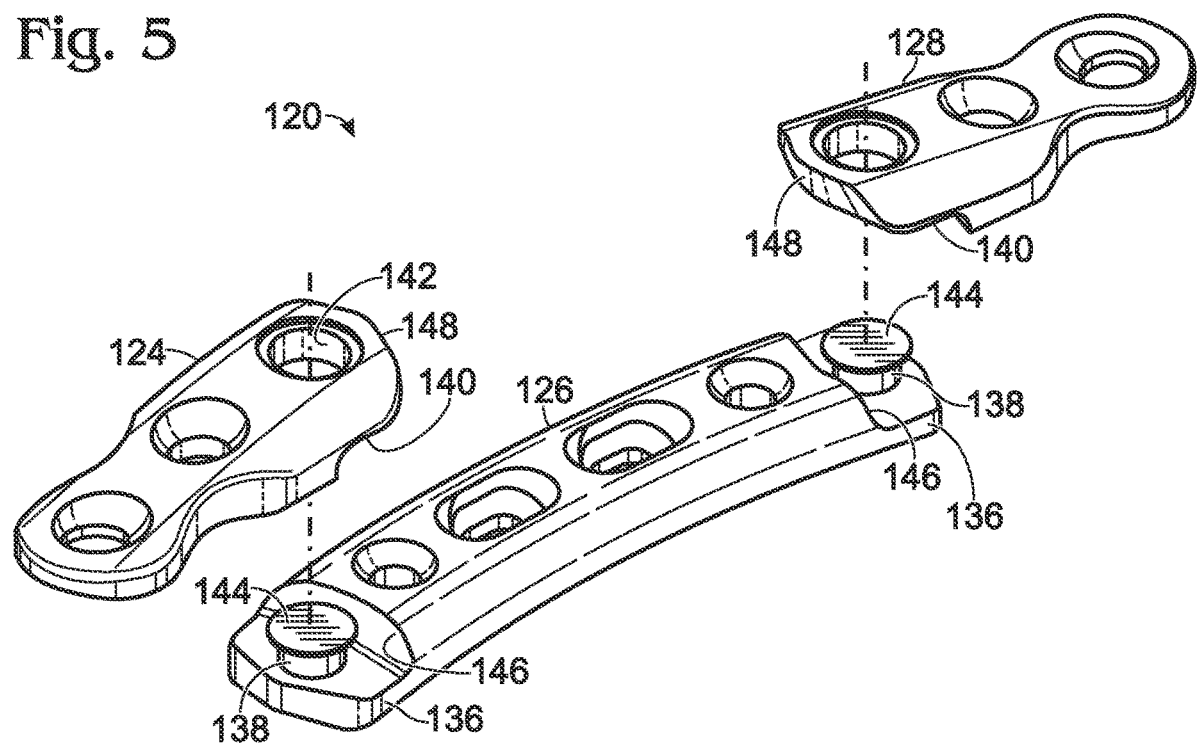
FIG. 5 is an exploded view of the bone plate of FIG. 2 showing the three segments (plate members) of the bone plate that are attached to one another by hinge joints.
Figure 6:
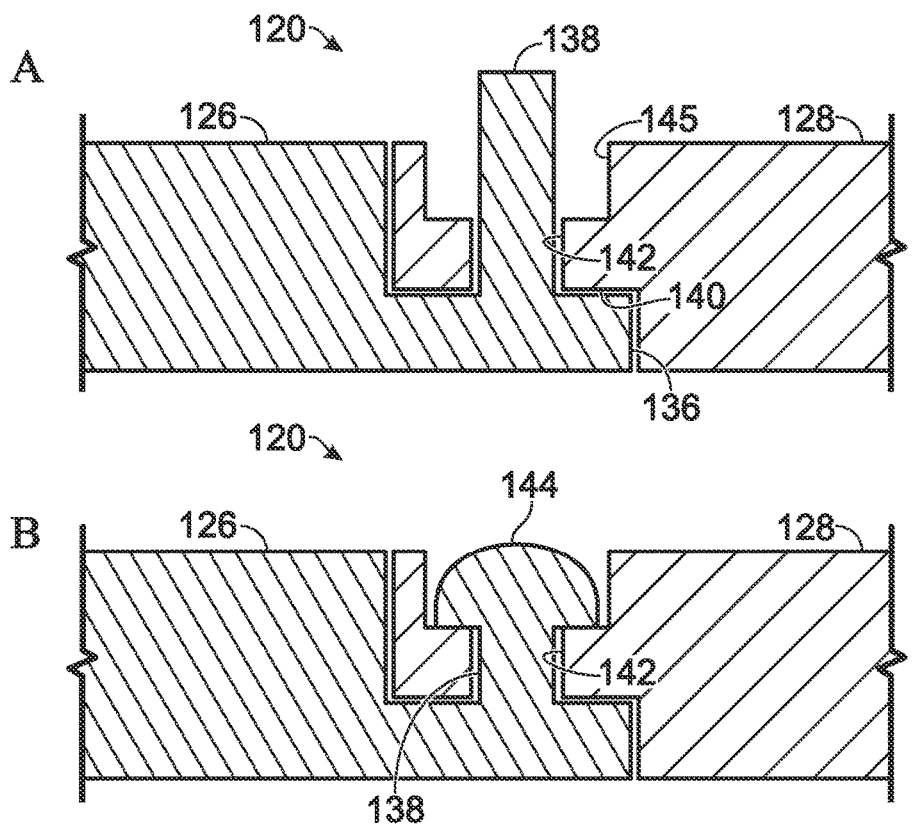
FIG. 6 is a schematic sectional view of the bone plate of FIG. 2, taken generally along line 6-6 of FIG. 2 through one of the hinge joints of the bone plate before (panel A) and after (panel B) an axle of the joint is deformed to capture another plate member of the bone plate on the axle, in accordance with aspects of the present disclosure.

Bone plate 120 may be marked with one or more surface markings 132, to define a longitudinal region of the bone plate that should overlie the fractured or cut portion of the bone to be fixed (the "fracture zone") (see FIGS. 2 and 3). The surface marking may be formed by etching, machining, molding, coating, electrolyzing, etc., the bone plate at the region to be marked, to make the region or boundaries thereof visibly distinguishable. In some embodiments, the marked region may have a different color than other parts of the bone plate. In any event, central plate member 126 may be positioned on a bone to longitudinally span the fractured or cut portion of the bone. However, in some embodiments, bone plate 120 can be positioned on a fractured bone with a fracture of the bone overlapping end plate member 124 or 128, one of the hinge joints 122a or 122b, and/or a region of central plate member 126 outside the marked region of the bone plate.

In the depicted embodiment, each hinge joint lacks the ability to be adjustably compressed along the pivot axis, to change the hinge joint between movable and fixed configurations. Instead, rotational movement at each joint may be restricted by securing the bone plate to an unbroken (continuous) portion of bone with a pair of fasteners placed into the unbroken portion on opposite sides of each hinge joint, such that the unbroken portion extends from one of the fasteners to the other fasteners of the pair. In some embodiments, the hinge joint may be located between a pair of through-holes 134a, 134b having attachment structure for the fasteners (such as an internal thread), to rigidly attach each fastener to the bone plate. In any event, bone plate 120 may permit at least two or three fasteners to be placed into unbroken bone on each side of the fracture zone.

The hinge joint may be formed as a movable, half lap joint; see FIGS. 3-6. Central plate member 126 may form a tab 136 of reduced thickness at each of its ends. An axle 138 (interchangeably termed a protrusion or a post) may project orthogonally from the tab. Each end plate member 124, 128 may define an undercut region 140 at one of its ends. The end plate member may define an aperture 142 sized to receive the axle (e.g., sized slightly larger in diameter than the axle), while undercut region 140 may be sized to receive tab 136 without increasing the thickness of the bone plate. The end of axle 138 may be deformed (e.g., swaged) (see panels A and B of FIG. 6) to form a retainer or head 144 that captures one of the end plate members on the axle, to prevent the plate members from being disconnected from one another without damaging the bone plate. Retainer 144 may occupy a widened region 145 of aperture 142. In some embodiments, the height of each of tab 136, aperture 142 excluding widened region 145, and widened region 145 may be about one-third of the overall height (thickness) of the bone plate at the hinge joint. Retainer 144 may protrude from the top surface of a plate member, or retainer 144 may be flush or recessed with respect to the top surface. In some examples, retainer 144 may be welded to the axle. In some examples, the entire bone plate (including the hinge joint) may be produced by 3D printing, optionally followed by deformation at the hinge joint (e.g., at the retainer) to increase the frictional resistance to rotation of the plate members. In some examples, retainer 144 may be formed by a discrete element, such as a nut attached to a threaded version of the axle, among others. In some examples, aspects of the hinge joint may be reversed. For example, central plate member 126 may form an undercut region that overlies a tab formed by an end plate member at the hinge joint, and/or an end plate member may provide the axle.

The axle may have any suitable properties. The axle may or may not be elongated along the pivot axis. The axle may be cylindrical or at least may have a cylindrical portion disposed in the aperture of the other plate member. The axle may have a through-hole that is pre-formed before the axle is placed into the aperture, or the through-hole may be formed after the retainer is created, among others. In some embodiments, the through-hole may be pre-formed and then modified after the retainer has been created. Modification of the through-hole may include creating an internal thread in the through-hole, and/or revising the through-hole to remove distortion, if any, produced when the retainer is created.

Each hinge joint 122a, 122b may have a frictional resistance that is not adjustable at the joint by the user (e.g., a surgeon). In other words, the hinge joints are not configured to be adjustable off bone between a movable configuration and a fixed configuration, as described in more detail below in Example 3 of Section VII. The frictional resistance may be set during manufacture of the bone plate by tightly engaging retainer 144 with one of the plate members, such as a wall region of aperture 142 and/or an outer surface of the plate member. A bone plate having a hinge joint that lacks distinct movable and fixed configurations (and, optionally, has no discrete connector) can make the bone plate easier and faster to install, less likely to experience a mechanical malfunction or failure (e.g., caused by a discrete connector becoming loose over time), and more resistant to accidental disassembly.

The range of motion at each hinge joint may be determined by contact between stop regions 146 and 148 (see FIGS. 2 and 5) and/or stop regions 150 and 152 (see FIG. 4), which may be formed by vertical walls of central plate member 126 and an end plate member 124 or 128. The hinge joint may have any suitable range of angular motion, such as at least about 5 or 10 degrees, and/or less than about 45, 30, or 20 degrees, among others.

FIGS. 7 and 8 show a bone plate 160 that is a version of bone plate 120 having a hinge joint 122b that can be locked off bone. Overlapped regions of central plate member 126 and end plate member 128 may define a pair of aligned apertures 162, 164 to receive a fastener that functions as a locking member 166. The locking member may be a set screw. Upper aperture 162 may be elongated transverse to the long axis of the bone plate (and elongated in the plane of the bone plate), to form a slot. Lower aperture 164 may have an internal thread 168. Locking member 166 may have an external thread 170 to attach the locking member to plate member 126 at lower aperture 164. A head 172 of the locking member may be disposed in a wider, top region of upper aperture 162 and moves along the long axis of upper aperture 162 as the plate members of the bone plate are pivoted relative to one another at hinge joint 122b. The underside of head 172 may be tightened against a wall region 174 of upper aperture 162, to urge plate member 128 into tight engagement with plate member 126, to fix the angular orientation of the plate members relative to each other at a selected rotational position. Locking member 166 may define a central through-hole 176 to receive a fastener, such as a bone screw 178, that extends into bone.

FIG. 9 shows bone plate 160 locked with a different locking member 182 that is not cannulated and is configured to extend below the bone plate into bone. In other embodiments, non-cannulated locking member 182 may not extend substantially below the inner surface of the bone plate.

Figure 10:
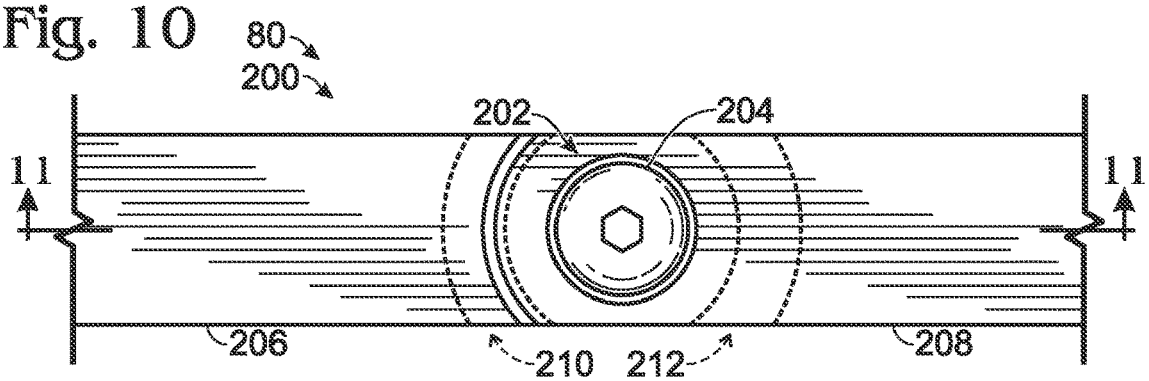
FIG. 10 is a fragmentary plan view of an exemplary bone plate having a hinge joint locked with a connector, with plate members of the bone plate fitted together via a pair of arcuate, complementary mating regions centered around and bracketing the pivot axis of the hinge joint.
Figure 11:
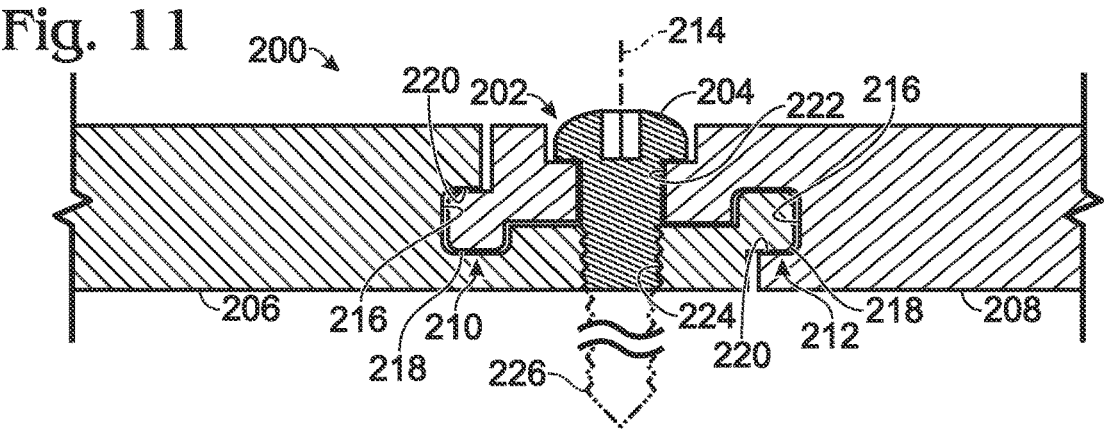
FIG. 11 is a longitudinal sectional view of the bone plate of FIG. 10, taken generally along line 11-11 of FIG. 10.

FIGS. 10 and 11 show an exemplary bone plate 200 having a hinge joint 202 locked with a connector 204. Plate members 206, 208 of the bone plate are fitted together via a pair of arcuate, complementary mating regions 210, 212 centered around and bracketing pivot axis 214 of hinge joint 202.

Each complementary region 210, 212 includes a mating feature. For example the complementary region may include a track 216 defined as an arcuate channel, and an end region, such as a flange 218, that fits into and is complementary to the track (see FIG. 11). Each track 216 may have an undercut region 220 that retains the flange in the track and resists separating movement of plate members 206, 208 from one another in opposite directions parallel to pivot axis 214. More generally, the complementary mating features prevent translational disassembly of the mated plate members. However, each flange 218 can slide in-plane in the track as plate members 206, 208 are pivoted relative to one another about pivot axis 214. The plate members can be mated with one another initially by placing each flange 218 in its corresponding track, with the plate members arranged obliquely to one another (e.g., at an angle of at least about 20, 40, or 60 degrees from coaxial to one another, among others). The plate members then may be rotationally mated with one another by pivoting the plate members toward coaxial alignment with one another. The plate members will remain connected to one another in this mated configuration unless they are pivoted far enough out of alignment to remove each flange from its corresponding track. In some embodiments, the hinge joint may have only one flange and one track formed on only one side of pivot axis 214. In some embodiments, one of the plate members at the hinge joint may form flanges on opposite sides of the pivot axis, and the other plate member may define both tracks for receiving both flanges.

Plate members 206, 208 may define a pair of aligned apertures 222, 224 to receive connector 204. The connector may attach to lower aperture 224 by threaded engagement, to ensure that the plate members cannot be inadvertently disconnected from one another. The connector also may function as a lag screw, with a head that can be tightened against the upper plate member near the hinge joint to create tight engagement of the plate members with one another to lock the hinge joint at a selected position. Connector 204 optionally may include a threaded leading region 226 configured to project below the bone plate and into underlying bone.

Figure 12:
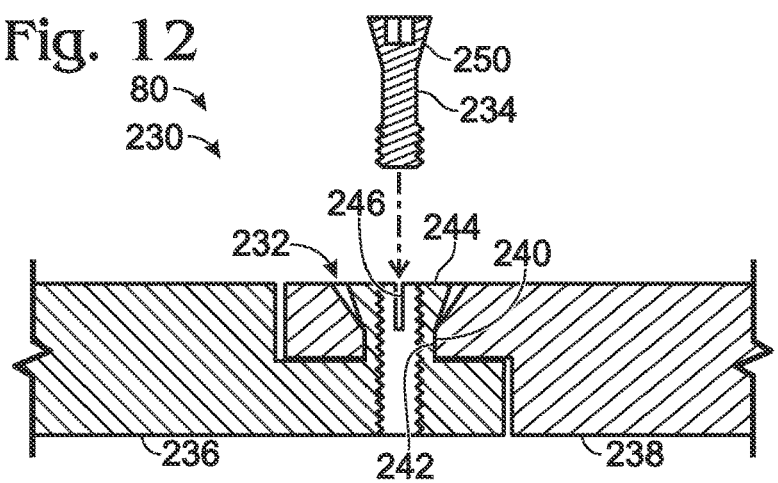
FIG. 12 is a longitudinal sectional view of an exemplary bone plate having a hinge joint that is lockable with an expandable collet, shown in the unlocked configuration before collet expansion.
Figure 13:
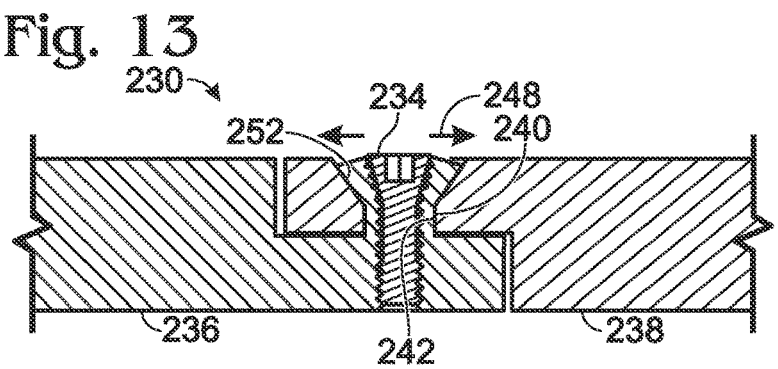
FIG. 13 is a view of the bone plate of FIG. 12, taken as in FIG. 12 after expansion of the collet with a fastener to lock the hinge joint.

FIGS. 12 and 13 show a bone plate 230 having a hinge joint 232 that is lockable with a connector 234. The bone plate includes a pair of plate members 236, 238 that overlap at the hinge joint. Lower plate member 236 may define a tab from which an axle 240 projects, as described above (e.g., see FIGS. 2-6). The axle may be received in an upper aperture 242 of the hinge joint and may be swaged and machined to form an expandable head or collet 244. The collet may define notches 246 that allow sections of the collet to expand radially, indicated by arrows at 248. Connector 234 may be threaded into lower plate member 236, and a tapered head 250 of the connector may be advanced into collet 244 of axle 240, which expands collet 244 to produce a friction lock due to engagement of the expanded collet with a tapered wall region 252 of aperture 242.

Figure 14A:
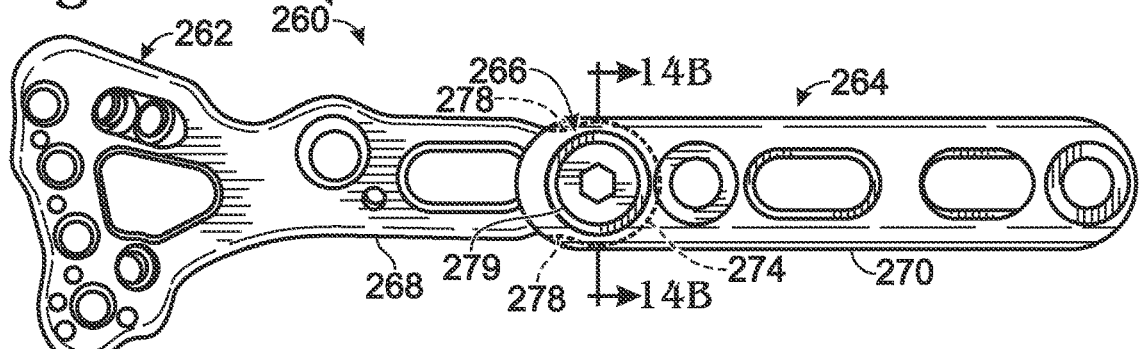
FIG. 14A is a plan view of an exemplary bone plate for fixation of the distal radius, with the bone plate having a segmented shaft including a hinge joint.
Figure 14B:
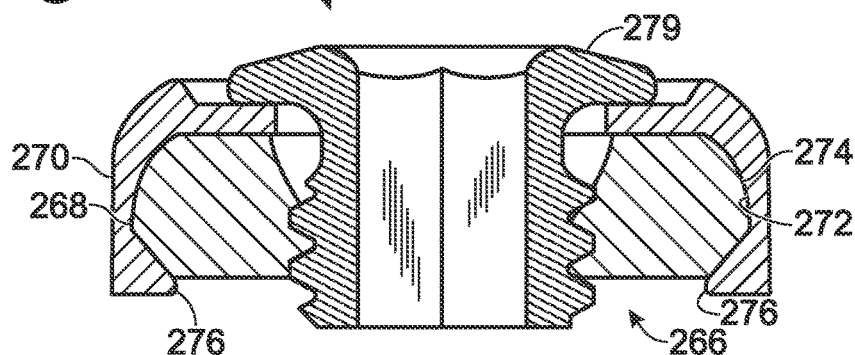
FIG. 14B is a sectional view of the bone plate of FIG. 14A, taken generally along line 14B-14B of FIG. 14 through the hinge joint.

FIGS. 14A and 14B show an exemplary bone plate 260 for fixation of the distal radius. Bone plate has a head portion 262 for mounting to the distal end of the radius on a volar side thereof, and a shaft portion 264 extending from the head portion. Shaft portion 264, also termed a stem portion, may be mounted to the shaft of a radial bone proximal to the head portion, such that the shaft portion extends at least generally parallel to the long axis of the radial bone.

Shaft portion 264 may be formed by at least two segments connected by a hinge joint 266 that permits in-plane adjustment of the bone plate. A distal segment of the shaft portion may be formed by a distal plate member 268 that also forms head portion 262. A proximal plate member 270 may form a proximal segment of the shaft. The distal and proximal segments of the shaft portion may have any suitable relative lengths, such as approximately equal lengths or different lengths (e.g., with the distal segment longer or shorter than the proximal segment). In some embodiments, the bone plate may be supplied by a kit having two or more proximal plate members of different length, each interchangeably attachable to the distal plate member via the hinge joint. The surgeon also may have the option of installing the distal plate member without proximal plate member 270.

Hinge joint 266 may include an end region of one of the plate members nested in an end region of the other plate member. For example, in the depicted embodiment, proximal plate member 270 defines a receiving space 272 that has received an end region 274 of distal plate member 268. The proximal plate member may trap the end region of the distal plate member in the receiving space. For example, the receiving space may be defined in part by a pair of lips 276 of plate member 270 that prevent separation of the plate members from one another in a direction parallel to the pivot axis of the hinge joint. The distance between the lips also may decrease toward the entry end of the receiving space to prevent separation of the plate members from one another in a direction parallel to the long axis of shaft portion 264. For example, the lips may be deformed generally toward one another at a transversely indented region 278 of end region 274 of plate member 268, after the plate members have been mated with one another, to prevent axial separation of the plate members, whether or not a connector 279 is installed. Connector 279 (e.g., a lock screw) may extend between aligned apertures of plate member 268, 270, and may be adjustable to lock the hinge joint, to fix the orientation of the plate members relative to one another. The connector is coaxial with the pivot axis of the hinge joint. In some embodiments, the head portion and the shaft portion of the bone plate also may be connected to one another by a movable joint, such as a multi-axis joint (e.g., see Section III and Example 4 of Section VII).

III. BONE PLATES WITH MULTI-AXIS JOINTS

This section describes exemplary bone plates with multi-axis joints that permit adjustment of the angular orientation of a pair of plate members relative to one another in each of two or more planes that are nonparallel to one another; see FIGS. 15A-15E and 16-36. Further aspect of bone plates with multi-axis joints are described elsewhere herein, such as in Section VII (e.g., in Example 4).

Bone plates having a multi-axis joint are known. However, the multi-axis joint relies on friction to prevent movement of joint surfaces when the joint is locked. When the joint is loaded after installation of the bone plate, slippage of the joint surfaces relative to one another may occur. Multi-axis joints more resistant to slippage are needed.

The multi-axis joints disclosed in this section and in Example 4 of Section VII, among others, are configured to lock the joint more reliably, such that the joint can withstand a greater load without slippage. The joint may utilize material deformation and/or interfitment of complementary mating features to prevent slippage.

FIGS. 15A-15E each show a joint region of a bone plate 280 having a deformable multi-axis joint. Each embodiment of bone plate 280 has a pair of plate members 281, 282 that are connected to one another with a discrete connector (e.g., a lock screw). The connector can be manipulated to change the joint from a movable configuration (on the left) to a fixed configuration (on the right), and vice versa. In the movable configuration, the orientation of plate members 281, 282 relative to one another can be adjusted, indicated by a curved motion arrow 283, in each of two or more nonparallel planes. In the fixed configuration, the multi-axis joint is locked and the orientation of the plate members cannot be adjusted. The fixed configuration may be generated by compressive force applied to the plate members via the connector, which urges joint surfaces 283a, 283b of the plate members toward one another at the joint, indicated by a pair of motion arrows at 284 (see FIG. 15A).

Joint surfaces 283a, 283b overlap and face one another. As described further below, one or both joint surfaces may have one or more surface features (i.e., one or more protrusions or voids) that encourage deformation of one or both joint surfaces when the joint is placed in the fixed configuration. Also, or alternatively, one or both joint surfaces may be formed non-integrally, which allows a material property, such as the hardness, of at least one of the joint surfaces to vary across the joint surface.

Figure 15A:
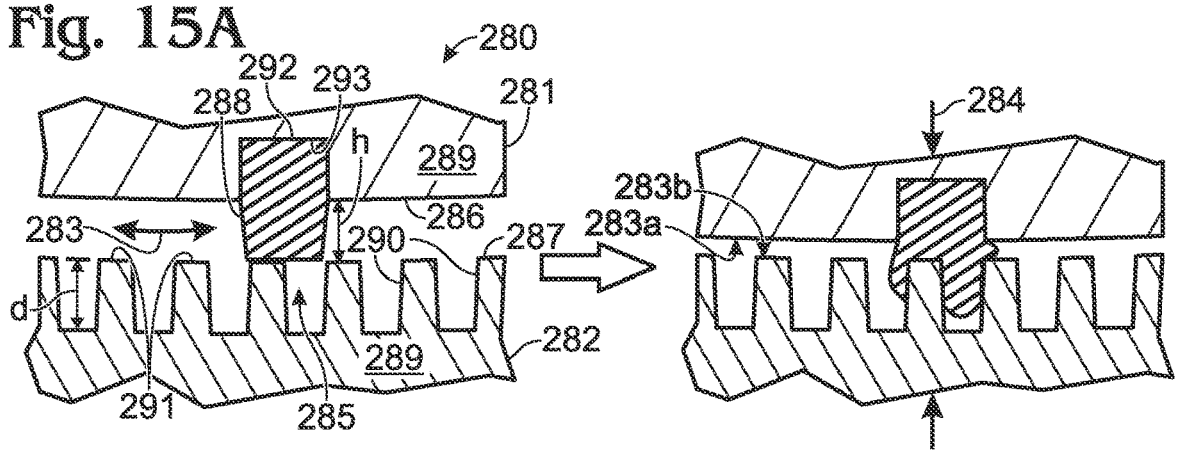
FIGS. 15A-15E are schematic, fragmentary sectional views of exemplary bone plates having a multi-axis joint, taken through the joint before and after placement of the joint in a fixed configuration, and illustrating various arrangements and interactions of protrusions, voids, and deformable elements, in accordance with aspects of the present disclosure.

Compressive force may be directed to an interface 285 at which joint surfaces 283a, 283b contact one another in the movable configuration before the joint is locked (see FIG. 15A). The interface may be only a fraction of the area of the joint surfaces (e.g., less than 50, 25, or 10% of the area), to increase the force per unit area at the interface and promote deformation at the interface. One or both of the plate members may be deformed at the interface. This deformation causes the plate members to locally obstruct movement 283 relative to one another, which can lock the joint much more effectively and stably than friction. The shear strength of the plate members where they obstruct one another becomes important in preventing movement at the joint.

Joint surfaces 283a, 283b may include respective joint surface regions 286, 287 that are complementary to one another. The surface regions each may be spherical, with the same radius of curvature, and may form any suitable continuous or non-continuous portion of a complete sphere. Overlying surface region 286 may be convex, as shown, or concave. Underlying surface region 287 may be concave, as shown, or convex. Furthermore, the relative positions (underlying/overlying) of the plate members may be switched.

Joint surface 283a forms at least one protrusion 288 configured to deform and/or be deformed by joint surface 283b when the joint is placed in the fixed configuration. Deformation may be plastic, elastic, or a combination thereof. Each protrusion 288 is raised (elevated) with respect to surface region 286, as shown, and may project from the surface region. The one or more protrusions may be discrete from surface region 286 (see FIGS. 15A-15C) or integral with the surface region (see FIGS. 15D and 15E). Accordingly, a body 289 of the plate member that forms surface region 286 (and defines one or more through-holes to receive fasteners) may be discrete or unitary with protrusion 288. Each protrusion projects beyond surface region 286 toward plate member 282 and joint surface 283b. The protrusion may, for example, project from a position within or outside the perimeter of surface region 286. Exemplary protrusions include ridges, studs, or the like.

Protrusions 288 may constitute less than one-half of the area of joint surface 283a. For example, the protrusions may constitute less than 25% or 10% of the area, to concentrate compressive force at the protrusions.

Figure 15B:
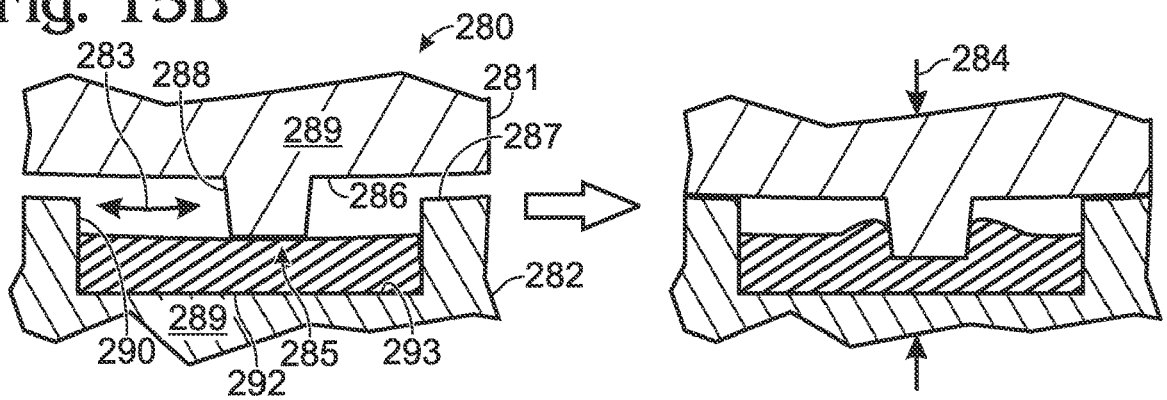

Joint surface 283b may define one or more voids 290 that are recessed with respect to surface region 287. Each void may extend into plate member 282 from surface region 287 any suitable distance and may or may not be elongated along or transverse to the surface region. The voids are configured to receive at least a portion of each protrusion 288 when the joint is placed in the fixed configuration. The protrusion may be disposed in and/or extend into at least one of the voids after (FIGS. 15A, 15D, and 15E), or both before and after (FIG. 15B), the joint is placed in the fixed configuration. In any event, at least a portion of each protrusion enters a space created by at least one void (with or without void deformation), and the protrusion extends into or extends more deeply into the at least one void when the joint is placed in the fixed configuration. Voids and surface region 287 may be formed integrally with one another (FIGS. 15A, 15D, and 15E) or may be formed at least in part with a discrete element (FIG. 15B). In some embodiments, the one or more voids may isolate areas 291 of surface region 287 from one another (see FIG. 15A). For example, joint surface 283a may define intersecting surface channels that surround and isolate areas 291 from one another. In other embodiments, surface region 287 may be continuous.

Voids may have a depth (d) with any suitable relationship to a height (h) of each protrusion 288. For example, the depth may be at least 10, 25, 50, or 100% of the height. Exemplary depths (d) of the voids and/or heights (h) of the protrusion(s) include at least 0.1, 0.2, 0.5, or 1 millimeter, among others. In some embodiments, the depth may be greater than the height, to encourage "bottoming out" in which surface region 286 engages surface region 287 (see FIGS. 15D and 15E). Engagement of surface regions 286, 287 with one another may enhance the stability of the locked joint.

One or both of the plate members may include at least one deformable element 292 that is discrete from body 289 of the plate member. The deformable element(s) may be created in a spaced relationship to body 289 and then associated with the body, or the deformable element(s) may be created on the body, such as by addition of material to the body (e.g., by overmolding, spraying, etc.). The deformable element(s) may be more deformable (plastically and/or elastically) than either body 289, either surface region 286 or 287, the other plate member, or any combination thereof, among others. Each deformable element may be formed of a different material than body 289 (e.g., a softer material), may be more porous, or the like. The deformable element may be disposed in a recess 293 defined by body 289 and may project from the recess to form protrusion 288 (see FIG. 15A). The deformable element may be attached to the body, whether or not the deformable element is disposed in a recess. Attachment may be achieved by press-fitting, bonding, an adhesive, creating the deformable element on the body, or the like. In some embodiments, the deformable element may form a protrusion 294 of joint surface 283b (of plate member 282) that can contact and be deformed by a protrusion 288 of joint surface 283a (of plate member 281) (see FIG. 15C).

FIG. 15A shows deformable element 292 being deformed by joint surface 283b of plate member 282, such that the deformable member extends into plate member 282 beyond surface region 287. In the depicted embodiment, voids 290 are not deformed substantially when the joint is placed in the fixed configuration. In some embodiments, the voids may be larger (e.g., wider), such that the entire protrusion can be received in a single void and surface regions 286, 287 can engage one another.

FIG. 15B shows protrusion 288 extending beyond surface region 287 of plate member 282 into a void 290 defined collectively by body 289 and deformable element 292. The protrusion can slide along a surface of the deformable element in the movable configuration of the joint, and extends into the deformable element in the fixed configuration of the joint. The protrusion extends beyond surface region 287 into plate member 282 in both the movable and fixed configurations, but extends farther in the fixed configuration.

Figure 15C:
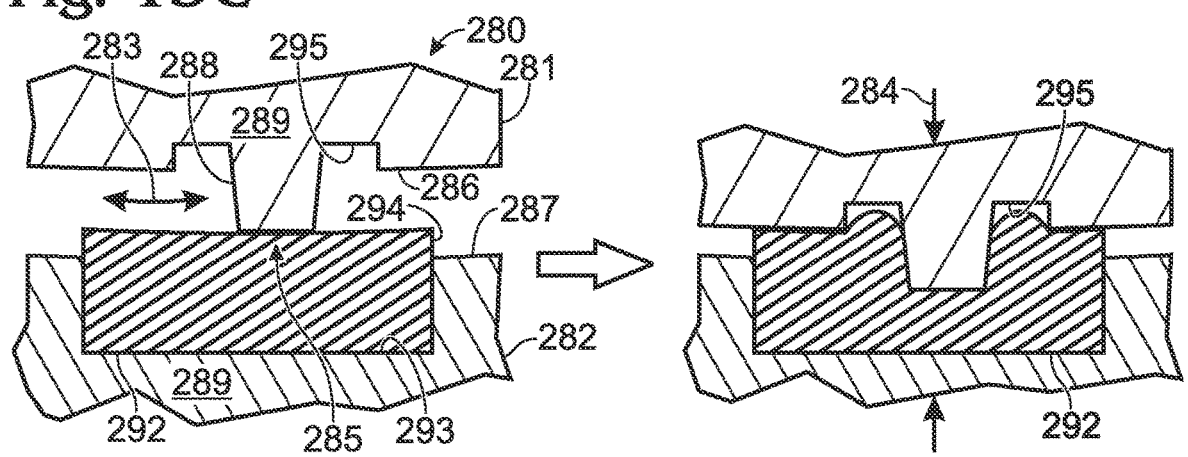

FIG. 15C shows protrusion 288 of plate member 281 in slidable contact with deformable protrusion 294 of plate member 282. Protrusion 288 extends into the deformable element 292 when the joint is placed in the fixed configuration. A depression 295 formed at the base of protrusion 288 receives a portion of deformable element 292.

Figure 15D:
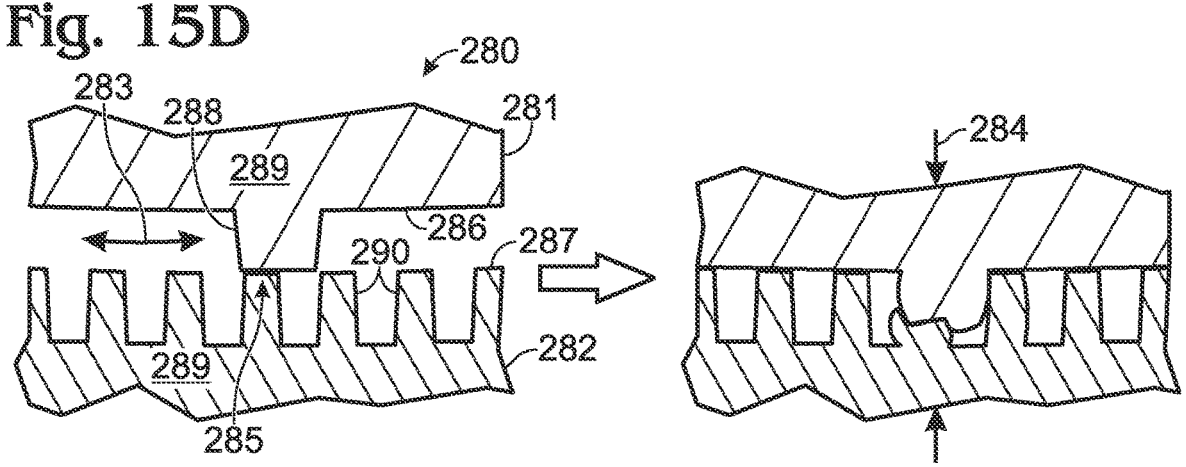
Figure 15E:
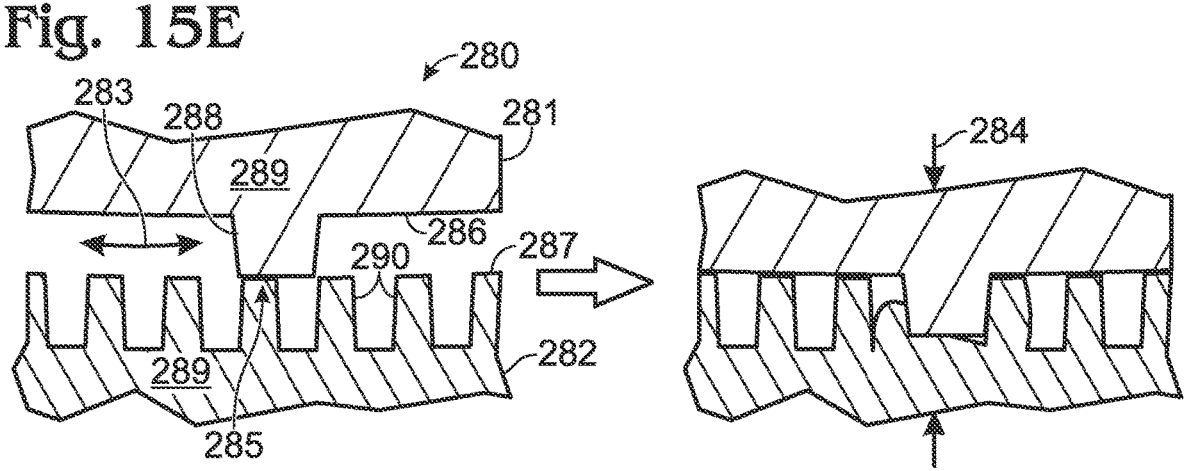
Figure 17:
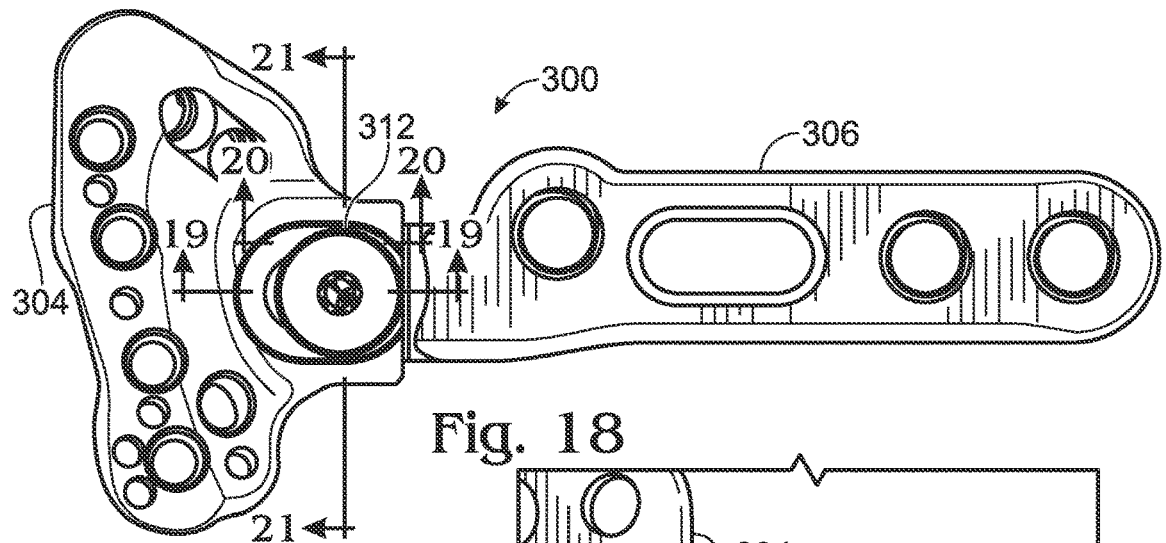
FIG. 17 is a plan view of the bone plate of FIG. 16 taken with the bone plate assembled.

FIGS. 15D and 15E show bone plates 280 that do not have a discrete deformable element 292. Protrusion 288 is formed integrally with surface region 286, and voids 290 are formed integrally with surface region 287. In FIG. 15D, the plate members have about the same hardness. Accordingly, protrusion 288 and at least one void 290 are deformed. In FIG. 15E, plate member 282 is softer than plate member 281. Plate member 282 is deformed predominantly. In other embodiments having integrally formed joint surfaces, plate member 281 (and particularly each protrusion 288) is deformed predominantly.

FIGS. 16-21 show an exemplary bone plate 300 for fixation of the distal radius. Bone plate 300 has a multi-axis joint 302 movably connecting a head plate member 304 to a shaft plate member 306 of the bone plate. The multi-axis joint of the depicted embodiment (and in other embodiments disclosed herein for the distal radius) permits continuous dorsal-ventral adjustability and continuous radial-ulnar adjustability of the head plate member relative to the shaft plate member. Head plate member 304 includes a pair of deformable elements 308 (anti-slip elements) that form protrusions of the joint surface of the plate member (also see FIG. 15A). Shaft plate member 306 has a joint surface defining voids 310 in the form of channels that receive a portion of each deformable element as the joint is compressed and locked by a connector 312 (which may be a lock screw).

The joint surfaces of plate members 304, 306 include respective complementary joint surface regions 314, 316 (such as spherical surface regions with the same radius of curvature) that face one another in a region of overlap 317 of bone plate 300. Head surface region 314 may be concave, and shaft surface region 316 may be convex (or vice versa). Also, the head surface region may be above or below the shaft surface region.

Figure 18:
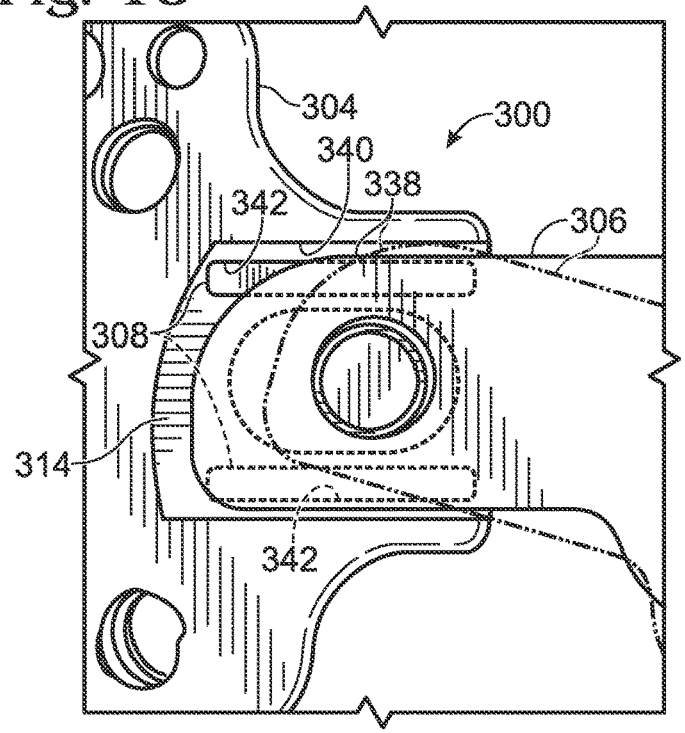
FIG. 18 is a fragmentary bottom view of the bone plate of FIG. 16, taken generally around the multi-axis joint with the bone plate assembled.
Figure 19:
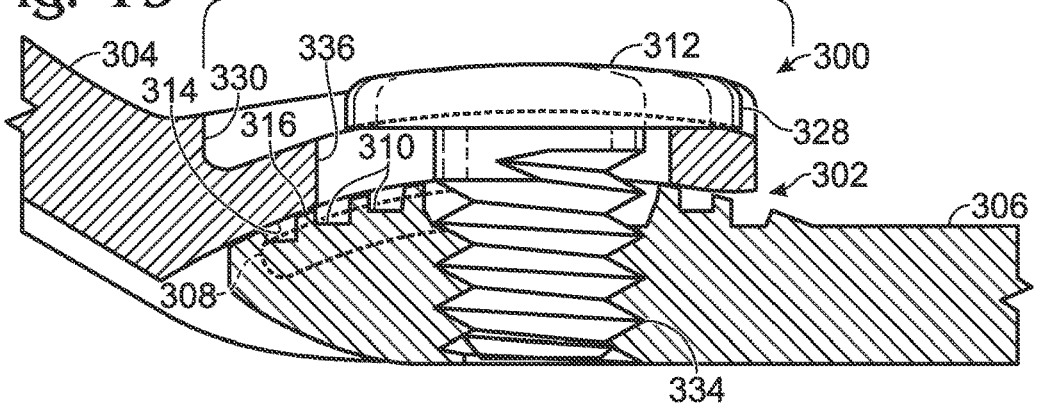
FIG. 19 is a fragmentary, longitudinal sectional view of the bone plate of FIG. 16, taken generally along line 19-19 of FIG. 17 centrally through the multi-axis joint.

The multi-axis joint may permit adjustment of the orientation of the plate members relative to one another in two or more nonparallel planes. The orientation may be adjusted in-plane about a central axis 318 of connector 312. (In other words, the orientation may be adjusted in a plane orthogonal to central axis 318.) The connector is received in (and axis 318 extends through) a pair of aligned apertures 320, 322 (also called openings) defined by the respective plate members. FIG. 18 illustrates in phantom an adjusted position for shaft plate member 306 after in-plane motion. The orientation also may be adjusted about each of a pair of axes 324, 326 that are transverse (e.g., substantially orthogonal) to one another and to central axis 318 (see FIG. 16). (In other words, the orientation may be adjusted in a pair of planes that are respectively orthogonal to axes 324 and 326.) Axes 324 and 326 may be spaced from and disposed below the inner (bottom) surface of the bone plate, as shown. Alternatively, axes 324 and 326 may be spaced from and disposed above the outer (top) surface of the bone plate (see below) or may intersect the bone plate, among others.

The range of motion permitted by joint 302 may be determined by any suitable combination of contact between (a) a head 328 of connector 312 and a side wall 330 of a recessed region 332 formed by upper aperture 320 (e.g., see FIGS. 16, 19, and 20), (b) a shaft 334 of connector 312 and a lower side wall region 336 of elongated upper aperture 320 (e.g., see FIGS. 16 and 19), and (c) a perimeter wall region 338 of shaft plate member 306 and a side wall region 340 near joint surface region 314 (e.g., see FIGS. 16 and 18). In exemplary embodiments, the joint permits an range of adjustment of the volar tilt of the head plate member relative to the shaft plate member (about axis 324) of about 10-20 degrees, among others, and a range of adjustment of the radial-ulnar tilt about axis 318 of about 6-10 degrees, among others.

Figure 20:
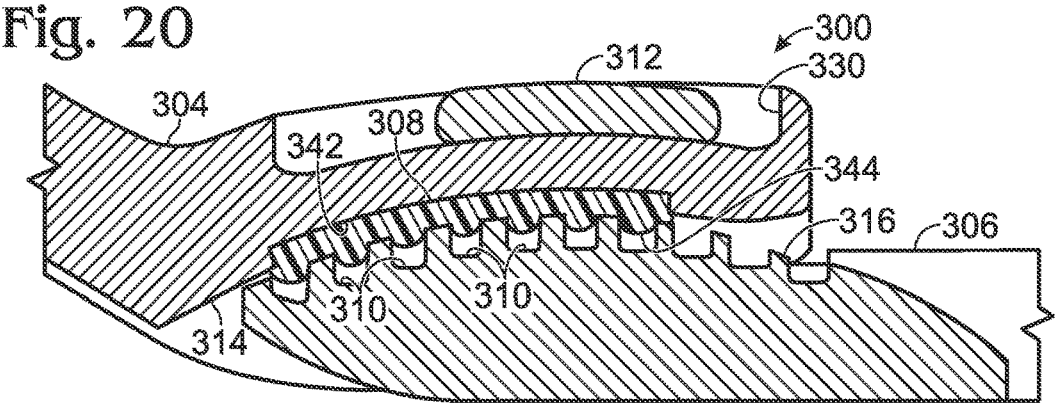
FIG. 20 is another fragmentary, longitudinal sectional view of the bone plate of FIG. 16, taken generally along line 20-20 of FIG. 17 laterally through the multi-axis joint.
Figure 21:
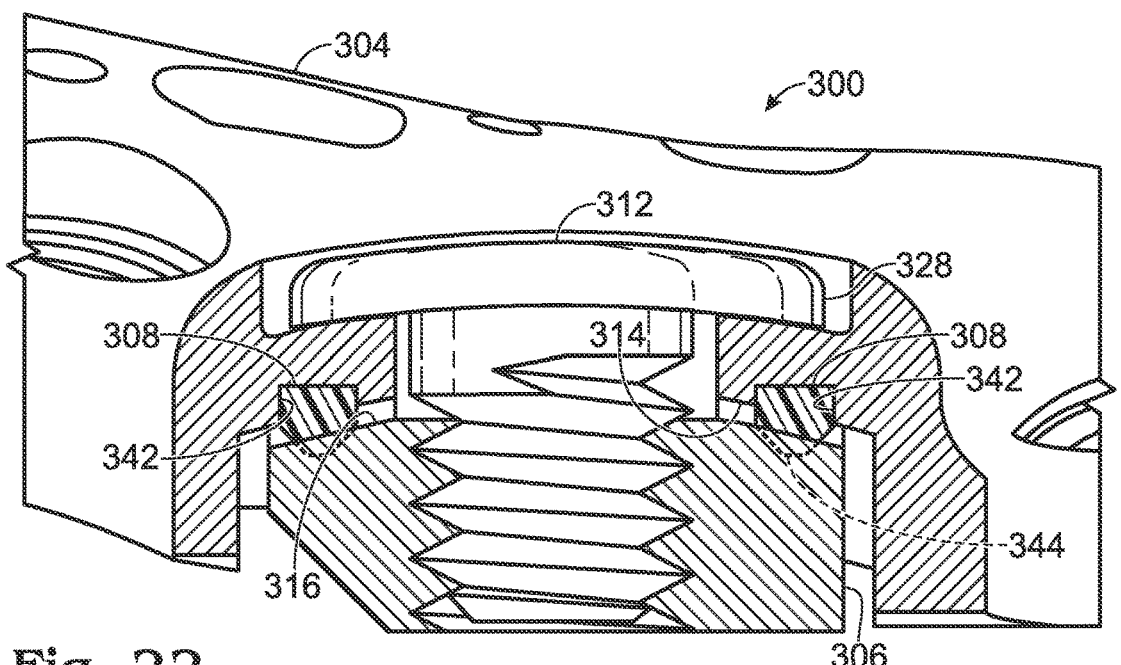
FIG. 21 is a fragmentary, cross-sectional view of the bone plate of FIG. 16, taken generally along line 21-21 of FIG. 17 centrally through the multi-axis joint.
Figure 22:
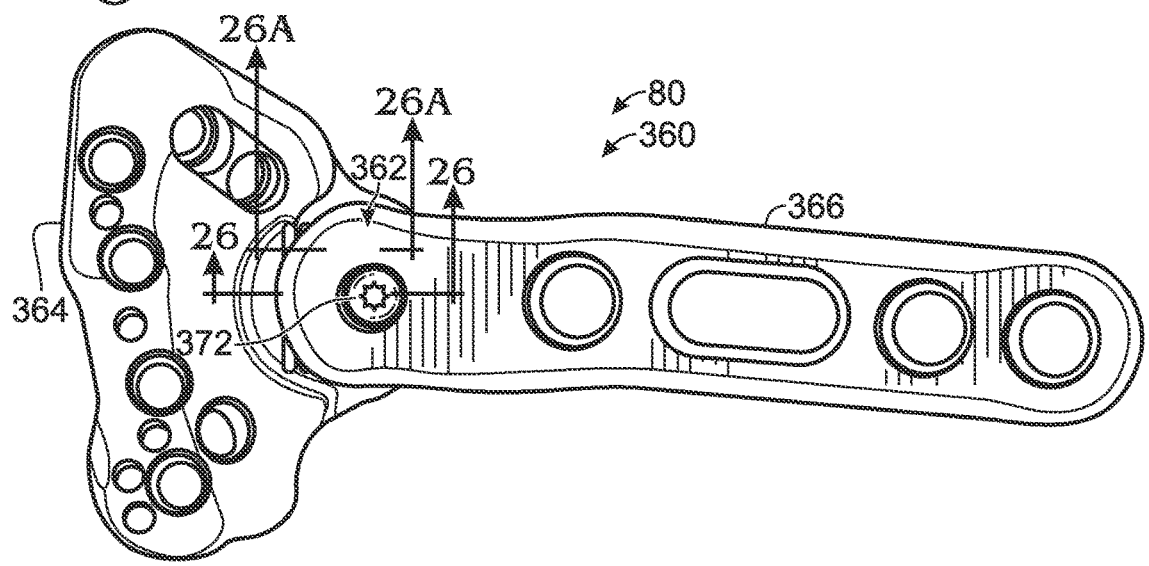
FIG. 22 is a plan view of another exemplary bone plate for fixation of the distal radius, with the bone plate having a multi-axis joint generally as in FIG. 16 but with a connector that is inverted with respect to the bone plate of FIG. 16.
Figure 23:
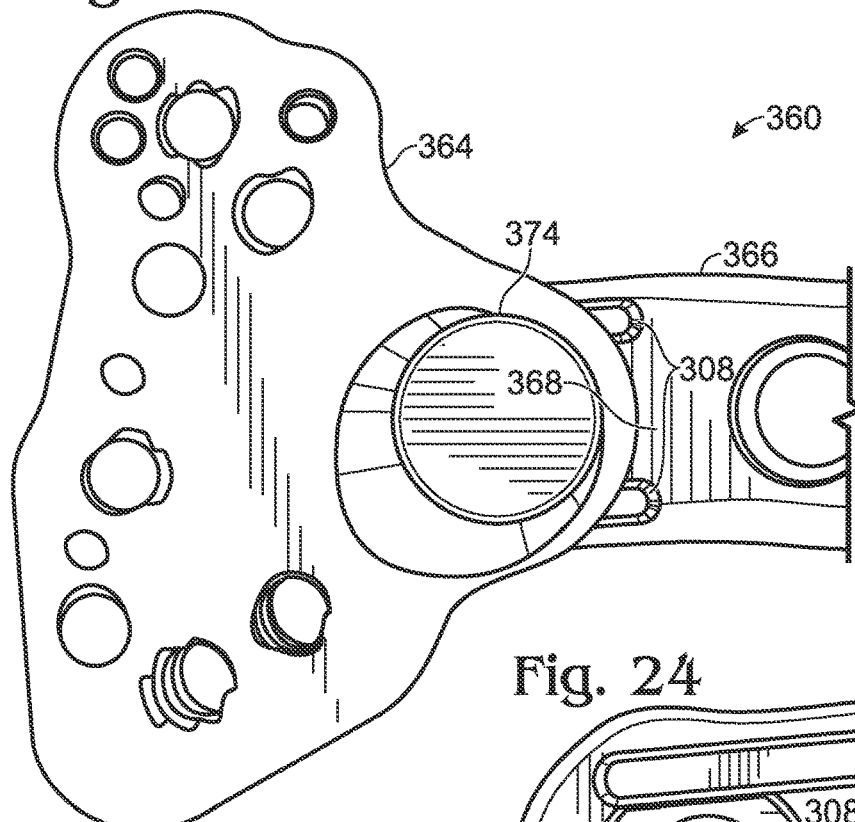
FIG. 23 is a fragmentary bottom view of the bone plate of FIG. 22.

Deformable elements 308 may be disposed in recesses 342, such as furrows, which may defined within the perimeter of upper joint surface region 314 (see FIGS. 18, 20, and 21). Each deformable element may be attached to plate member 304 in one of recesses 342. Each recess 342 and the deformable element 308 disposed therein may be elongated transverse to voids 310, such that voids 310 and deformable elements 308 are oriented crosswise relative to one another. Each deformable element 308 may protrude from its corresponding recess 342, to form a protrusion 344 that is raised relative to surface region 314 (see FIGS. 20 and 21). In other words, the protrusion extends beyond surface region 314 toward the other surface region 316. When connector 312 is tightened to compress the joint, each deformable element 308 may be deformed such that a portion of the deformable element (and a portion of protrusion 344) enters at least one void 310.

Deformable element 308 may leverage the shear strength of a material jammed between two metal surfaces for a continuous (non-discrete) adjustment of the plate members relative to one another at the joint. This approach may be more effective than the use of a friction lock, which may be more susceptible to slippage, or the use of potentially less user-friendly inter-fitted teeth, which generally require one of the plate members (and particularly its joint surface) to move up and down at the joint as the register of complementary sets of teeth is changed. Each deformable element 308 may, for example, be formed of metal or any suitable polymer, such as polyether ether ketone (PEEK) or a carbon-fiber PEEK composite, among others. The amount of deformation of the deformable element may help to determine the holding strength of the joint.

FIGS. 22-26 and 26A show another exemplary bone plate 360 for fixation of the distal radius. Bone plate 360 may be constructed generally as described above for bone plates 280 and 300 (see FIGS. 15A and 16-21) and may have any suitable combination of features described for bone plates 280 and 300 and any other bone plates of the present disclosure.

Bone plate 360 has a multi-axis joint 362 formed at a region of overlap of a head plate member 364 and a shaft plate member 366. Plate members 364 and 366 respectively form surface regions 367, 368 of the joint arranged on a sphere 369 having a center 370 below the bone plate (see FIG. 26). Shaft plate member 366 may overlie head plate member 364 at the joint, rather than underlying the head plate member as in bone plate 300 (compare FIGS. 22 and 26 with FIGS. 16 and 19).

Figure 26:
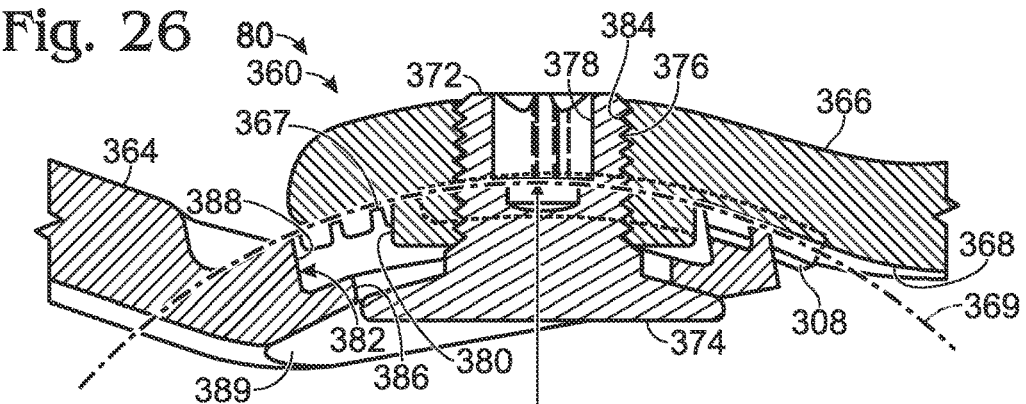
FIG. 26 is a fragmentary, longitudinal sectional view of the bone plate of FIG. 22, taken generally along line 26-26 of FIG. 22 through a center of the multi-axis joint.
Figure 26A:
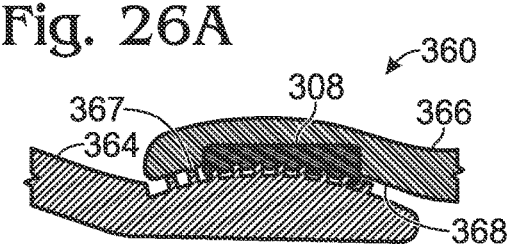
FIG. 26A is a fragmentary, longitudinal sectional view of the bone plate of FIG. 22, taken generally along line 26A-26A of FIG. 22 laterally through the multi-axis joint.

Multi-axis joint 362 may be locked (placed in a fixed configuration) by a connector 372 (e.g., a lock screw) having a head 374 disposed under, rather than over, joint surface regions 367, 368 of the plate members (see FIG. 26). However, the end of a shaft 376 of the connector, instead of the connector's head, may define a driver interface 378 (e.g., a hexagonal socket, among others). Accordingly, the joint may be locked and released from the outer side of bone plate 360 after the bone plate has been placed onto and/or attached to bone.

Connector 372 may have a thread that is reverse-handed relative to the threads of other fasteners used to secure the bone plate to bone, to make manipulation of the connector more intuitive for the surgeon. For example, if the bone plate is secured to bone with bone screws having right-handed threads, the connector may have a left-handed thread, such that the surgeon turns the bone screws and the connector in the same direction (clockwise (from above)) to tighten the bone screws against the bone plate and to lock the joint.

Figure 24:
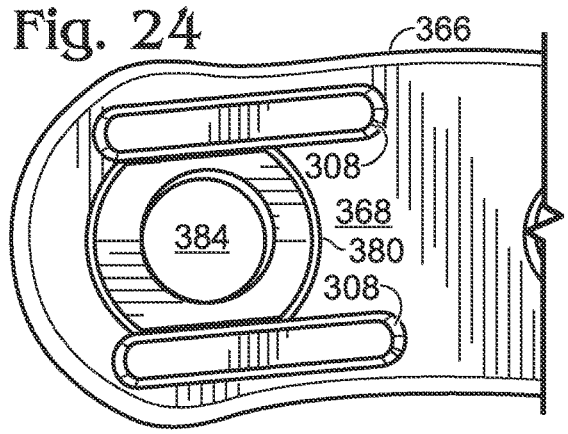
FIG. 24 is a fragmentary bottom view of a shaft plate member of the bone plate of FIG. 23, taken in the presence of a pair of deformable elements of the plate member and in the absence of a head plate member of the bone plate.
Figure 25:
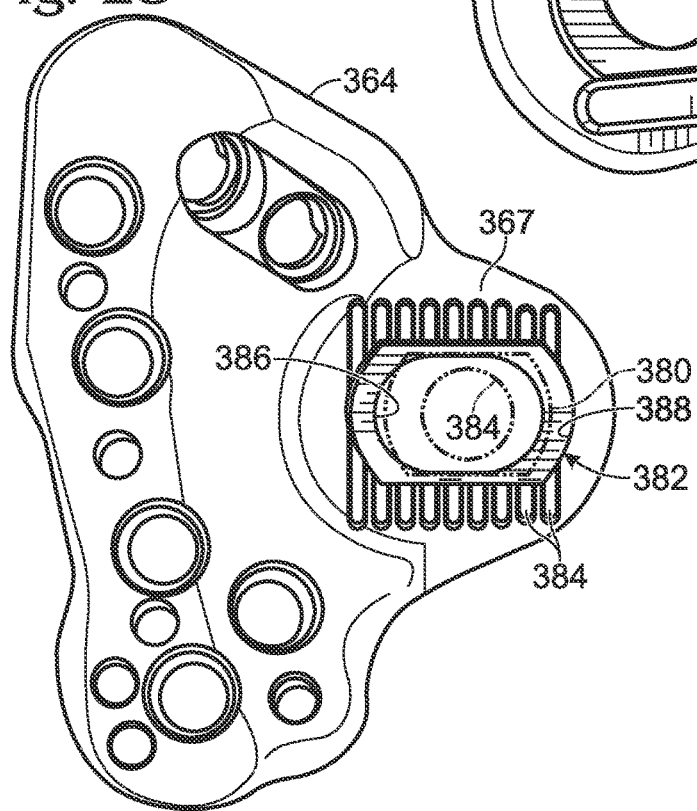
FIG. 25 is a plan view of the head plate member of the bone plate of FIG. 23, taken in the absence of the shaft plate member and the deformable elements of FIG. 24.

The range of motion permitted by multi-axis joint 362 may be determined by a stop region formed cooperatively by a raised member or projection 380 (also called a boss) of shaft plate member 366, and an aperture 382 defined by head plate member 364 (see FIGS. 24-26). Aperture 382 receives projection 380 and connector 372. The aperture may be defined central to the joint surface and/or joint surface region 367 of the member. Contact between the perimeter wall of projection 380 and the perimeter wall of aperture 382 may establish a range of motion of the plate members relative to one another in each plane of adjustment permitted by the joint. The use of a projection 380 positioned inside bone plate 360 to determine the range of motion of joint 362 is advantageous because the range of motion can be defined without affecting the external geometry of the bone plate. Accordingly, the external shape of the bone plate can be designed for optimal performance and subject compatibility with the joint in the fixed configuration.

Aperture 382 and an aligned aperture 384 defined by shaft plate member 366 receive portions of shaft 376 of connector 372 (see FIG. 26). Aperture 384 is internally threaded for attachment to shaft 376 via the shaft's external (left-handed) thread. Aperture 384 extends through projection 380, and projection 380 may be centered on aperture 384.

Aperture 382 may have two or more distinct regions arranged between the inner surface and the outer surface of head plate member 364 (see FIGS. 25 and 26). The aperture has a minimum-width region 386 that is narrower than the diameter of the connector's head 374, to prevent the head from passing through aperture 382. Aperture 382 also has a wider region between minimum-width region 386 and the outer surface of head plate member 364, to form a receiver 388 for projection 380. Aperture 382 also may widen as it extends from minimum-width region 386 to the inner surface of the head plate member, to form a space 389 for receiving head 374 of the connector.

Deformable elements 308 may be arranged to be deformed by contact with the opposite joint surface when the joint is compressed, as described above for bone plate plates 280 and 300 (see FIGS. 24, 25, and 26A, and also see FIGS. 15A, 16, and 20).

Figure 27A:
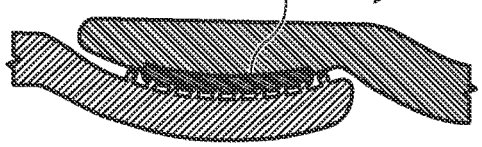
FIG. 27A is a fragmentary, longitudinal sectional view of the bone plate of FIG. 27, taken generally as in FIG. 26A for comparison with the bone plate of FIG. 26.
Figure 27:
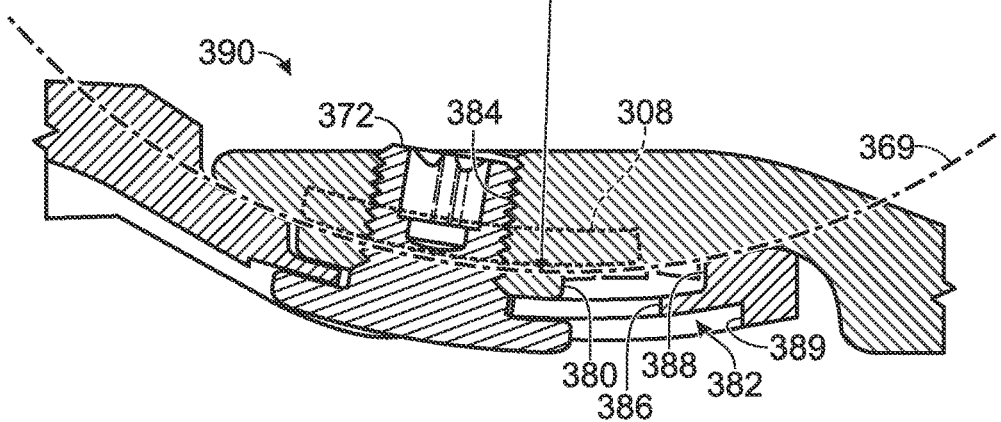
FIG. 27 is a fragmentary, longitudinal sectional view of another exemplary bone plate having a multi-axis joint, taken generally as in FIG. 26, with the multi-axis joint having a curvature that is inverted with respect to the bone plate of FIG. 26.

FIGS. 27 and 27A show yet another exemplary bone plate 390 for distal radius fixation. Bone plate 390 is similar to bone plate 360 except that the joint surfaces are curved upward (away from bone) rather than downward (toward bone), to position a center of rotation 392 above rather than below the bone plate (compare FIG. 26 with FIG. 27, and FIG. 26A with FIG. 27A). Structures for establishing the range of motion in each plane are labeled with the same reference numbers as for bone plate 360.

FIG. 28 shows another exemplary bone plate 410 for fixation of the distal radius. (Fastener-receiving through-holes of each plate member have been omitted to simplify the presentation.) Bone plate 410 has a head plate member 412 connected to a shaft plate member 414 by a multi-axis joint 416. An inverted lock screw 418 and a triangular nut 420 are attached to one another by threaded engagement to hold the joint together. Nut 420 may be received in a triangular aperture 422 that is defined by one of the plate members and that is oversized with respect to the nut. The difference in size between the nut and the aperture determines the range of motion of the plate members in each plane. The orientation of the plate members can be adjusted in a given plane until contact between a wall of the nut and a perimeter of the aperture blocks further movement in that plane. In other embodiments, the nut may be formed integrally by one of the plate members.

FIG. 29 shows still another exemplary bone plate 440 for fixation of the distal radius. Bone plate 440 has a head plate member 442 and a shaft plate member 444 connected to each other at a multi-axis joint 446. A connector that extends through an upper aperture 448 defined by head plate member 442 and that threads into an internally-threaded lower aperture 450 defined by shaft plate member 444 is omitted to simplify the presentation. Head plate member 442 and shaft plate member 444 may have joint surfaces forming respective, complementary, convex and concave joint surface regions 452, 454 that face one another at the joint. The connector applies compression to the joint and urges the joint surfaces against one another to deform at least one of the joint surfaces and lock the joint at a selected position. The joint surfaces may be structured as described above for bone plate 280 of FIGS. 15D and 15E.

The joint surfaces may define one or more surface features that facilitate deformation of one or both of the plate members at the joint. In some embodiments, the surface features may be created by removing material from (or adding material to) a featureless precursor surface, which may create a pattern.

FIG. 30 shows the joint surface of plate member 444, which is composed of joint surface region 454 and a void 456 that is recessed with respect to joint surface region 454. The void may be formed by removal of material from a continuous, spherical precursor surface, to create a grid of channels that are recessed with respect to spherical surface region 454. The grid of channels creates discontinuities in the precursor surface such that joint surface region 454 is discontinuous and composed of separate surface areas.

FIGS. 31 and 32 show other examples of a joint surface for shaft plate member 444. The joint surface may be composed of joint surface region 454 and voids 456 structured as concentric grooves (FIG. 31) or parallel grooves (FIG. 32), which may be formed in a spherical precursor surface. In yet other examples, the grooves may, for example, be arranged radially, or may cross one another.

The voids and/or surface region 454 may be manufactured by any suitable process, such as milling, electrical discharge machining, sintering beads or other particles, photo-etching, 3D printing, etc. The process creates voids that a deformable material at the joint can enter as the joint is compressed to place the joint in a fixed configuration.

FIGS. 33-35 show exemplary structure for one or more protrusions 462 that are raised with respect to joint surface region 452 of head plate member 442, for contact with any of the joint surfaces and/or joint surface regions 454 of FIGS. 30-32. Each protrusion may be formed integrally with joint surface region 452. Alternatively, the protrusion may be formed separately (e.g., as a deformable element; see FIG. 15A) and then attached to the plate member near surface region 452 (e.g., within the perimeter of the surface region and/or with the protrusion projecting from the surface region). FIG. 33 shows a deformable ring protrusion 462. The ring protrusion may protrude from a groove 464 defined by a body 466 of head plate member 442 or may be formed integrally with the body. FIG. 34 shows a plurality of discrete protrusions 462 formed as bosses arranged around aperture 448 defined by body 466 of plate member 442. The bosses may protrude to a raised position from respective recesses 472 defined by body 466 or may be formed integrally with the body. FIG. 35 shows a plurality of protrusions 462 structured as parallel ridges.

Figure 36:
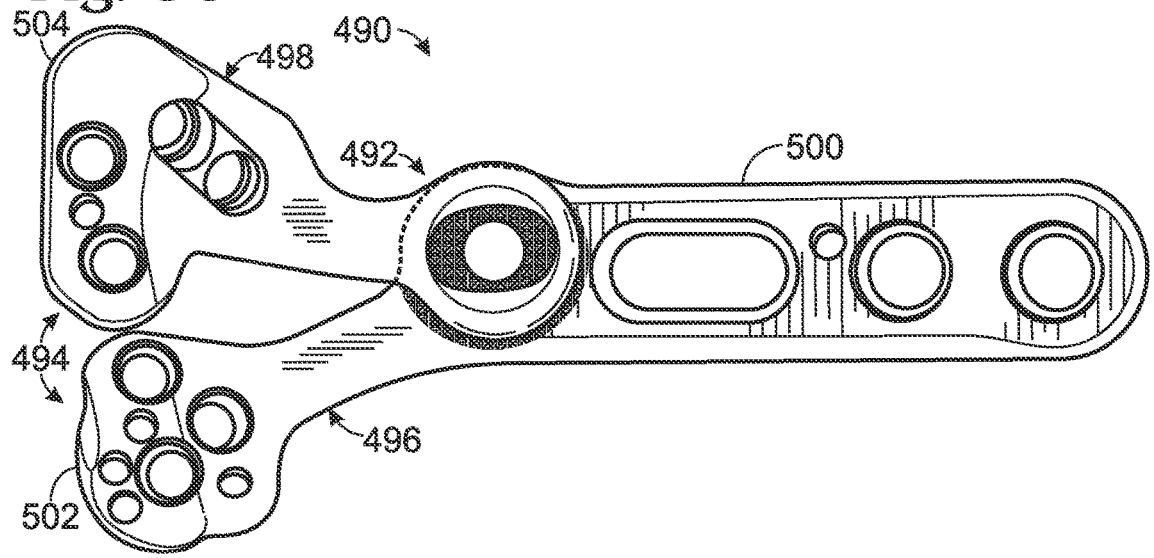
FIG. 36 is a plan view of selected aspects of still yet another exemplary bone plate for fixation of the distal radius and having a multi-axis joint, taken in the absence of a connector for the joint, with the bone plate having a head portion with a pair of transversely arranged head regions that are movable with respect to one another via the multi-axis joint, in accordance with aspects of the present disclosure.

FIG. 36 shows still another exemplary bone plate 490 for fixation of the distal radius. Bone plate 490 has a multi-axis joint 492 that may be structured and locked as described above for bone plate 440. However, bone plate 490 differs from bone plate 440 by having a head portion 494 formed collectively by a pair of plate members 496, 498 connected to one another at joint 492. Main plate member 496 may form a shaft portion 500 and an ulnar section 502 (or a radial section 504) of head portion 494. Branch plate member 498 articulates with main plate member 496 at a position along the main plate member that is intermediate shaft portion 500 and ulnar section 502. The branch plate member forms radial section 504 (or an ulnar section) of head portion 494. Ulnar section 502 and radial section 504 have a side-by-side arrangement in which the sections are arranged along a line from one another, with the line being transverse to a long axis of the bone plate.

Bone plates having joints permitting multi-axis adjustment have been illustrated for use on the distal radius, such as on a volar side thereof. However, in other embodiments, any of the bone plates may be shaped and sized for use on any other suitable bone, such as any long bone. Also, the bone plates may be configured to have a head portion for placement closer to an end of the long bone, and a shaft portion for placement farther from the end of the long bone, although in some embodiments, the bone plates may not have a head portion.

IV. BONE PLATES WITH SINGLE-AXIS JOINTS FOR OUT-OF-PLANE ANGULAR ADJUSTMENT

This section describes exemplary bone plates with joints that permit out-of-plane angular adjustment of plate members relative to one another, optionally in only one plane; see FIGS. 37-43.

The bone plates of this section may be used to fix any suitable bone. In exemplary embodiments, the bone plates may fix a tibia (e.g., proximally), a femur (e.g., distally), or a humerus (e.g., proximally), among others. The bone plates may, for example, provide a varus/valgus adjustment near the end of a bone. The adjustment permitted by each bone plate may be discrete or continuous.

Figure 37:
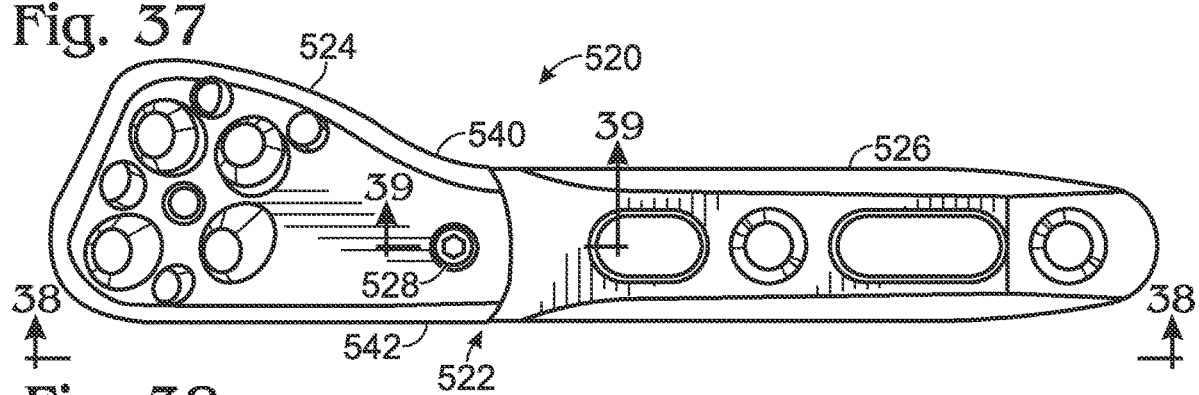
FIG. 37 is a plan view of an exemplary bone plate having a generally cylindrical joint that permits changing the orientation of a head plate member and a shaft plate member of the bone plate relative to one another in a plane that is at least generally parallel to the long axis of the bone plate and transverse (e.g., orthogonal) to a plane defined by the bone plate, in accordance with aspects of the present disclosure.
Figure 38:
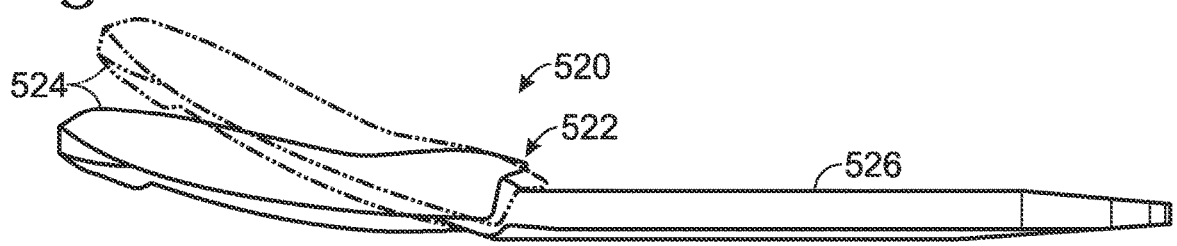
FIG. 38 is a side view of the bone plate of FIG. 37, taken generally along line 38-38 of FIG. 37, and illustrating movement of the head plate member relative to the shaft plate member in phantom.
Figure 39:
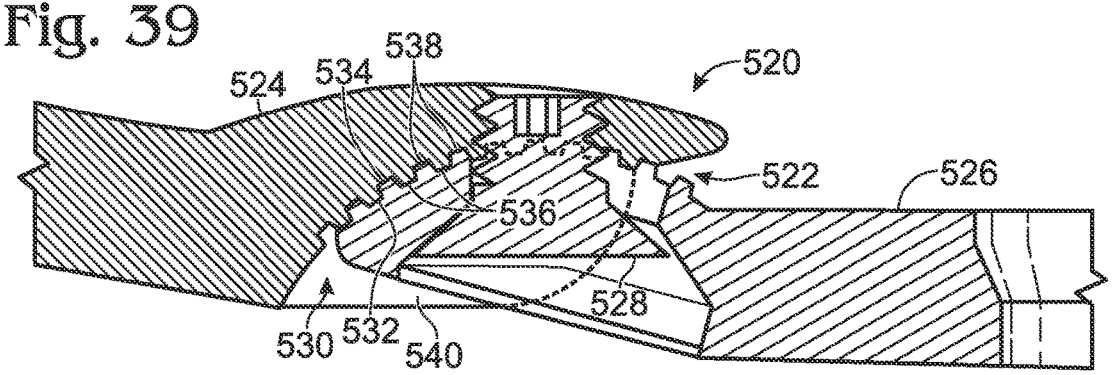
FIG. 39 is a fragmentary, sectional view of the bone plate of FIG. 37, taken generally along line 39-39 of FIG. 37 through the cylindrical joint.

FIGS. 37-39 show an exemplary bone plate 520 having a generally cylindrical joint 522 at which a head plate member 524 is connected to a shaft plate member 526 with an inverted lock screw 528. Joint 522 permits movement of plate members 524 and 526 relative to one another about a rotation axis that is below the bone plate and at least generally parallel to a plane defined by the bone plate and/or a plate member thereof (and optionally at least generally parallel to a width axis of the bone plate). Stated differently, joint 522 permits movement of the plate members relative to one another in a plane that is at least generally parallel to the long axis of the bone plate and transverse (e.g., orthogonal) to a plane defined by the bone plate or at least one of the plate members thereof.

Head plate member 524 may define a receiving space 530, at an end region of the plate member and on an inner side thereof, to receive an end region of shaft plate member 526 (see FIG. 39). Each of the end regions may define complementary joint surfaces 532, 534 that are each generally cylindrical. The joint surfaces may define surface features, such as complementary sets of teeth 536, 538 that fit together in a plurality of different registers. Each register represents a different, discrete angular adjustment of the plate members relative to one another about the rotation axis of the joint. Transverse motion of the plate members relative to one another at the joint, when the joint is in a movable configuration, may be restricted by a pair of flanges 540, 542 of the head plate member that bracket the end region of the shaft plate member (or vice versa) (see FIGS. 37 and 39).

Figure 40:
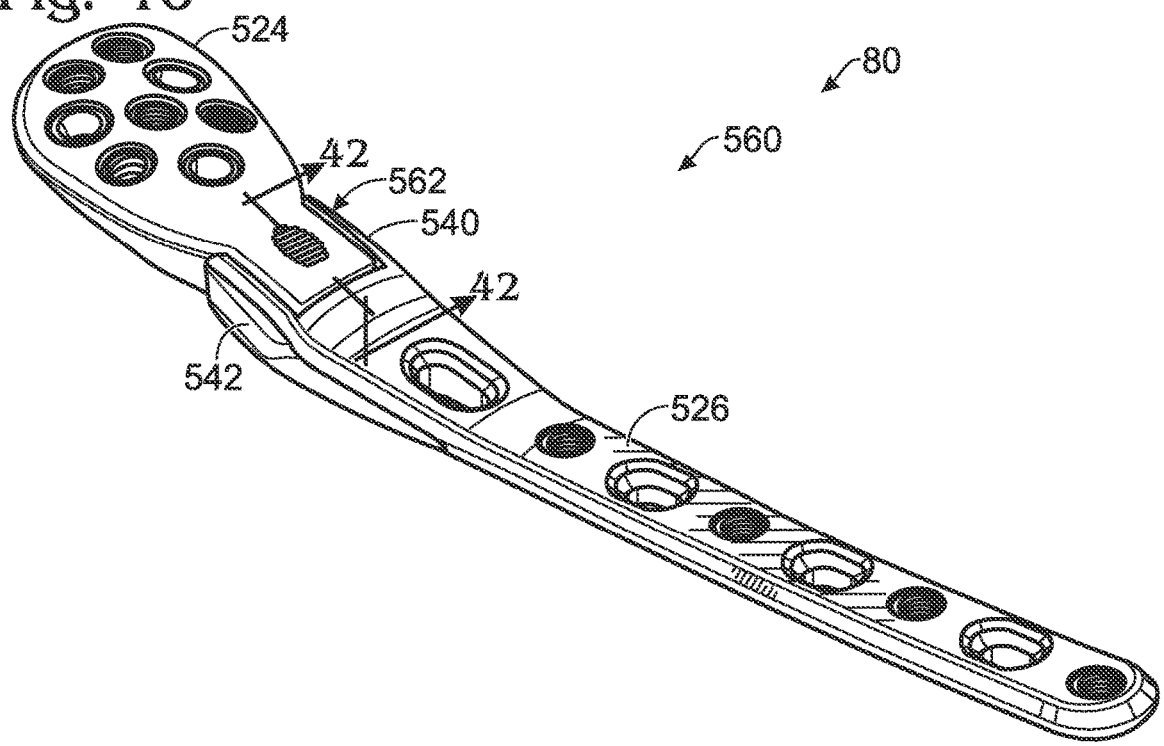
FIG. 40 is a view of another exemplary bone plate having a generally cylindrical joint, taken from above the bone plate, with the curvature of the joint inverted relative to the bone plate of FIG. 37, and with the connector of the joint removed.
Figure 41:
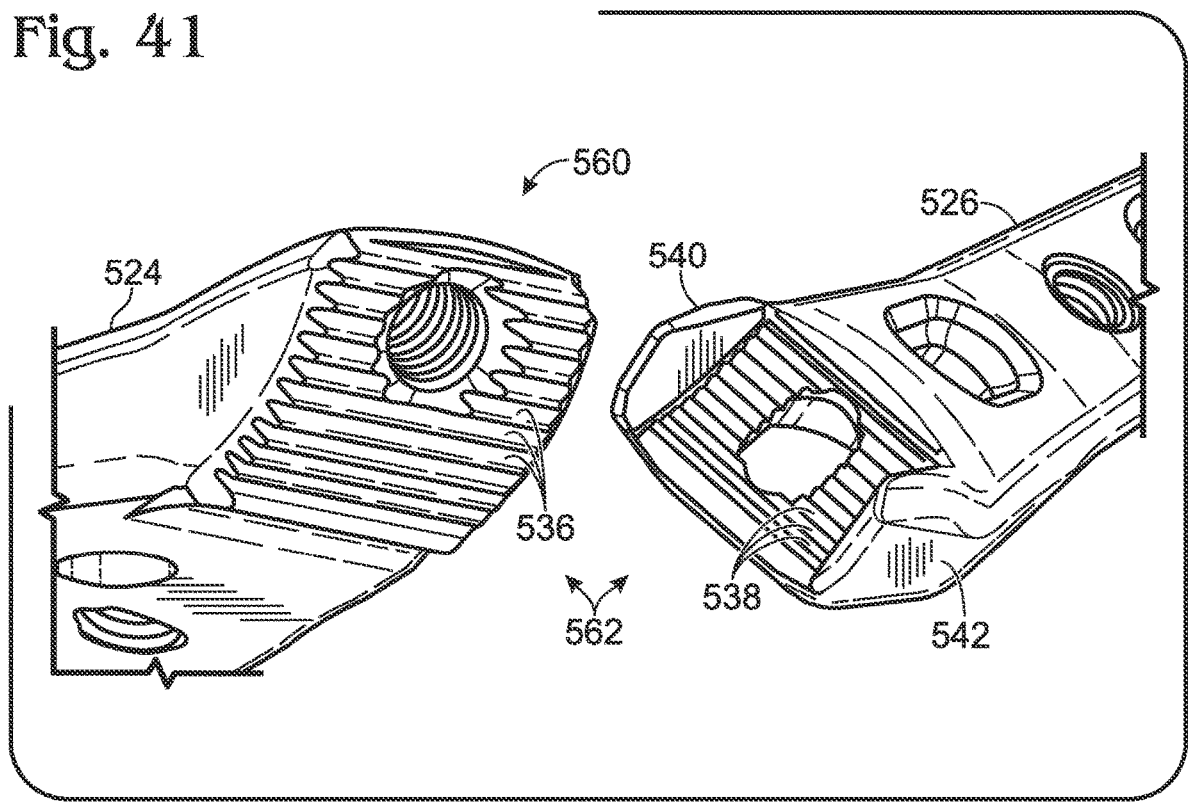
FIG. 41 is a fragmentary, exploded view of the bone plate of FIG. 40, taken around the generally cylindrical joint and with the plate members rotated relative to one another such that both joint surfaces of the plate members are visible.
Figure 42:
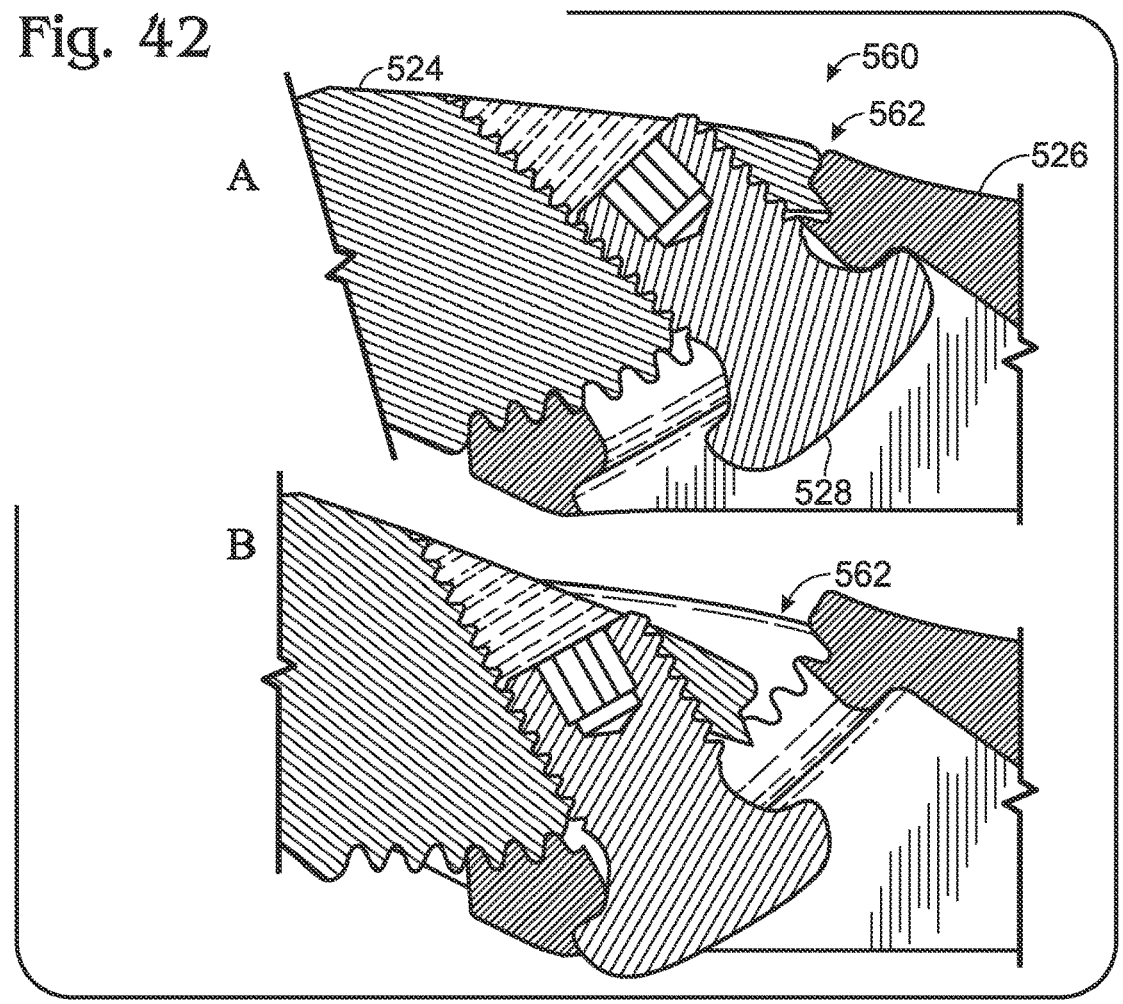
FIG. 42 is a pair of fragmentary, sectional views of the bone plate of FIG. 40, taken generally along line 42-42 of FIG. 40 in the presence of the connector for the generally cylindrical joint and illustrating two different orientations of the plate members in panels A and B, with the orientations produced by inter-fitting joint surfaces together in different registers of complementary surface features.

FIGS. 40-42 show another bone plate 560 have a generally cylindrical joint 562. Bone plate 560 is similar to bone plate 520 except that joint 562 is curved in an opposite direction from joint 522 of bone plate 520. Elements and features of bone plate 560 corresponding to those of bone plate 520 are labeled with the same reference numbers used for bone plate 520.

Figure 43:
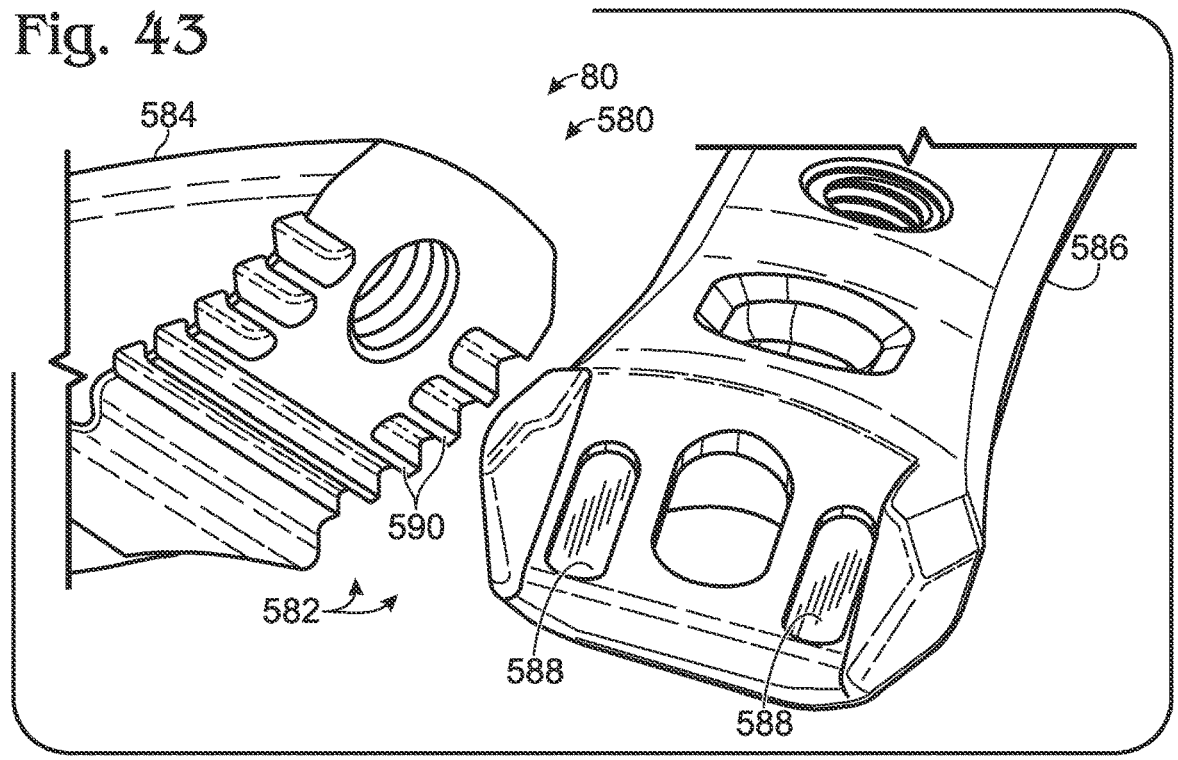
FIG. 43 is an exploded, fragmentary view of yet another exemplary bone plate having a generally cylindrical joint, taken generally as in FIG. 41, with the joint utilizing deformable elements in place of teeth to prevent movement of the plate members relative to one another in the fixed configuration of the joint, in accordance with aspects of the present disclosure.

FIG. 43 shows a bone plate 580 having a generally cylindrical joint 582 at which a head plate member 584 is connected to a shaft plate member 586 by a threaded connector (not shown). The plate members may be constructed generally as described above for bone plates 520 and 560 (see FIGS. 37-42). However, joint 582 may be continuously adjustable, rather than discretely adjustable. The joint may rely on deformation of at least one of the joint surfaces, to prevent slippage of the locked joint, and may have any of the features described above in Section III for multi-axis joints. Accordingly, the teeth present in the joints of bone plates 520 and 560 may be replaced by one or more deformable elements (anti-slip elements), which may protrude into voids 590 defined by the joint surface of plate member 584, when the joint is locked.

V. BONE PLATES WITH JOINTS TO ADJUST TRANSLATIONAL OFFSET

Figure 44:
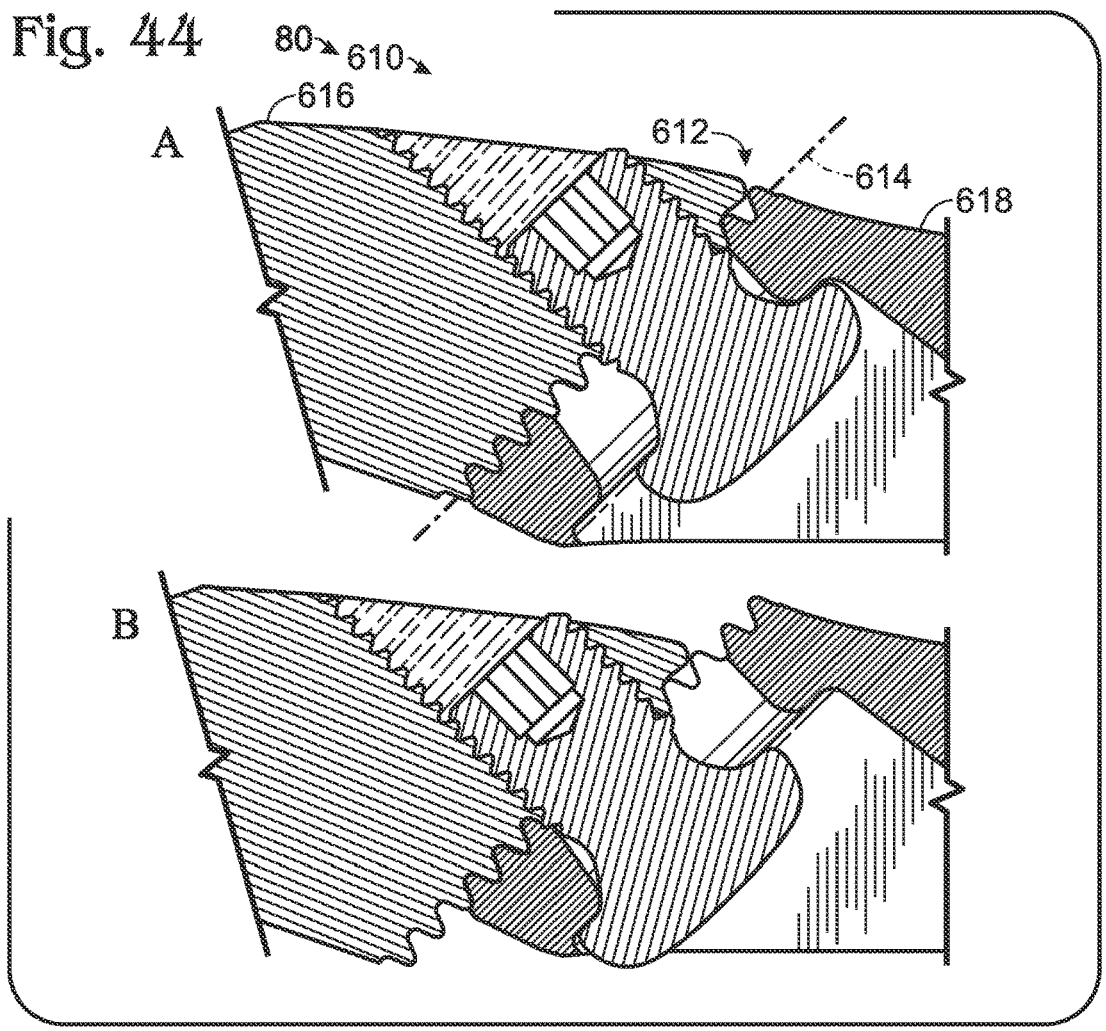
FIG. 44 is a pair of fragmentary, sectional views of an exemplary bone plate having a generally planar joint that permits translational adjustment of plate member positions relative to one another, taken generally as in FIG. 42 and illustrating two different positions of the plate member in panels A and B produced by inter-fitting joint surfaces together in different registers of complementary surface features.

This section describes an exemplary bone plate 610 having a joint 612 that permits plate members to be displaced relative to one another in a plane 614 without substantially changing their orientations relative to one another; see FIG. 44.

Bone plate 610 may have a pair of plate members, such as a head plate member 616 connected to a shaft plate member 618. Joint 612 may include complementary teeth that allow discrete adjustment of the plate members at the joint. Bone plate 610 may have any of the features of other bone plates of the present disclosure and may be most similar to bone plate 560 (see FIGS. 40-42), but modified to have a generally planar joint rather than a generally cylindrical joint.

VI. METHODS OF BONE FIXATION

This section describes exemplary methods of fixing bone using any of the bone plates disclosed herein. The steps presented in the section may be performed in any suitable order and combination, and may be modified by or combined with any of the other procedures and features disclosed elsewhere herein.

At least one bone to be fixed may be selected. The bone(s) may be any suitable bone(s) of a vertebrate species, such as an arm bone (e.g., a humerus, ulna, or radius), a leg bone (e.g., a femur, tibia, or fibula), a hand/wrist bone (e.g., a carpal, metacarpal, or phalange), a foot/ankle bone (e.g., a tarsal, metatarsal, calcaneus, or phalange), a rib, a sternum, a scapula, a clavicle, a pelvis, a cranial bone, a facial bone, a vertebra, or the like, or any combination thereof of adjacent bones. The bone may have any suitable discontinuity or structural weakness, such as at least one fracture, at least one cut, a nonunion, or the like, or two or more adjacent bones may be selected to be fused to one another.

An incision may be created through overlying soft tissue to access the selected at least one bone. The selected bone may be manipulated to reposition bone fragments (e.g., to approximate the relative anatomical location of the fragments), such as to set a fracture. Manipulation of bone fragments (or two or more selected bones) may be performed before or after the incision is created.

A bone plate may be selected for stabilizing the selected bone. The bone plate may have at least two plate members connected by at least one movable joint as disclosed herein.

The bone plate may be placed through the incision and onto the selected bone. The incision may be at least about a long as or shorter than the bone plate.

The bone plate may be attached to the bone with fasteners, such as bone screws, placed into one or more through-holes of each plate member and extending into the bone.

The rotational and/or translational position of the plate members relative to one another may be adjusted before and/or after the bone plate is attached to the bone. Adjustment may be performed with a joint of the bone plate in a movable configuration that permits movement of the plate members relative to one another. The bone plate may be placed in a fixed configuration after the adjustment, to fix the positions of the plate members relative to one another. The incision then may be closed.

Bone plates with single-axis or multi-axis joints may be adjusted at different times during a bone fixation procedure. The longitudinal shape of a hinged bone plate having one or more hinge joints may be adjusted fully before the bone plate is attached to the bone, or at least before each plate member is attached to the bone. In some cases, the orientation of first and second plate members connected by a hinge joint may be adjusted after attaching the first plate member to bone and before attaching the second plate member to bone. The second plate member may be rotated relative to the first plate member, to a desired orientation, and then the second plate member may be attached to the bone. If the hinged bone plate has three or more plate members, this process may be performed again for each additional plate member before the plate member is attached to the bone. In other words, the plate members of the hinged bone plate may be successively aligned with the bone and then attached. The orientation of plate members of a bone plate having a multi-axis joint may be adjusted after the plate members are attached to different pieces of bone, to change the orientation of the pieces of bone (e.g., to improve fracture reduction).

VII. EXAMPLES

The following examples describe selected aspects and embodiments of the present disclosure related to bone plates with movable joints. These examples are included for illustration and are not intended to limit or define the entire scope of the present disclosure.

Figure 47:
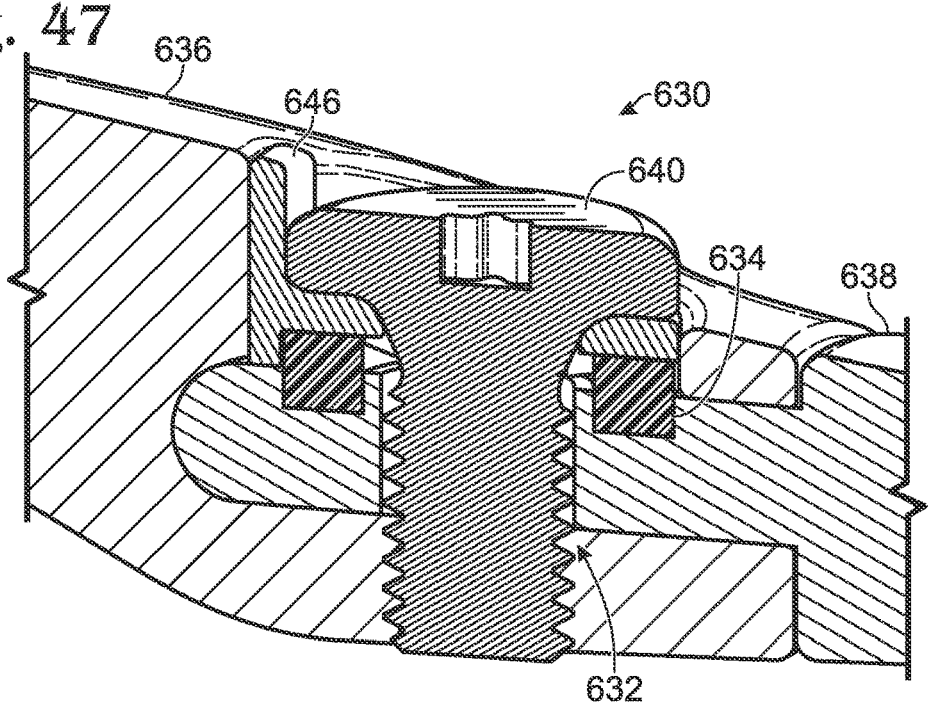
FIG. 47 is a sectional view of the bone plate of FIG. 45, taken generally along line 47-47 of FIG. 46.
Figure 46:
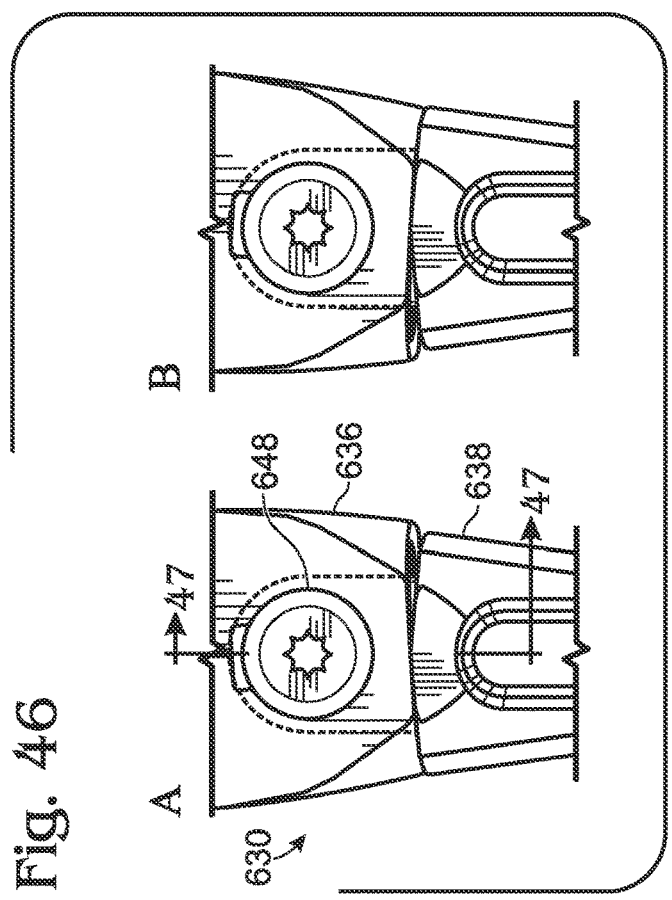
FIG. 46 is a pair of fragmentary plan views of the bone plate of FIG. 45, taken generally around the hinge joint and illustrating two different orientations of the plate members of the bone plate in panels A and B.
Figure 45:
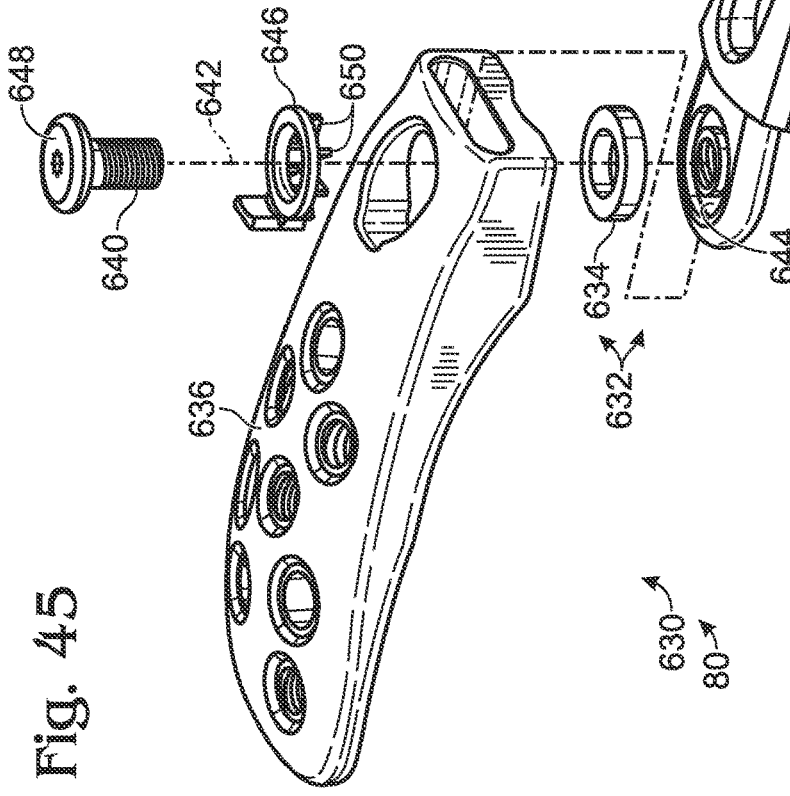
FIG. 45 is an exploded view of an exemplary bone plate including a lockable hinge joint having a rotation axis arranged transverse to a plane defined by the bone plate, with the hinge joint including a deformable element, in accordance with aspects of the present disclosure.
Figure 48:
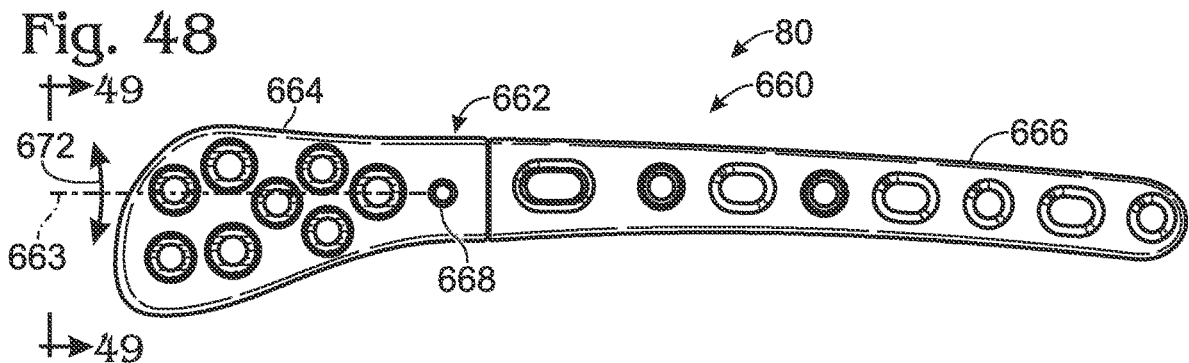
FIG. 48 is a plan view of an exemplary bone plate including a generally cylindrical joint having a rotation axis arranged at least generally parallel to a long axis defined by the bone plate, in accordance with aspects of the present disclosure.

Example 1. Exemplary Bone Plate with a Hinge Joint Having a Deformable Element This example describes an exemplary bone plate 630 that includes a hinge joint 632 having a deformable element 634 to facilitate locking the joint; see FIGS. 45-47.

Bone plate 630 may have a head plate member 636 connected to a shaft plate member 638 by a lock screw 640. Hinge joint 632 may be adjustable about a pivot axis 642 that is coaxial with lock screw 640.

Deformable element 634 may be positioned to be compressed by adjustment of lock screw 640. The deformable element may be disposed in a recess 644 defined by shaft plate member 638. A washer 646 may be located between a head 648 of the lock screw and a top side of deformable element 634. The washer may have radial teeth 650 that contact the top side of the deformable element. As the lock screw is tightened, the teeth may bite into the deformable element to fix the angular position of the plate members.

Further aspects of hinge joints and deformable elements are described elsewhere in the present disclosure, such as in Sections II and III and in Examples 3 and 4, among others.

Example 2. Exemplary Bone Plates with a Longitudinal Rotation Axis

This example describes exemplary bone plates including a generally cylindrical joint that permits angular adjustment of plate members relative to one another about an axis that is at least generally parallel to the long axis of the bone plate; see FIGS. 48-53.

FIGS. 48-52 show an exemplary bone plate 660 having a generally cylindrical joint 662 with a rotation axis 663 arranged at least generally parallel to a long axis defined by the bone plate (e.g., within about 20, 10, or 5 degrees of parallel, among others). Bone plate 660 has a head plate member 664 connected to a shaft plate member 666 by a connector 668 that determines whether the joint is in a movable or a fixed configuration. Joint 662 permits the orientation of the plate members to be adjustable continuously in a plane transverse to the long axis of the bone plate.

Figure 49:
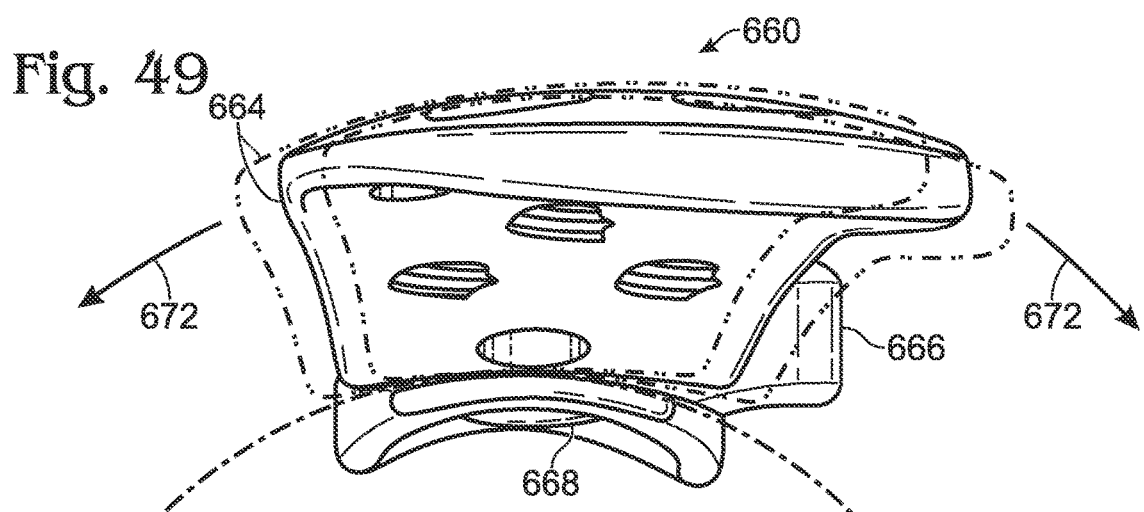
FIG. 49 is an end view of the bone plate of FIG. 48, taken generally along line 49-49 of FIG. 48 and illustrating phantom movement of pieces of the plate relative to one another about the rotation axis.
Figure 50:
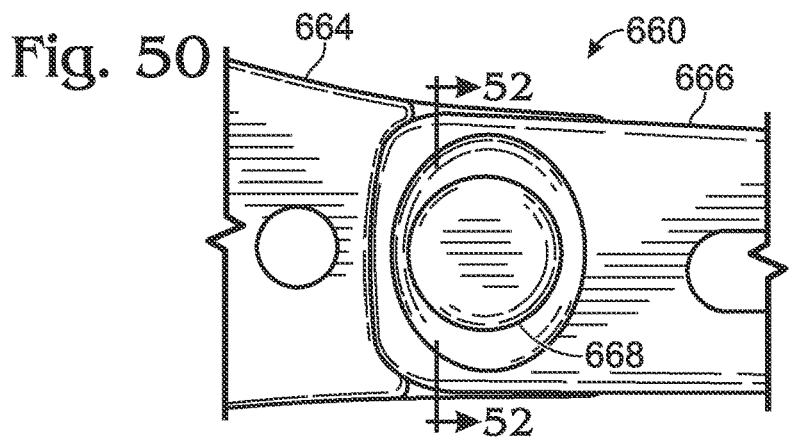
FIG. 50 is a fragmentary, bottom view of the bone plate of FIG. 48, taken generally around the cylindrical joint.

FIG. 49 is an end view of bone plate 660 illustrating phantom movement of head plate member 664 relative to shaft plate member 666. The head plate member is movable in either rotational direction, indicated by arrows at 672.

Figure 51:
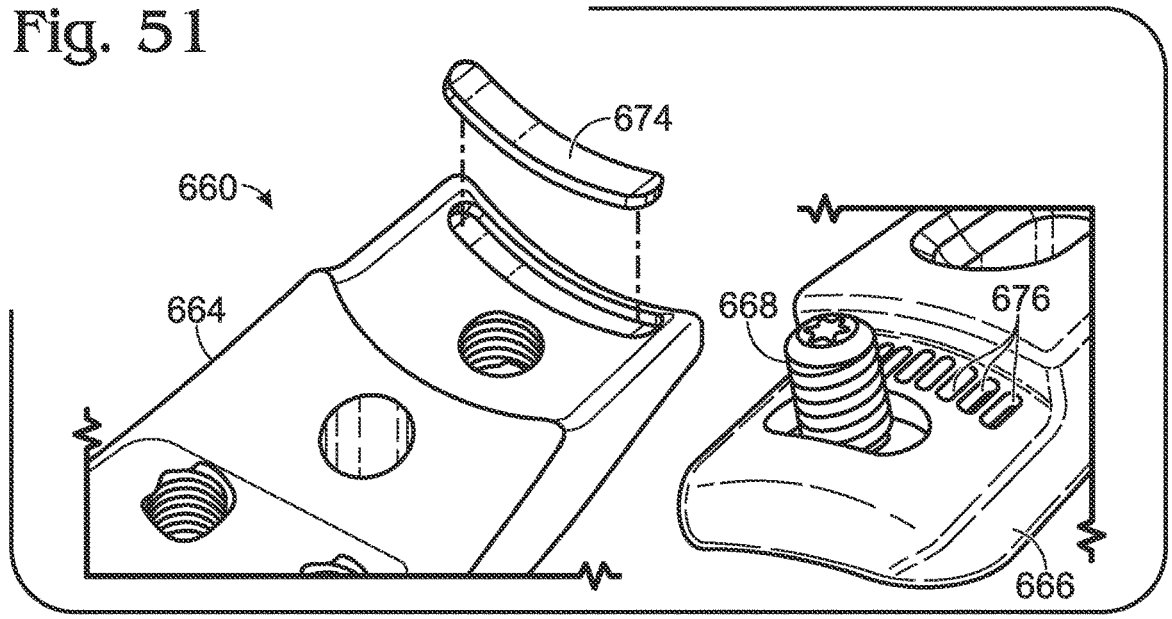
FIG. 51 is a fragmentary, exploded view of the bone plate of FIG. 48, taken generally around the cylindrical joint with a head plate member inverted with respect to a shaft plate member of the bone plate.
Figure 52:
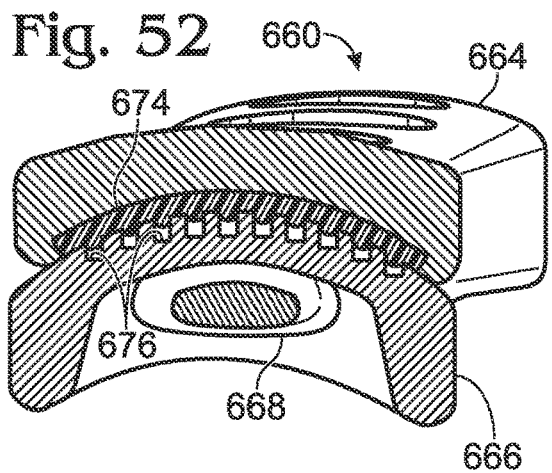
FIG. 52 is a sectional view of the bone plate of FIG. 48, taken generally along line 52-52 of FIG. 50 through the cylindrical joint.

FIGS. 51 and 52 show further aspects of joint 662. At least one deformable element 674 may be located in a recess defined by head plate member 664, to form part of the joint surface of the head plate member. The deformable element projects from the recess toward the joint surface of shaft plate member 666. The deformable element is deformed as the joint is locked by turning connector 668, and enters voids 676 defined by the joint surface of shaft plate member 666 (see FIG. 52). Deformable element 674, the recess, and/or voids 676 may be arranged in a plane parallel to the plane in which the plate members rotate. Bone plate 660 may have any combination of the features described elsewhere herein, such as above in Section III and below in Example 4, among others.

Figure 53:
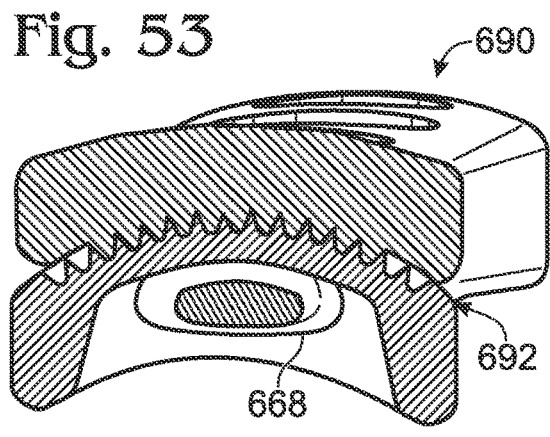
FIG. 53 is a sectional view of another exemplary bone plate having a generally cylindrical (single-axis) joint oriented generally as in the bone plate of FIG. 48, with the cylindrical joint having complementary surface features defined by a pair of joint surfaces and configured to fit together in a plurality of discrete registers, in accordance with aspects of the present disclosure.

FIG. 53 shows another exemplary bone plate 690 having a generally cylindrical joint 692. Bone plate 690 may be structured the same as bone plate 660 of FIGS. 48-52, except that joint 692 is discretely adjustable through the mating of complementary surface features (teeth in the depicted embodiment) that fit together in a plurality of different registers, each producing a discrete angular change in the orientation of the plate members relative to one another.

Example 3. Exemplary Hinge Joints and Associated Plate Structure

This example describes exemplary bone plates each including one or more hinge joints connecting two or more plate members; see FIGS. 54-71. The features of the bone plates and hinge joints described in this example may be combined with one another and/or with any of the elements and features described elsewhere in the present disclosure, such as in Sections I and II, and in other examples of this section, among others.

Figure 54:
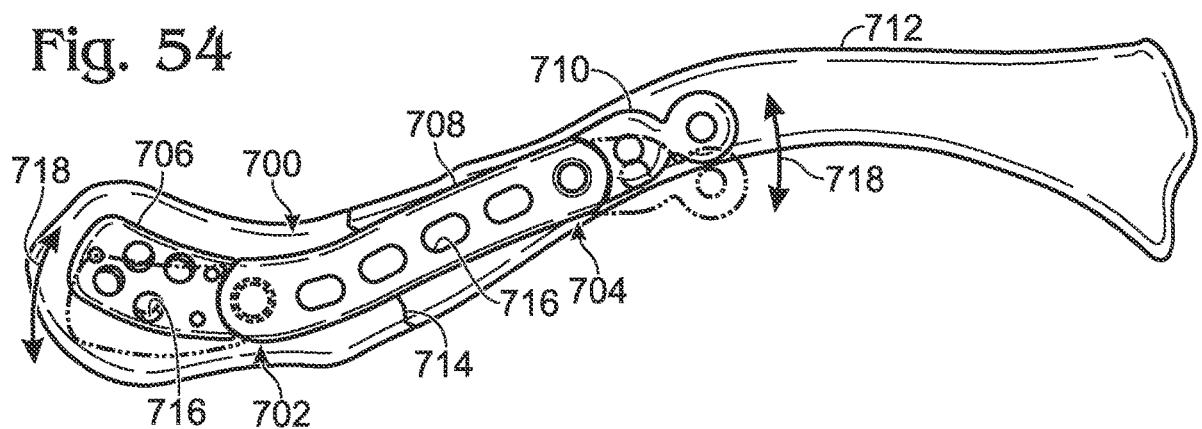
FIG. 54 is a plan view of an exemplary bone plate having a closed (non-cannulated) hinge joint and an open (cannulated) hinge joint connecting three plate members to one another end-to-end, with the bone plate positioned on a lateral region of a clavicle before attachment with fasteners (such as bone screws), and with in-plane rotational motion of the two end plate members shown in phantom, in accordance with aspects of the present disclosure.
Figure 55:
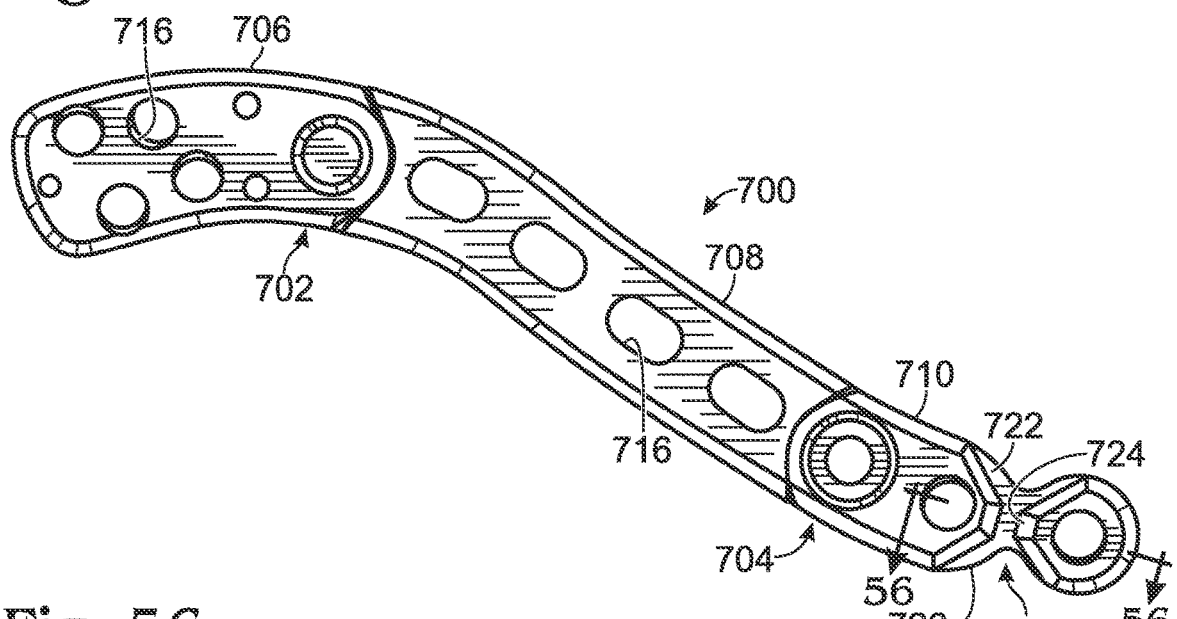
FIG. 55 is a bottom view of the bone plate of FIG. 54, taken in the absence of the clavicle.
Figure 56:
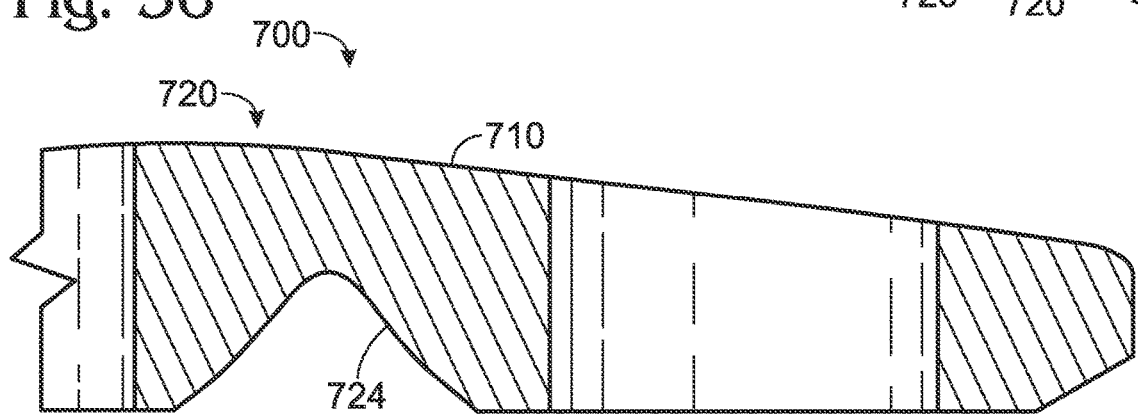
FIG. 56 is a fragmentary sectional view of the bone plate of FIG. 54, taken generally along line 56-56 of FIG. 55 through an end region of the bone plate and showing a notch formed in a bottom surface of the bone plate to enable out-of-plane deformation of the end region.

FIGS. 54-56 show an exemplary bone plate 700 having a closed (non-cannulated) hinge joint 702 and an open (cannulated) hinge joint 704 connecting three plate members 706, 708, and 710 to one another end-to-end. In FIG. 54, bone plate 700 is positioned on a clavicle 712 having at least one fracture 714, before attachment of the bone plate to the clavicle with fasteners (such as bone screws) extending into the clavicle from circular and oblong through-holes 716 of the bone plate. The through-holes may have different sizes, such as smaller holes (e.g., in most-lateral plate member 706) to receive wires or pins, and larger through-holes to receive bone screws. One of the through-holes is coaxial to the pivot axis of open hinge joint 704. (Closed hinge joint 702 cannot receive a fastener extending into bone.) Each of plate members 706 and 710 is rotatable in-plane with respect to central plate member 708, indicated by rotation arrows 718 in FIG. 54, to customize the longitudinal shape of the bone plate to follow the clavicle (or other elongated bone).

Clavicle 712 is shown with the acromial extremity (the lateral end) on the left and the sternal facet (the medial end) on the right. The bone plate can be positioned at any suitable location along the clavicle, such as near the lateral end of the clavicle in the depicted embodiment.

FIGS. 55 and 56 show respective bottom and sectional views of bone plate 700. One or both end plate members 706 and 710 may have a selectively deformable region 720 created at least in part by a recess 722 formed in a bottom surface of the plate member. The recess may taper as it extends toward a transverse midpoint of the plate member from opposite edges thereof, to form a central notch 724. The recess may be formed at a narrowed region 726 of the plate member created by aligned indentations defined by opposite edges of the plate member. Deformable region 720 provides a site at which the plate member can be selectively deformed out-of-plane (bent and/or twisted), such that the plate member more closely follows the contour of an underlying bone.

Figure 57:
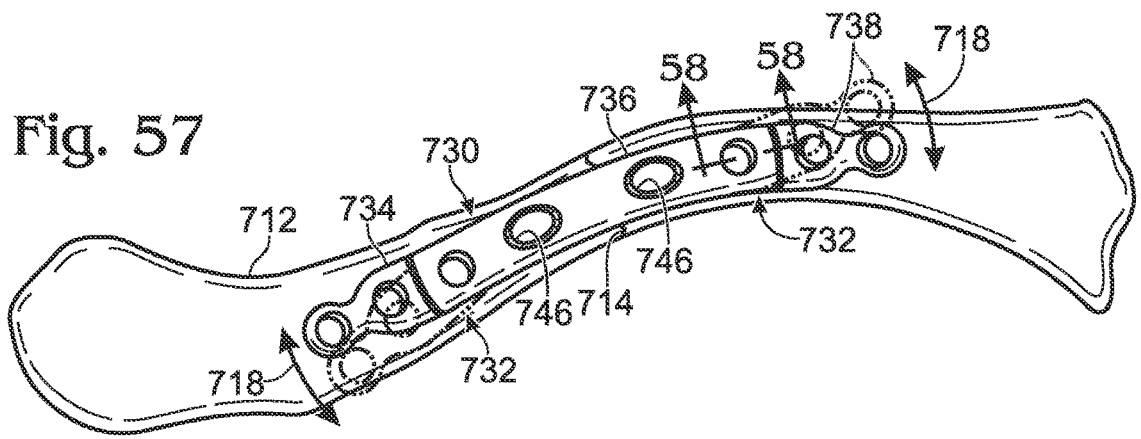
FIG. 57 is a plan view of an exemplary bone plate having a pair of open hinge joints connecting three plate members to one another end-to-end, with the bone plate positioned on a longitudinally central region of a clavicle before attachment with fasteners, with pivotal motion of the two end plate members shown in phantom, and with each hinge joint being formed only by integral portions of a pair of adjacent plate members, in accordance with aspects of the present disclosure.
Figure 58:
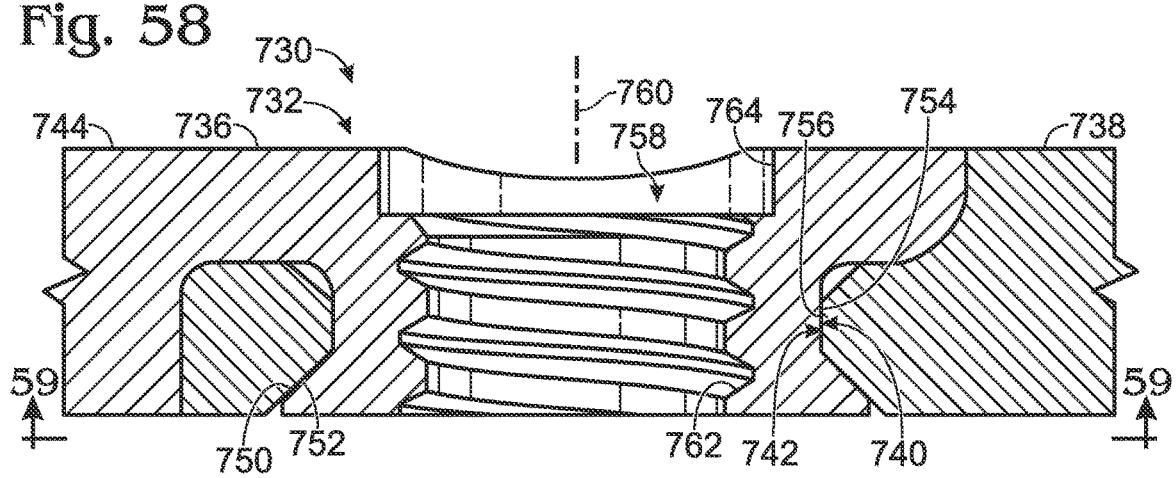
FIG. 58 is a fragmentary sectional view of the bone plate of FIG. 57, taken generally along line 58-58 of FIG. 57 through one of the hinge joints.
Figure 59:
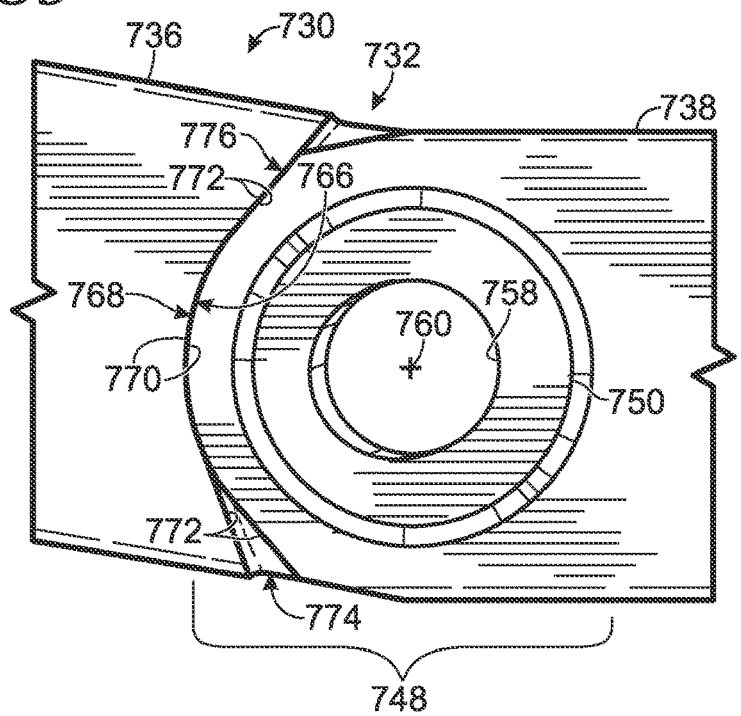
FIG. 59 is a fragmentary bottom view of the bone plate of FIG. 57, taken generally along line 59-59 of FIG. 58 toward one of the hinge joints.

FIGS. 57-59 show an exemplary bone plate 730 having a pair of open hinge joints 732 connecting three plate members 734, 736, and 738 to one another end-to-end. In FIG. 57, the bone plate is positioned more centrally along clavicle 712 than bone plate 700 of FIG. 54. Rotational motion of plate members 734 and 738 with respect to central plate member 736 is shown in phantom indicated with motion arrows at 718.

Bone plate 730 is similar to bone plate 120 of FIGS. 2-6 and may have any combination of features described above for bone plate 120 (see Section II), among others. For example, the resistance to pivotal motion of each hinge joint 732 may be configured not to be user-adjustable at the hinge joint, such as not adjustable between configurations that are movable and fixed off bone (or one bone). Instead, each hinge joint 732 may have an intrinsic resistance (e.g., frictional resistance) to pivotal motion that is configured not to vary substantially as the bone plate is manipulated and installed.

Hinge joint 732 is formed by an axle 740 of plate member 736 captured in an aperture 742 of plate member 738. Axle 740 is formed integrally with a body 744 of plate member 736, where the body defines one or more through-holes 746 outside a region of overlap 748 of the plate members with one another (see FIGS. 57-59). A retainer 750 (also called a retaining portion) for axle 740 is larger in diameter than the minimum diameter of aperture 742, which prevents removal of the axle from the aperture, and permanently connects the plate members to one another. The retainer may be formed integrally with the axle, fused to the axle by welding, created by 3D printing both plate members together in a connected configuration, or the like.

Friction between axle 742 and plate member 738 prevents the plate members from rotating freely relative to one another. Plate members that cannot rotate freely relative to one another require application of force greater than the torque generated by gravity to generate rotation. The torque generated by gravity is determined with the pivot axis and the long axis of the bone plate both horizontal, and with the plate member of smaller mass held stationary.

Frictional resistance to rotation may, for example, be created by tightly engaging axle 740 with a wall of aperture 742. For example, wider retainer 750 may be tightly engaged with the wall of an end region 752 of aperture 742, such as by swaging, during manufacture of the bone plate. End region 752 may have a diameter (e.g., a minimum or average diameter) that is greater than the minimum diameter of aperture 742. Here, end region 752 is tapered, such as conically tapered, but may be cylindrical, among others. In other embodiments, a cylindrical region 754 of axle 740 may engage a wall region 756 of aperture 742 to provide a majority of the frictional resistance to rotation.

The resistance (e.g., frictional resistance) to rotation at each hinge joint may be set during manufacture of the bone plate, such as when retainer 750 is created. In some embodiments, the resistance may be determined by deformation of the axle. The resistance may require a torque of at least about 1, 2, or 5 inch-pounds, or at least about 1, 2, 5, or 10 foot-pounds, among others, to rotate the plate members relative to one another. In some embodiments, the resistance may be set such that one or more tools are advantageous and/or required to provide a mechanical advantage to rotate the plate members (see below), while the bone plate is off and/or on bone. In other words, the plate members may not be rotatable by hand without the use of at least one tool.

Hinge joint 732 is an open joint defining a through-hole 758 extending along a pivot axis 760 defined by axle 740. Through-hole 758 may (or may not) have an internal thread 762 to attach a fastener, such as a bone screw, to the wall of the through-hole. In other examples, a fastener may be placed into bone from through-hole 758 without attachment to the wall of the through-hole. The through-hole may have a wider region, such as a counterbore 764, formed at the entry end to receive a head of the fastener. The presence of a through-hole arranged on the pivot axis of the joint offers various advantages. For example, the bone plate can be attached to bone more securely. Also, the spacing of through-holes (and thus installed fasteners) along the bone plate can be more uniform.

FIG. 59 shows respective concave and convex walls 766, 768 of joint 732 that determine an angular range of motion for the plate members through contact with one another that blocks further rotation. Each wall has a circular region 770 and a pair of linear regions 772 extending tangentially from opposite ends of the circular region. The circular regions may have the same radius of curvature. However, the circular region of convex wall 768 formed by plate member 738 is longer than the circular region of concave wall 766 formed by plate member 736. The plate members can be rotated in either rotational direction until the linear wall regions on one end of the circular regions are abutted with one another. A tapered gap 774 is formed between the linear regions on only one or both ends of the circular regions when the plate members are respectively intermediate or at the two stopped positions at the opposite extremes of the rotational range of rotation. In the depicted embodiment, plate member 738 has been rotated counterclockwise (and/or plate member 736 clockwise) to a stopped position at which the linear wall regions on one end of the circular regions are abutted, indicated by an arrow at 776. Each plate member may have any suitable range of motion, such as at least about 5, 10, 15, or 20 degrees, and/or less than about 60, 40, or 30 degrees, among others.

Figure 60:
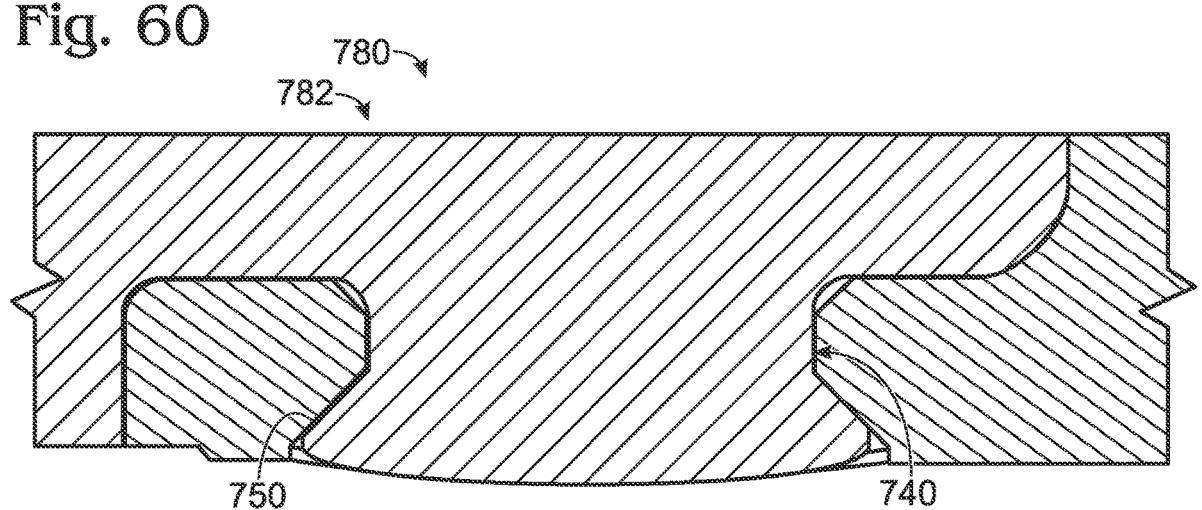
FIG. 60 is a fragmentary sectional view of a bone plate having a closed counterpart of the open hinge joint of FIG. 58, taken generally as in FIG. 58 through the hinge joint, in accordance with aspects of the present disclosure.

FIG. 60 shows a bone plate 780 having a closed hinge joint 782. Hinge joint 782 is similar to open hinge joint 732 of bone plate 730 (see FIG. 58), except for the absence of through-hole 758 and a protruding shape for retainer 750.

Figure 61:
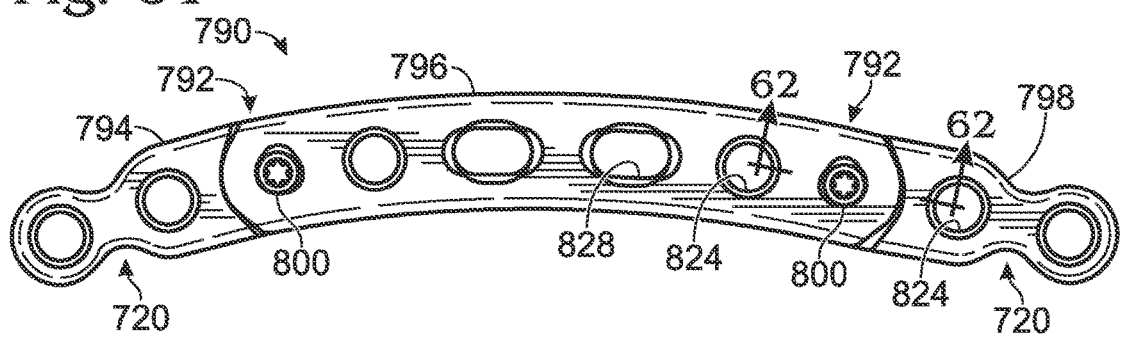
FIG. 61 is a plan view of an exemplary bone plate having a pair of closed hinge joints connecting three plate members end-to-end, with each hinge joint including a connector having an external thread, in accordance with aspects of the present disclosure.

FIG. 61 shows an exemplary bone plate 790 having a pair of closed hinge joints 792 connecting three plate members 794, 796, and 798 end-to-end. Each hinge joint includes a connector 800 that connects a pair of the plate members to one another in a region of overlap where the plate members overlap one another.

Figure 62:
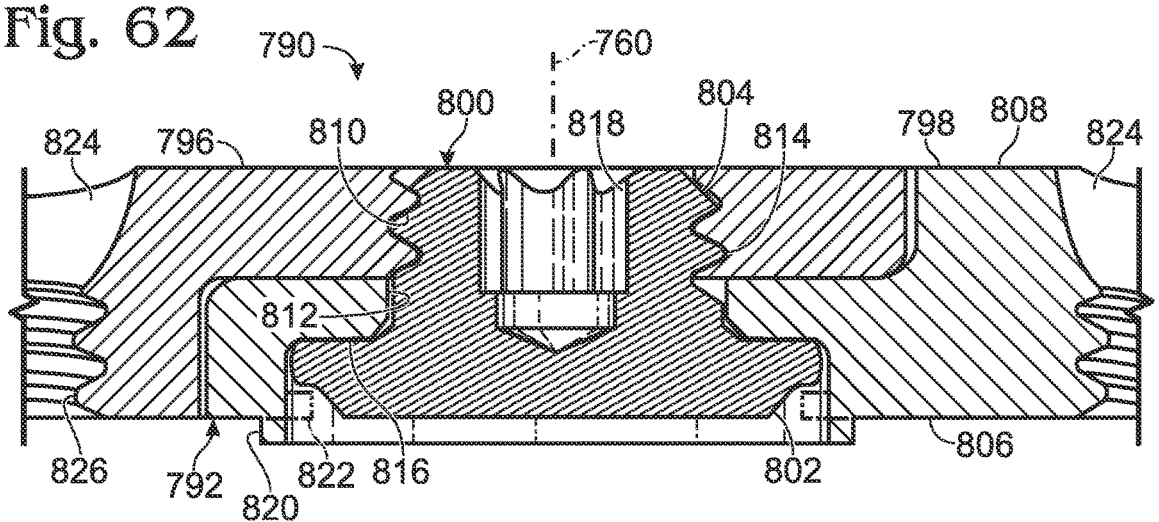
FIG. 62 is a fragmentary sectional view of the bone plate of FIG. 61, taken generally along line 62-62 of FIG. 61 through one of the hinge joints.

FIG. 62 shows a sectional view of bone plate 790 taken through one of the hinge joints. Connector 800 is a threaded member (a screw) having an inverted configuration, with a head 802 below a shaft 804, when the bone plate is oriented with an inner, bone-contacting surface 806 of the bone plate facing down (as in FIG. 62). In other words, head 802 is closer to inner surface 806 and shaft 804 is closer to an outer surface 808 of the bone plate.

The connector is received in a pair of aligned apertures 810, 812 of plate members 796, 798. Shaft 804 has an external thread 814 that attaches to an internal thread in aperture 810 of plate member 796. Head is received in a wider region (a counterbore) of aperture 812 and abuts a shoulder 816 defined by the aperture.

Connector 800 has a driver interface, such as an opening 818, for mating with a complementary working end of a driver. The opening extends into the shaft from an end thereof. Opening 818 is accessible from above the bone plate and allows the driver to turn the connector, to adjust the joint between movable and fixed configurations. Since connector 800 is inverted, external thread 814 may be left-handed to provide the conventional directions of rotation for tightening and loosening a threaded member. In other words, from the perspective of a surgeon above the bone plate, rotating the connector clockwise compresses the plate members from a movable configuration of the joint to produce a fixed configuration, and rotating the connector counterclockwise from a fixed configuration of the joint reduces compression of the plate members to produce a movable configuration of the joint. In other embodiments, opening 818 may be replaced by an external driver interface, such as facets, among others.

Plate member 798 is created with a flange 820 projecting (e.g., orthogonally) from an inner surface of the plate member, in a direction away from the outer surface of the plate member. The flange initially does not extend into aperture 812 and/or obstruct placement of connector 800 into aligned apertures 810, 812. However, after the hinge joint has been assembled, flange 820 can be deformed by rolling the flange radially inward, indicated in phantom at 822, to a configuration that obstructs travel of the connector's head 802 out of aperture 812 along pivot axis 760. With the flange preventing removal of connector 800, plate members 796 and 798 are permanently connected to one another, because connector 800 cannot be removed from hinge joint 792 (without damaging bone plate 790). The flange also may provide a stop that limits how much the connector (and thus the hinge joint) can be loosened. The stop thus helps the surgeon to avoid placing the joint in a freely movable configuration in which the bone plate becomes excessively flexible. Any of the bone plates disclosed herein, including bone plates with multi-axis joints, may include a flange 822 near or at an outer surface or an inner surface of a plate member, to obstruct removal of a connector from the bone plate, such that plate members are permanently connected to one another.

Plate members 796 and 798 overlap one another in a half-lap configuration. Accordingly, in the depicted embodiment, the plate members do not mate with one another through mating features (e.g., an end region or flange of one plate member received in a track formed by the other plate member). Connector 800 prevents this translational separation. In other embodiments, as described below, the plate members may include complementary mating features that facilitate (a) mating the plate members with one another, (b) aligning a pair of apertures of the plate members, (c) retaining the plate members adjacent one another before a connector is installed, and/or (d) increasing a bending strength of the bone plate at the joint.

Hinge joint 792, or any other hinge joint disclosed herein, may be located between a pair of circular through-holes 824 and adjacent each of the through-holes (see FIGS. 61 and 62). One or both of the through-holes 824 may have an internal thread 826. In some embodiments, one or both through-holes 824 may be replaced by a slot 828, which may be elongated parallel to the long axis of a plate member that defines the slot (see FIG. 61).

Figure 63:
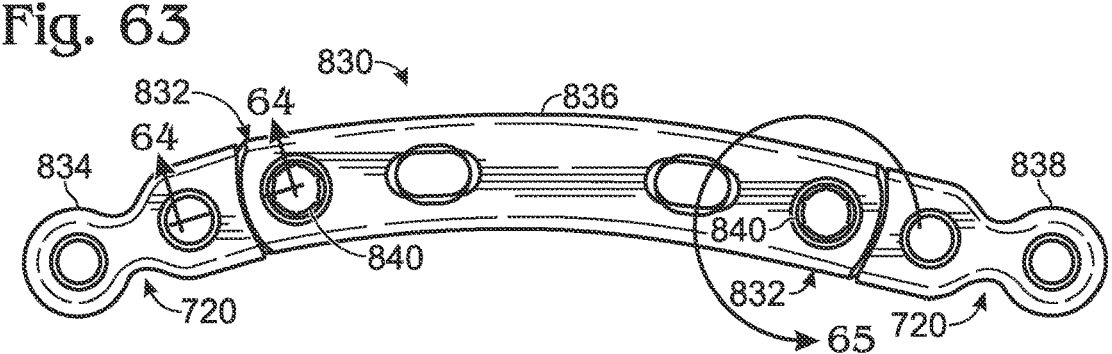
FIG. 63 is a plan view of another exemplary bone plate having a pair of open hinge joints connecting three plate members end-to-end, with each hinge joint including a cannulated connector having an external thread and defining a through-hole to receive a fastener that extends into underlying bone, in accordance with aspects of the present disclosure.
Figure 64:
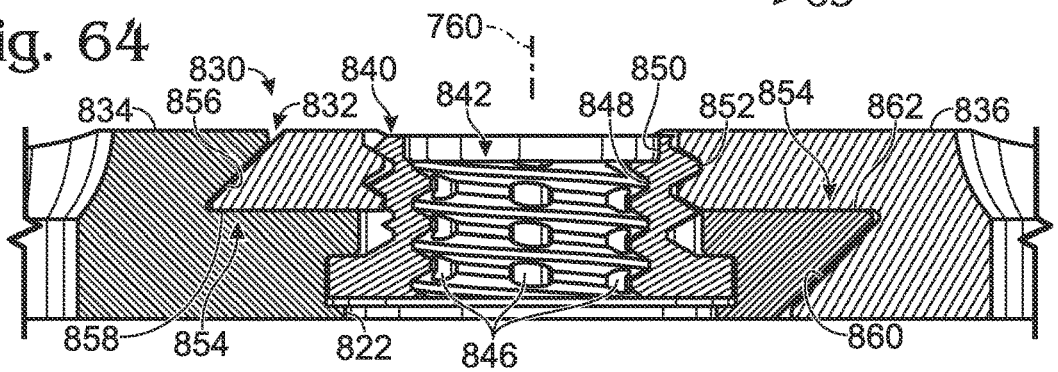
FIG. 64 is a fragmentary sectional view of the bone plate of FIG. 63, taken generally along line 64-64 of FIG. 63 through one of the hinge joints.
Figure 65:
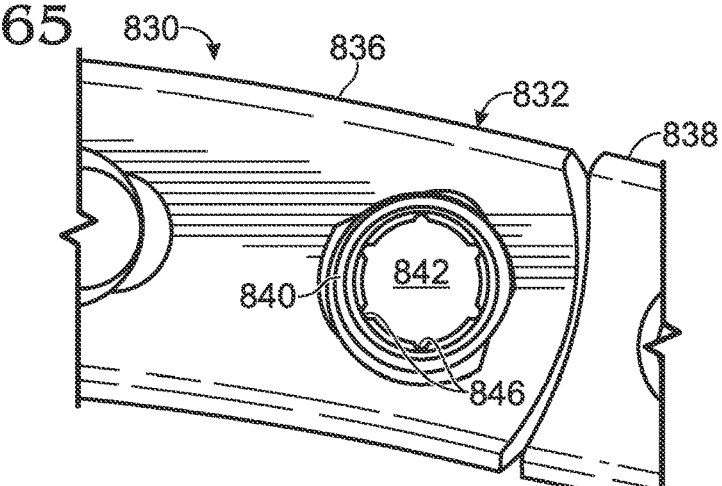
FIG. 65 is a fragmentary plan view of the bone plate of FIG. 63, taken generally around the region indicated at "65" in FIG. 63.

FIGS. 63-65 show an exemplary bone plate 830 having a pair of hinge joints 832 connecting three plate members 834, 836, 838 end-to-end. Bone plate 830 is similar to bone plate 790 and may have any combination of features described for bone plate 790, except that each hinge joint 832 is open rather than closed. Also, the plate members have undercut mating features, as described below.

Hinge joint 832 is considered open because the joint includes a connector 840 defining a through-hole 842 to receive a fastener, such as a threaded fastener (e.g., a bone screw or peg) placed along a pivot axis 760 defined by the connector. Through-hole 842 defines a driver interface that is complementary to the working end of a suitable driver, to allow turning the connector with the driver. In the depicted embodiment, through-hole 842 defines a plurality of axial channels 846 (parallel to pivot axis 760) to receive corresponding axial ridges of a driver. Through-hole 842 has an internal thread 848 for threaded engagement with a fastener, and a counterbore 850 to receive a head of the fastener. Internal thread 848 may be right-handed, and an external thread 852 of connector 840 may be left-handed. Axial channels 846 extend transversely to the internal thread and remove portions thereof. In other embodiments, the through-hole may lack an internal thread.

Connector 840 is prevented from removal by a deformed flange 822 of plate member 834, as described above for bone plate 790 (see FIG. 62). Accordingly, a pair of plate members are permanently connected to one another at each hinge joint.

FIG. 64 shows complementary mating features 854 formed by plate members 834, 836 at a region of overlap. These mating features can increase the bending strength of the bone plate at the joint, relative to a half-lap configuration (see FIG. 62), by spreading out the stress distribution. The mating features may have a partial-dovetail configuration. (See FIGS. 10 and 11 for another configuration.) Each mating feature may be undercut with respect to an inner surface and an outer surface of one of the plate members. More particularly, plate member 834 defines a track 856 (e.g., an arcuate channel) that receives an end region 858 of plate member 836. Track 856 is undercut with respect to the inner and outer surfaces of plate member 834, and end region 858 is undercut with respect to the inner and outer surfaces of plate member 836. Also, plate member 836 defines a track 860 (e.g., an arcuate channel) that receives an end region 862 of plate member 834. Track and end region 860, 862 are undercut with respect to the inner and outer surfaces of plate members 836 and 834, respectively. Each track and end region may be arcuate in a plane orthogonal to the pivot axis, with track 856 and end region 858 having a curvature that is opposite to the curvature of track 860 and end region 862. A line of curvature defined by each track and each end region may be concave with respect to pivot axis 760, and may have a center of curvature on the pivot axis.

Figure 66:
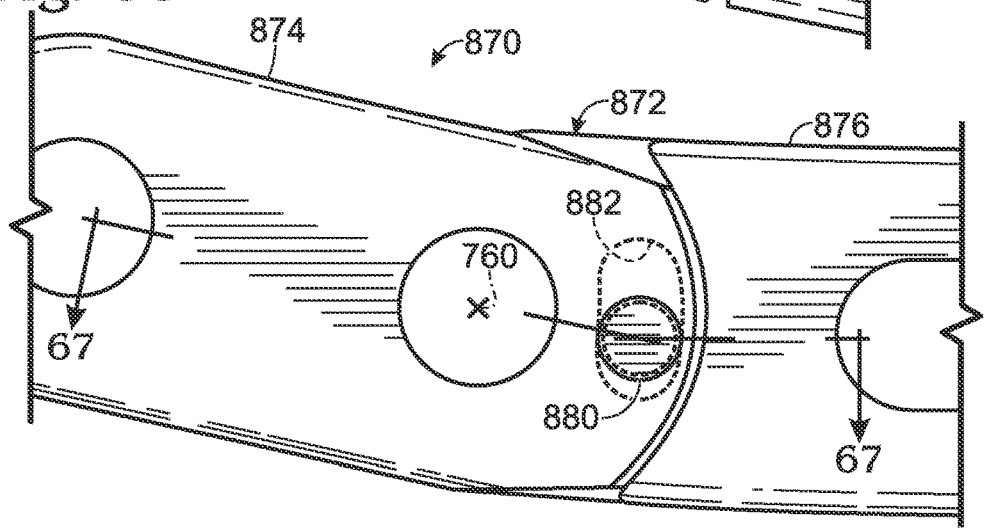
FIG. 66 is a fragmentary bottom view of a bone plate having a hinge joint with a range of pivotal motion determined by a pin received in a slot, with the range of pivotal motion preventing rotational disassembly of mated plate members of the hinge joint such that the plate members are permanently connected to one another, in accordance with aspects of the present disclosure.

FIGS. 66 and 67 show another exemplary bone plate 870 having a hinge joint 872 formed by a pair of plate members 874, 876 and a connector 878. (Connector 878 is present only in FIG. 67.) The bone plate may have any suitable combination of the features of the present disclosure.

Plate members 874, 876 are permanently connected to one another with a pin 880, whether or not connector 878 is installed. Pin 880 is attached to one of the plate members (e.g., rigidly coupled to plate member 874) and extends into an arcuate slot 882 defined by the other plate member (e.g., plate member 876). The pin travels along the slot as the plate members are pivoted relative to another about pivot axis 760, and is stopped by opposite ends of the slot, to define a range of rotation for the plate members about the pivot axis. The pin may extend into the bone plate from a position near the inner surface (or the outer surface) of the bone plate.

Pin 880 has a head 886 and a shaft 888. The pin may be attached to plate member 874 via head 886, and shaft 888 may extend into slot 882. In some embodiments, the pin may be press-fitted into an opening 890 defined by plate member 874 to attach the pin to the plate member.

The plate members may have various mating features. The mating features may include complementary rotational mating features 854 formed by plate members 874 and 876 at hinge joint 872, as described above for bone plate 830 (see FIG. 64). The mating features also or alternatively may include complementary mating features 892 that cooperate with pin 880 to permanently connect the plate members to one another. Mating features 892 include a protrusion, such as a boss 894, received in a complementary recess 896. The boss and recess both may be coaxial to pivot axis 760.

The plate members may be assembled with one another as follows. The plate members may be translationally mated with one another along pivot axis 760 by placing boss 894 into recess 896. Translational mating may be performed with plate members 874 and 876 at an angle to one another at which complementary mating features 854 are not yet mated with one another. In other words, mating features 854 are not yet overlapping because they are rotationally offset from one another. The angle may, for example, be at least 30 or 45 degrees from coaxial alignment of the plate members with one another.

The plate members then may be rotationally mated with one another by rotating the plate members relative to one another about pivot axis 760 toward coaxial alignment, such that complementary mating features 854 are mated with one another. Mating features 854 are considered mated when least a portion of each male region is received in each corresponding track (also see the description above for bone plate 830 (FIG. 64)).

The plate members may be rotationally adjusted, while remaining mated, such that opening 890 is aligned with slot 882. Pin 880 then may be placed into opening 890, to attach the pin to plate member 874, with the shaft of the pin extending into slot 882 of plate member 876. The plate members now are permanently connected to one another and are pivotable about pivot axis 760 through a range of rotation determined by the pin in the slot. This arrangement is advantageous because a discrete connector (besides the pin) is not required to keep the plate members connected, and because the range of motion can be determined inside the bone plate without affecting the external geometry of the bone plate.

Connector 878 may be installed in aligned apertures 898, 900 defined by the plate members at any suitable time. The connector may be placed through aperture 898 and into threaded engagement with aperture 900 before or after pin 880 is installed. Connector 878 can be manipulated to adjust hinge joint 872 between movable and fixed configurations, as described elsewhere herein. In some embodiments, bone plate 870 may be supplied to a user (e.g., a surgeon) with connector 878 already installed, and, optionally, with hinge joint 872 in a fixed configuration (e.g., with the plate members coaxially aligned with one another). The orientation of the plate members relative to one another may be adjusted via the hinge joint (in a movable configuration), and the plate members may be attached to bone with fasteners. Connector 878 may be replaced with a corresponding fastener 902 that has a longer shaft than the connector and is configured to extend into bone after the bone plate has been placed on and/or attached to the bone. Fastener 902 is disposed in threaded engagement with plate member 874 and is adjustable to place the hinge joint in a fixed configuration, with the fastener extending into bone. In other embodiments, connector 878 may be cannulated to define a through-hole with or without an internal thread. In these embodiments, a fastener may be placed into bone from the through-hole along pivot axis 760, while connector 878 remains attached to plate member 874.

FIGS. 68-70 show an exemplary bone plate 910 having an open hinge joint 912. The hinge joint is created by a pair of plate members 914, 916 and a snap-fit connector 918 that permanently connects the plate members to one another. Plate members 914, 916 have complementary mating features 854, as described above, and define a pair of aligned apertures 920, 922 to receive connector 918.

Connector 918 has a head 924 and a shaft 926. Shaft 926 defines a plurality of notches 928 (also called slots) that divide a leading end region of the shaft into a plurality of axial sections 930 (also called tabs). One or more of sections 930 have locking features 932 to create locking tabs that prevent removal of the connector after it has been snap-fitted into aligned apertures 920, 922. The locking features may project radially outward and engage a shoulder 934 defined by aperture 920, while head 924 engages a shoulder 936 defined by aperture 922, to prevent travel in either direction along pivot axis 760. Sections 930 are sufficiently flexible to bend radially inward as connector 918 is being placed into apertures 920, 922, and sufficiently elastic to move radially outward again after shoulder 934 has been cleared.

Connector 918 may define a through-hole 938, which may have an internal thread 940. The connector may be unable to rotate with respect to plate member 914 about pivot axis 760, which facilitates placement of a lock screw into threaded engagement with through-hole 938. Rotation of connector 918 may be prevented by a non-circular region (e.g., a flat 942) of the connector and a corresponding non-circular region of aperture 922 (see FIGS. 69 and 70). The lock screw may have a tapered head that urges sections 930 radially outward as the screw is advanced into through-hole 938, to place the joint in a fixed configuration.

Figure 71:
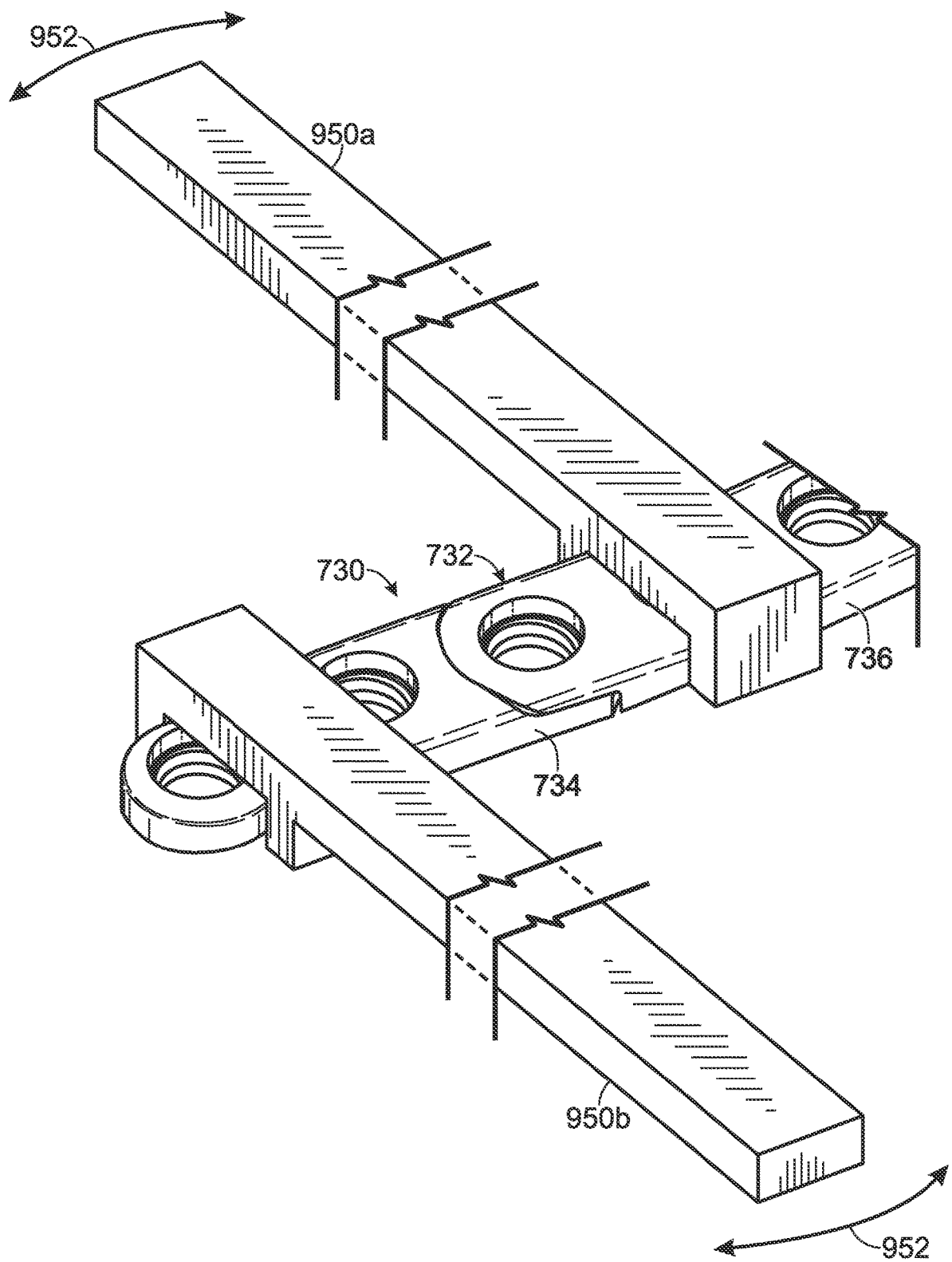
FIG. 71 is a view of the bone plate of FIG. 57 engaged by a pair of tools positioned on opposite sides of one of the hinge joints, with the tools are being used to apply torque to rotate plate members relative to one another, to adjust an orientation of the plate members, in accordance with aspects of the present disclosure.
Figure 72:
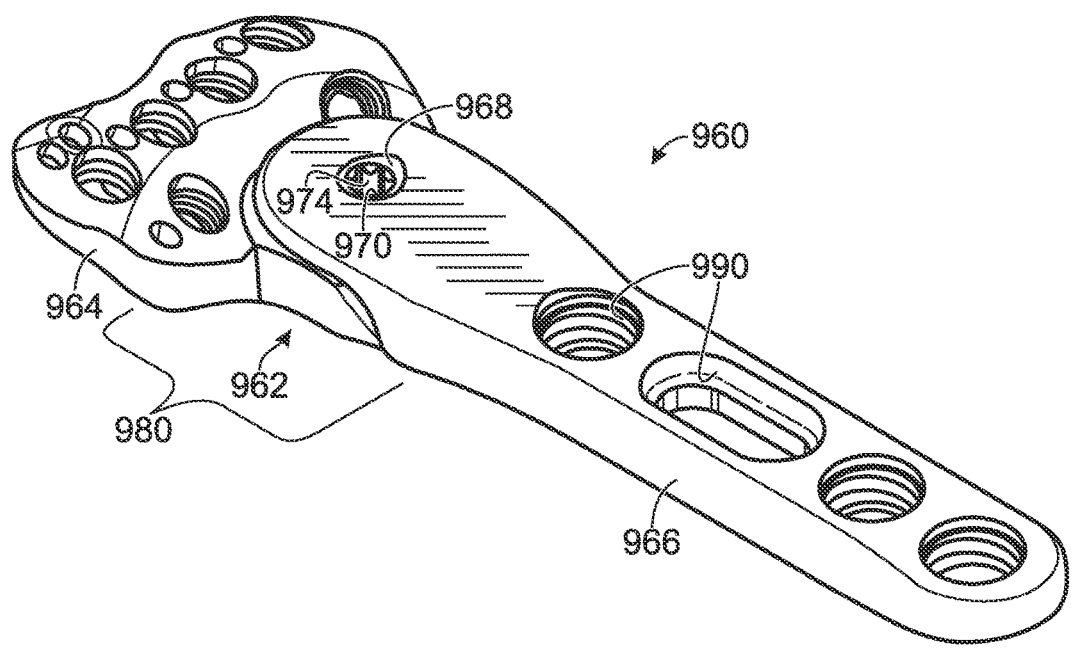
FIG. 72 is a view of an exemplary bone plate for fixation of the distal radius, with the bone plate having a multi-axis joint connecting a head plate member to a shaft plate member of the bone plate, and with the shaft plate member having a pair of deformable elements forming part of one of the joint surfaces of the joint and attached to a body of the shaft plate member, in accordance with aspects of the present disclosure.

FIG. 71 shows bone plate 730 of FIG. 57 engaged by a pair of tools 950a, 950b positioned on opposite sides of one of hinge joints 732. Tools 950a, 950b are being used to apply torque to rotate plate members 734, 736 relative to one another, indicated by arrows 952, to adjust an orientation of the plate members. The tools provide a mechanical advantage over manipulation of the plate members directly by hand, and allow application of a greater torque than with the hands alone. The tools, which may be called instruments, may or may not be copies of one another.

In other embodiments, tools 950a, 950b may be replaced by a single tool to apply the torque. For example, tools 950a, 950b may be hinged to one another to create a single tool.

Each tool may engage a suitable portion of the bone plate. In the depicted embodiment, each tool is engaging opposite edges of the bone plate when torque is applied. In other embodiments, the tool alternatively or additionally may engage one or more openings (e.g., through-holes) of the bone plate.

Each tool may provide a lever arm of any suitable length for application of torque to the bone plate. In some embodiments, the lever arm may be longer than one or both plate members that are being rotated relative to one another.

The tool may be configured to engage the bone plate when the bone plate is off bone, as shown here. Alternatively, the tool may be configured to engage the bone plate whether the bone plate is off bone or attached to bone.

Example 4. Exemplary Multi-Axis Joints and Associated Plate Structure

This example describes exemplary bone plates each including a movable joint connecting a pair of plate members, with the joint being a multi-axis joint having at least two nonparallel planes of adjustability; see FIGS. 72-86. The features of the bone plates and multi-axis joints described in this example may be combined with one another and/or with any of the elements and features described elsewhere in the present disclosure, such as in Sections I and III, and in other Examples of this section, among others.

FIGS. 72-76 show an exemplary bone plate 960 for fixation of the distal radius. The bone plate has a multi-axis joint 962 connecting a head plate member 964 to a shaft plate member 966. A connector 968 (e.g., a screw) is disposed in a pair of aligned apertures 970, 972 defined by the plate members. The connector is adjustable to change the joint between movable and fixed configurations. The connector may have an inverted configuration, with the head of the connector below the shaft, when the inner (bottom) surface of the bone plate is facing down. A shaft of the connector may define a driver interface to receive the working end of a suitable driver. For example, the shaft may define a socket 974 extending into the shaft from an end of the shaft opposite the head of the connector. Accordingly, the connector may have an external thread that is left-handed.

Plate members 964, 966 have respective head and shaft surface regions 976, 978 that are complementary to and face one another in a region of overlap 980 of the bone plate. Each of the surface regions may be spherical (i.e., defining and/or corresponding to a sphere or a portion thereof). The surface regions may or may not contact one another in the fixed configuration of the joint.

Figure 73:
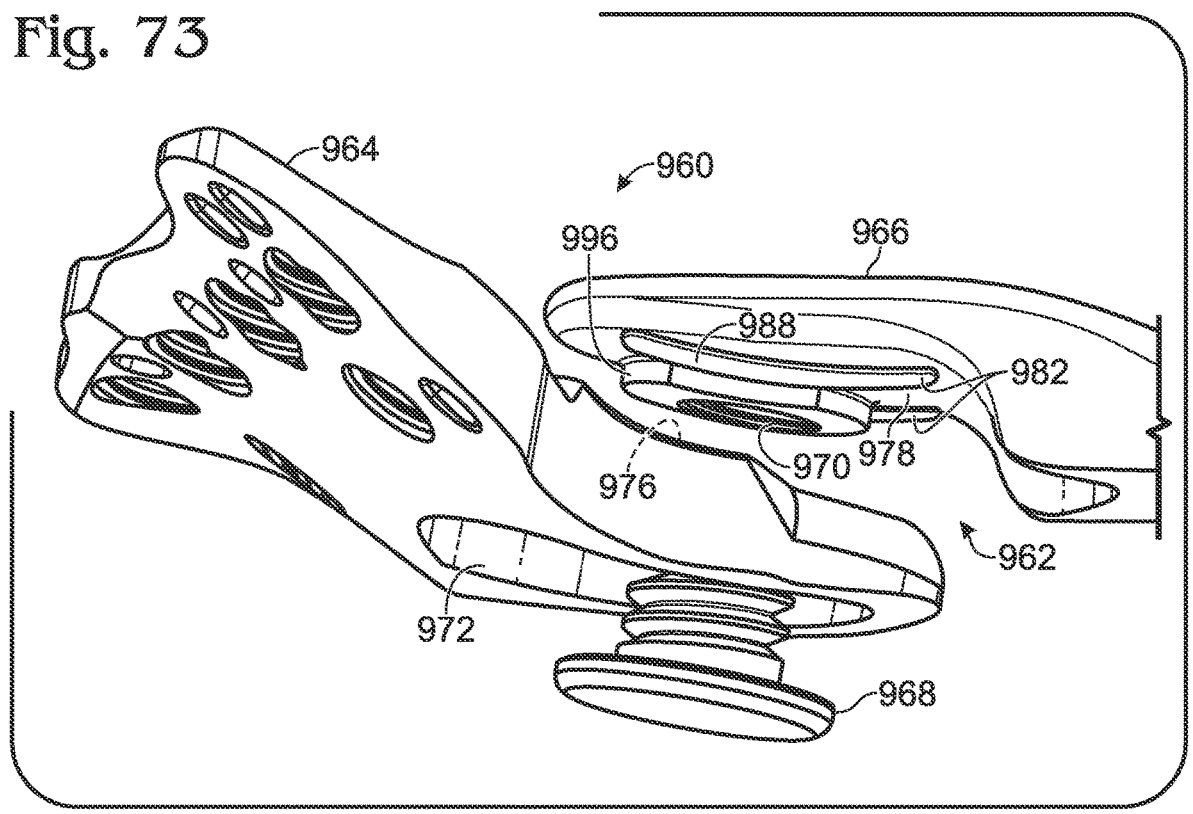
FIG. 73 is an exploded side view of the bone plate of FIG. 72, taken from below the bone plate.
Figure 74:
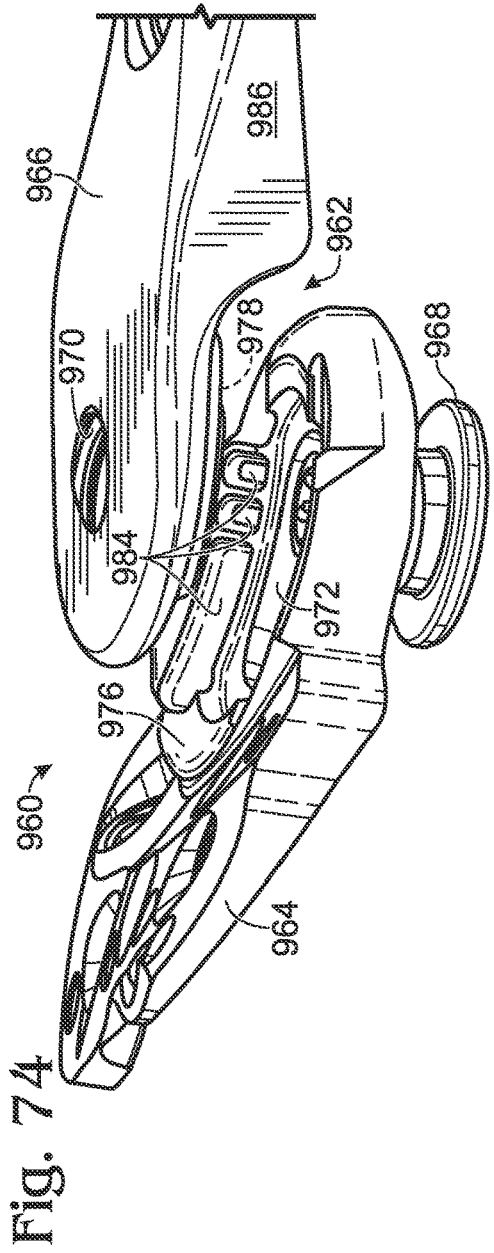
FIG. 74 is another exploded side view of the bone plate of FIG. 72, taken from above the bone plate.
Figure 76:
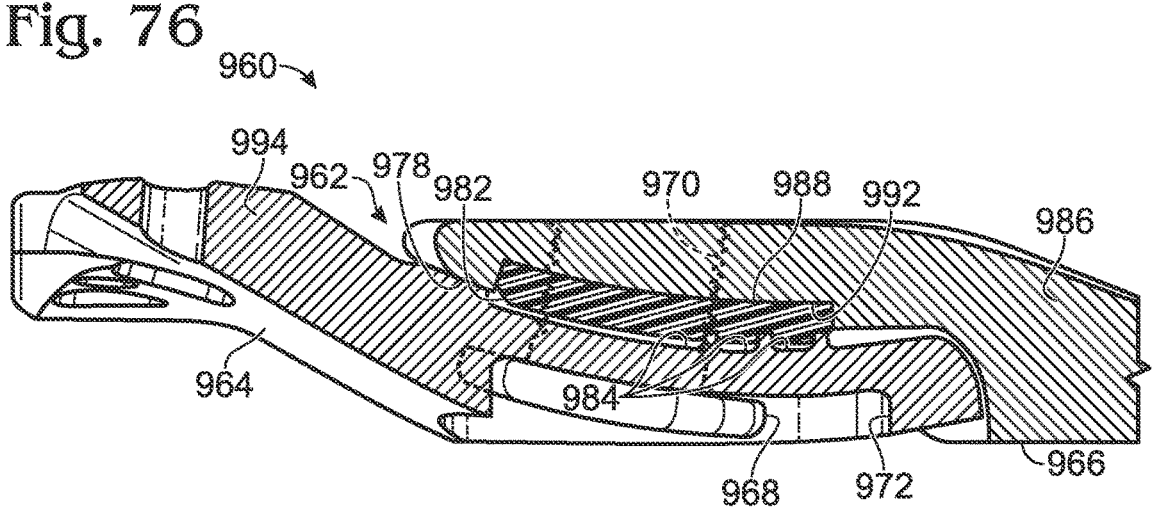
FIG. 76 is a fragmentary, partially sectional view of the bone plate of FIG. 72, taken generally along line 76-76 of FIG. 75.

Each plate member 964, 966 also may have a joint surface with one or more protrusions 982 (see FIGS. 73, 74, and 76) and/or defining one or more voids 984 (see FIGS. 74 and 76). Each protrusion is elevated, and each void is depressed, with respect to an associated surface region 976 or 978. In the depicted embodiment, protrusions 982 project from and are raised with respect to surface region 978 of shaft plate member 966. Also, voids 984 are recessed with respect to surface region 976 of head plate member 964. Each protrusion and void may function to prevent movement of the plate members relative to one another when joint 962 is in a fixed configuration, as described further below. The protrusion or void may be disposed within the perimeter of the surface region of the plate member and/or near (e.g., adjacent) the perimeter, among others.

Shaft plate member 966 has a body 986 and a pair of deformable elements 988 attached to the body in region of overlap 980 (see FIG. 76). Body 986 forms the majority of shaft plate member 966, for example, determining at least one, two, or each of the three characteristic dimensions (length, width, and thickness) of the shaft plate member. Body 986 also defines through-holes 990 outside region of overlap 980, to receive fasteners, and may define aperture 970 (see FIGS. 72 and 74). Furthermore, body 986 may define at least one recess 992 to receive deformable elements 988 (see FIG. 76). Recess 992 may have a depth that is less than the height of deformable element 988, such that the deformable element projects from the recess to form protrusion 982. Deformable element 988 may be attached to body 986 at recess 992.

Voids 984 may be formed integrally with joint surface region 976 of the joint surface by a body 994 of head plate member 964. Each body 986 and 994 may be harder than deformable element 988. Accordingly, deformation of the deformable element (and protrusion 982) may be predominant over deformation of surface region 976 and/or voids 984 when the joint is placed in the fixed configuration.

Bone plate 960 also may include a projection 996 of plate member 966 received in aperture 972 to define a range of motion of the plate members at joint 962 (see FIGS. 73 and 74). Projection 996 and aperture 972 are similar to projection 380 and aperture 382 of bone plate 360 (see FIGS. 24-26).

Figure 75:
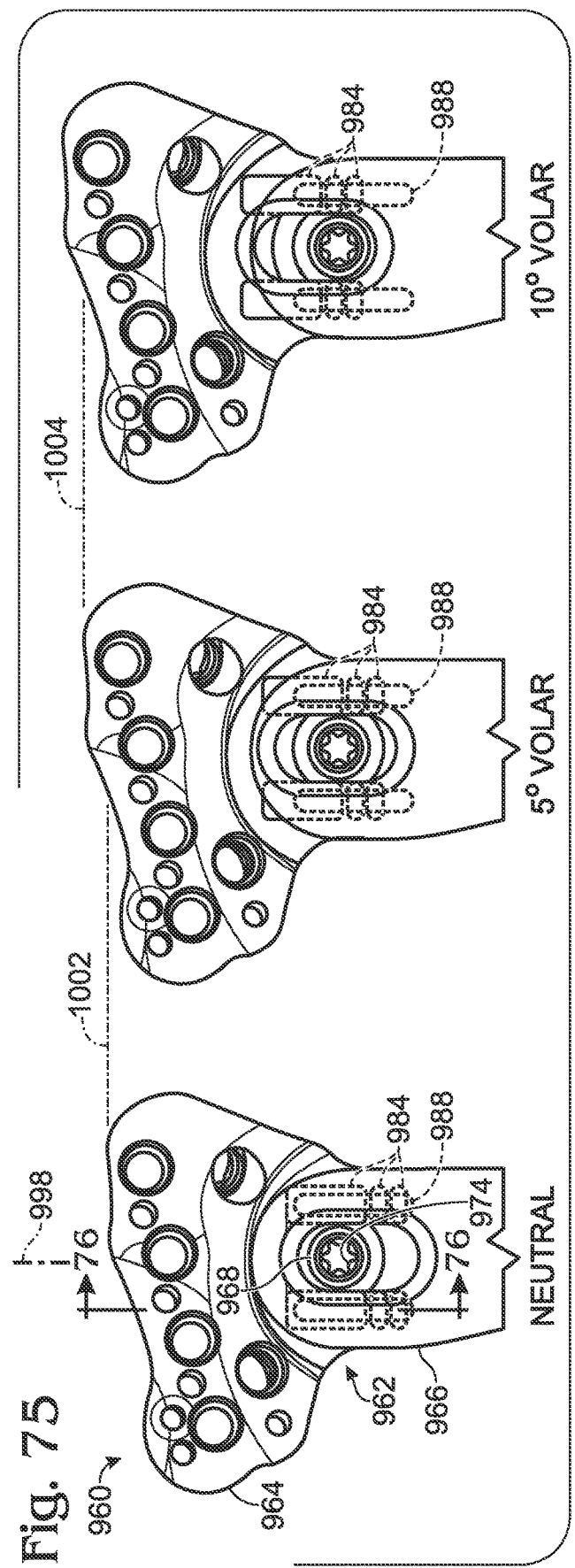
FIG. 75 is a fragmentary plan view of the bone plate of FIG. 72, taken with the head plate member of the bone plate in three different orientations permitted by the multi-axis joint and achieved by moving the head plate member in a plane that is parallel to the long axis of the shaft plate member and perpendicular to a plane defined by the shaft plate member, with the shaft plate member of the bone plate stationary to illustrate how the three different orientations change the length of the bone plate.

FIG. 75 shows bone plate 960 with head plate member 964 in three different volar orientations permitted by movement of the head plate member relative to shaft plane member 966 in a plane 998 that is parallel to the long axis of the shaft plate member and perpendicular to a plane defined by the shaft plate member. The three different orientations are labeled as neutral (arbitrarily assigned as 0° volar), 5° volar, and 10° volar. As the head plate member moves to a more volar inclination, the length of the bone plate increases, indicated by lines 1002 and 1004. Movement of deformable elements 988 with respect to voids 984 also is shown, with the voids moving distally as head plate member assumes a more volar tilt.

Figure 77:
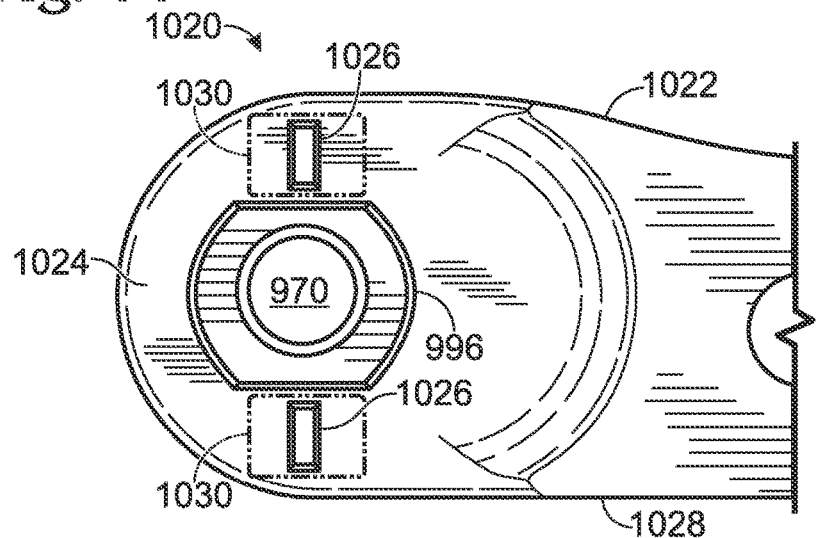
FIG. 77 is a fragmentary bottom view of a shaft plate member of still another exemplary bone plate for fixation of the distal radius, with the bone plate having a multi-axis joint connecting a head plate member to the shaft plate member, and with the head plate member including a joint surface forming a pair of protrusions that contact a pair of deformable elements of the joint surface of the shaft plate member, in accordance with aspects of the present disclosure.

FIG. 77 shows selected portions of another exemplary bone plate 1020 for fixation of the distal radius. In particular, only a bottom side of the proximal end region of a shaft plate member 1022 of bone plate 1020 is shown. The shaft plate member includes a joint surface region 1024 of a multi-axis joint. The bone may have any of the features described above for bone plate 960 (see FIGS. 72-76), such as aperture 970 and projection 996. However, the position of the deformable elements and the voids is different than in bone plate 960.

Shaft plate member 1022 provides a joint surface of the multi-axis joint. The joint surface is composed of surface region 1024 and a pair of protrusions 1026 projecting from the surface region within the perimeter thereof toward a joint surface from by the head plate member. Protrusions 1026 are formed integrally with a body 1028 of shaft plate member 1022, with the body forming surface region 1024. The protrusions overlap and contact a pair of underlying deformable elements 1030 (shown in phantom) of the joint surface of the head plate member. The deformable elements may be disposed in recesses defined by the body of the head plate member. The recesses are recessed with respect to a joint surface region of the head plate member. Each deformable element 1030 may protrude from one of the recesses to form a deformable protrusion that contacts and is deformed by one of protrusions 1026 (also see FIG. 15C). Alternatively, each deformable element 1030 may be flush or recessed with respect to the joint surface region of the head plate member (also see FIG. 15B). If recessed, the deformable element may define a void cooperatively with a portion of the recess in which the deformable element is located. The void may receive at least a portion of protrusion 1026 before the joint is locked, and may be deformed when the joint is placed in a fixed configuration.

FIGS. 78-81 show a bone plate 1040 having a multi-axis joint 1042 with a combination of discrete and continuous adjustability. The bone plate is configured, in the depicted embodiment, for fixation of the distal radius, but may be configured or use on any suitable bone. Bone plate 1040 has a head plate member 1044 connected to a shaft plate member 1046 at joint 1042 with a connector 1048 (e.g., an externally threaded member, such as a screw). The connector is disposed in a pair of aligned apertures 1050, 1052 and attaches to aperture 1052 via threaded engagement (see FIGS. 79 and 80). The connector allows the joint to be adjusted between movable and fixed configurations. In some embodiments, the connector may have an inverted configuration, with the head of the connector disposed below the shaft, as described elsewhere herein.

Figure 79:
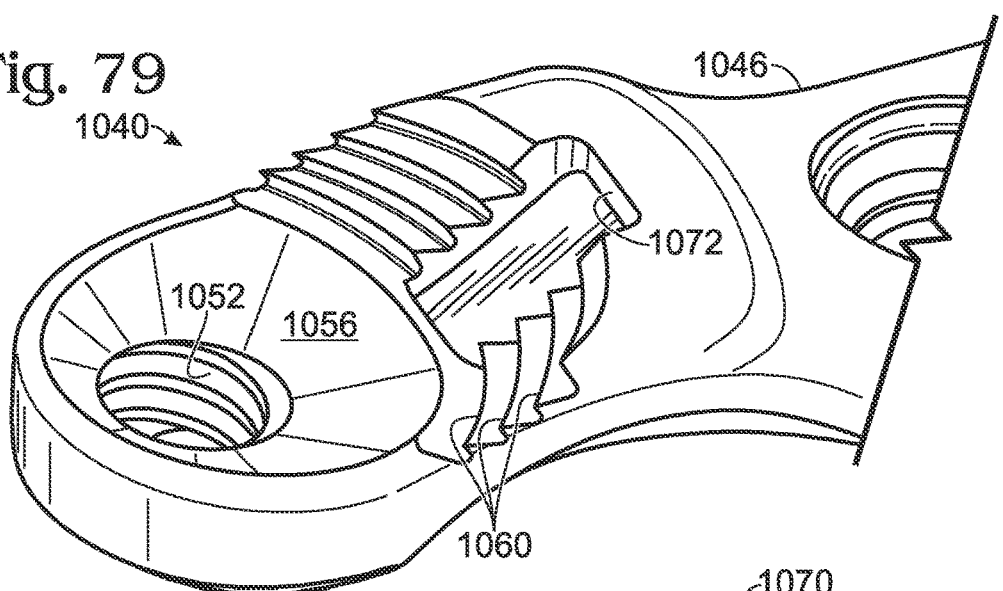
FIG. 79 is a fragmentary view of the shaft plate member of the bone plate of FIG. 78, taken from above the shaft plate member.
Figure 80:
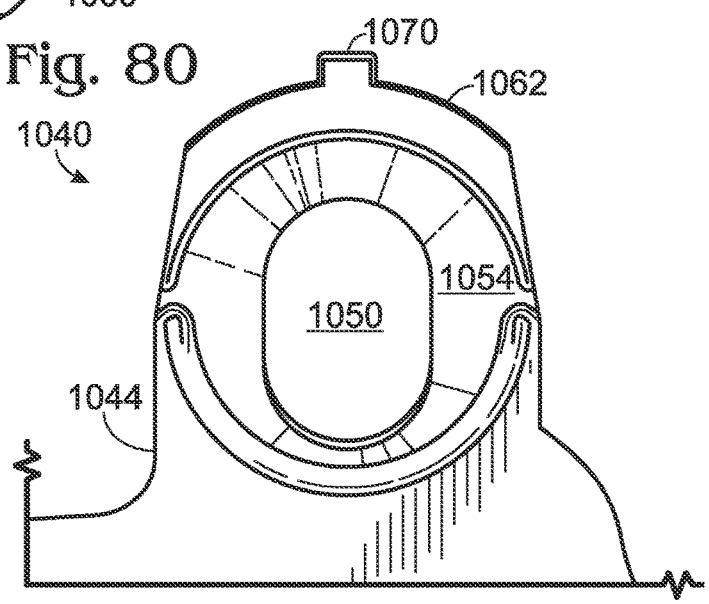
FIG. 80 is a fragmentary bottom view of the head plate member of the bone plate of FIG. 78.

Joint 1042 includes complementary joint surfaces 1054, 1056 that are spherical (see FIGS. 79 and 80). Joint surfaces 1054, 1056 face one another and may be in contact in movable and fixed configurations of the joint. The joint surfaces permit continuous adjustability in each plane of motion of the joint. Apertures 1050, 1052 extend through joint surfaces 1054 and 1056, respectively.

Figure 78:
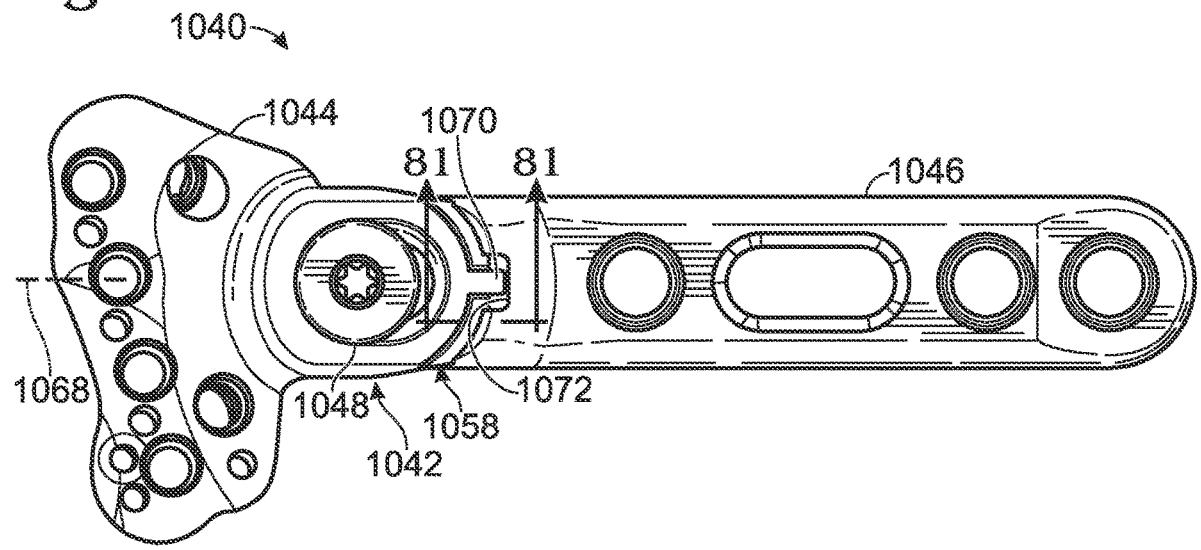
FIG. 78 is a plan view of yet another exemplary bone plate for fixation of the distal radius, with the bone plate having a multi-axis joint connecting a head plate member to a shaft plate member, and with the joint having discrete adjustability in a first plane and continuous adjustability in a second plane that is nonparallel to the first plane, in accordance with aspects of the present disclosure.
Figure 81:
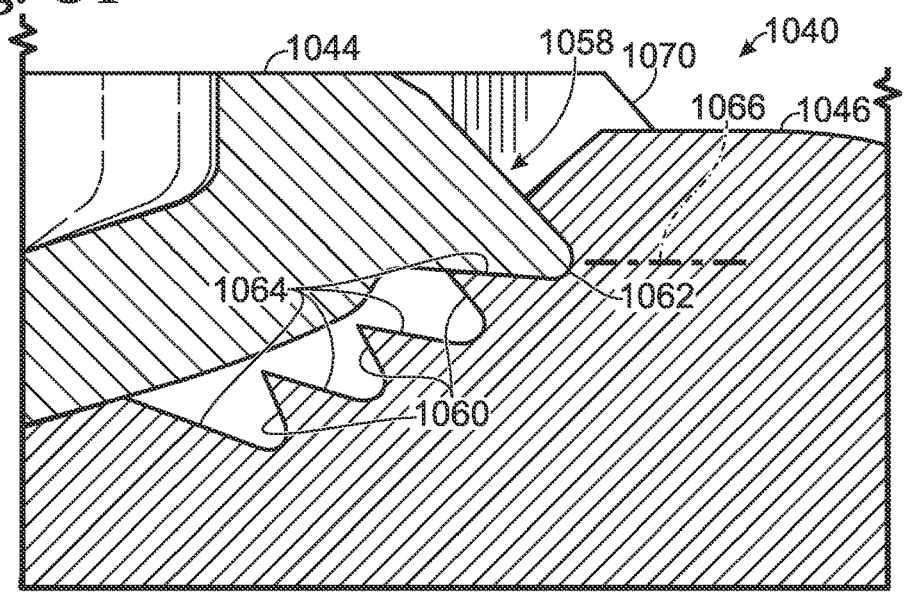
FIG. 81 is a sectional view of the bone plate of FIG. 78, taken generally along line 81-81 of FIG. 78.

Joint 1042 also includes a ratchet 1058 positioned adjacent the spherical part of the joint (see FIGS. 78 and 81). The ratchet is formed by a series of teeth 1060 of shaft plate member 1046 and an edge 1062 of head plate member 1044 that mates with the teeth (see FIGS. 79-81). Edge 1062 is alternatively received in each of a plurality of complementary notches 1064 (also called recesses) formed between the teeth, to discretely and incrementally adjust an orientation of the plate members in a plane orthogonal to a plane 1066 defined by the ratchet. Teeth 1060, edge 1062, and notches 1064 each may be arcuate in a plane parallel to plane 1066, and each may follow a portion of a circular path that is coaxial to aperture 1052. In the depicted embodiment, the ratchet provides discrete, incremental dorsal-ventral adjustability, and permits continuous radial-ulnar adjustability.

The ratchet provides discrete adjustability in each plane of a continuous set of vertical planes, such as plane 1068 (see FIG. 78), while permitting continuous adjustability in an at least generally horizontal plane 1066 (e.g., within 20, 10, or 5 degrees of perfectly horizontal) (see FIG. 81). (Vertical and horizontal with respect to bone plate 1040 are defined with the outer surface of the bone plate facing up and the inner surface facing down.) Placement of edge 1062 in each successive notch 1064 closer to joint surface 1056 creates incremental rotation of the head plate member relative to the shaft plate member in an at least generally vertical plane (e.g., within 20, 10, or 5 degrees of perfectly vertical) (see FIGS. 79 and 81).

The ratchet may provide any suitable number of discrete orientations of adjustment for the bone plate, such as at least or exactly 2, 3, 4, 5, or more. In the depicted embodiment, edge 1062 can be received alternatively in each of four notches 1064, to incrementally change the volar tilt of the head plate member. Successive notches may change the angle defined between the respective planes of the plate members by any suitable amount, such as at least or about 1, 2, 3, 4, or 5 degrees, among others.

The ratchet may selectively permit and restrict discrete adjustment in opposite rotational directions. In the depicted embodiment, the ratchet selectively permits incremental movement of edge 1062 toward joint surface 1056, while selectively restricting incremental movement of the edge away from joint surface 1056. Teeth 1060 may be asymmetrical to produce this bias for the direction of adjustment. The preferred rotational direction may increase (or decrease) an angular offset between respective planes defined by the plate members. For example, in the depicted embodiment, the preferred rotational direction incrementally increases the volar angle of tilt of the head plate member. In other embodiments, the ratchet may be configured to permit unbiased incremental adjustment in both rotational directions.

The range of motion of the plate members relative to one another in plane 1066 may be limited. In the depicted embodiment, a tab 1070 of head plate member 1044 is received in a slot 1072 of shaft plate member 1046. Contact between the tab and a wall of slot 1072 sets a limit for rotation in plane 1066 in both rotational directions, in each of the discrete mated configurations of edge 1062 with notches 1064. Slot 1072 interrupts teeth 1060 and notches 1064.

Tab 1070 provides an indicator for the orientation of the plate members in plane 1066. The orientation of tab 1070 with respect to slot 1072 corresponds to the orientation of the head plate member relative to the shaft plate member in plane 1066. The tab is visible from above the bone plate, which allows a surgeon to determine the orientation of the head plate member in plane 1066 by viewing the tab. In some embodiments, the shaft plate member may include reference marks arrayed transversely near the tab, to allow a surgeon to read the tab orientation more accurately.

Bone plate 1040 may have any suitable features of the other joints disclosed herein. For example, one or both joint surfaces 1054, 1056 may be configured to deform when the joint is placed in a fixed configuration. Each joint surface may include one or more protrusions and/or one or more voids to encourage deformation, as described in Section III (e.g., see FIGS. 15A-15E). At least one of the joint surfaces may (or may not) be formed, at least in part, by a discrete deformable element. Also, or alternatively, connector 1048 may have any of the features disclosed elsewhere herein. For example, the connector may be inverted, with a head under a shaft, and may have a left-handed thread. Also or alternatively, removal of the connector may be obstructed (e.g., by a flange of one of the plate members; see FIG. 62), such that the plate members are permanently connected to one another.

Figure 86:
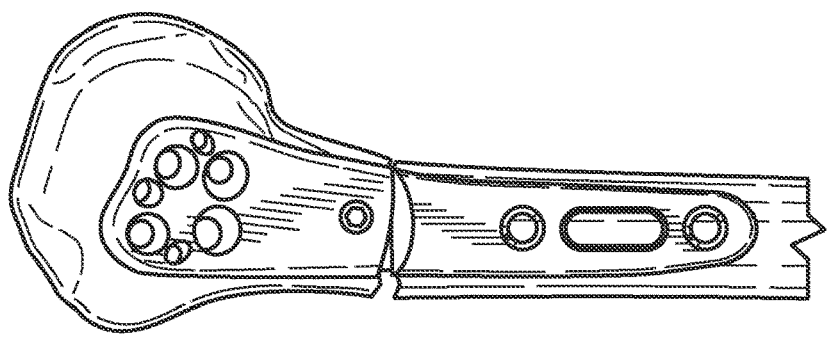
FIGS. 82-86 are a series of views of an exemplary bone plate for fixation of the proximal humerus, with the bone plate attached to a proximal humerus (fasteners are not shown) and having a multi-axis joint connecting a head plate member to a shaft plate member of the bone plate, and with the head plate member in various orientations relative to the shaft plate member, to show how the multi-axis joint can be used to adjust fracture reduction, in accordance with aspects of the present disclosure.
Figure 85:
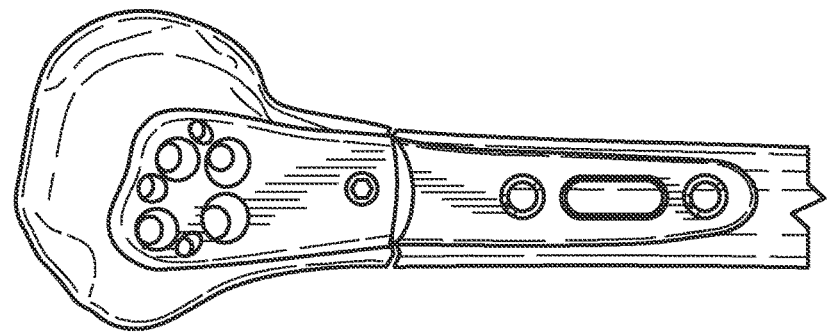
Figure 84:
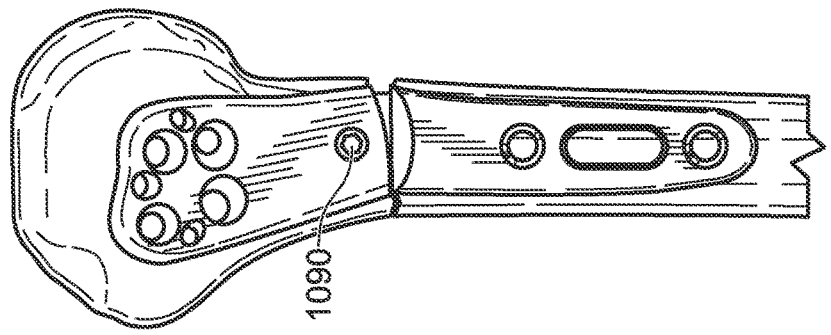
Figure 83:
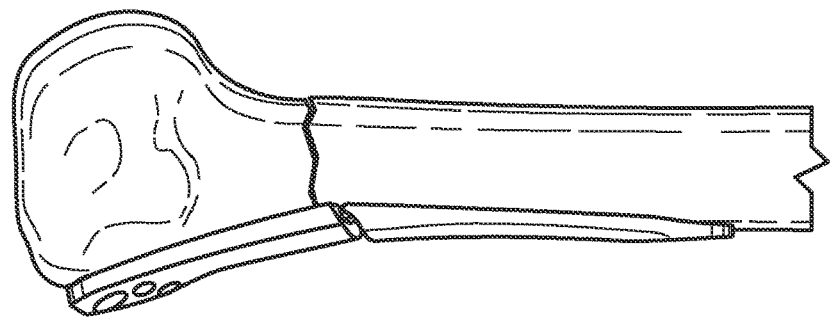
Figure 82:
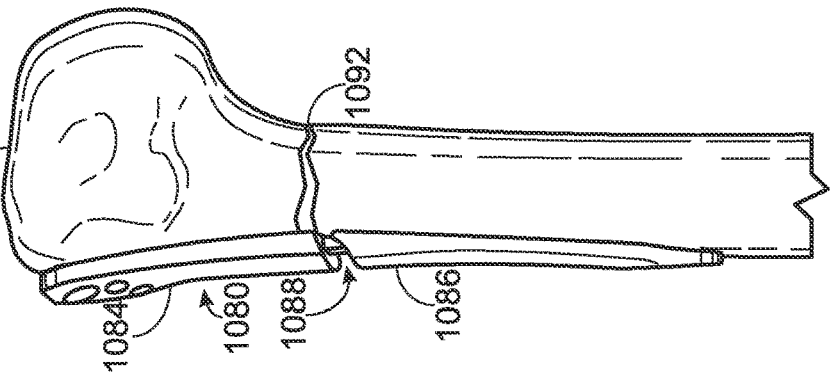

FIGS. 82-86 are a series of views of a bone plate 1080 for fixation of the proximal humerus 1082. The bone plate has a head plate member 1084 and a shaft plate member 1086 connected to one another by a multi-axis joint 1088 (see FIG. 82), such as any of the multi-axis joints of the present disclosure. The joint is lockable by manipulation of a connector 1090 (see FIG. 84). Humerus 1082 has sustained a fracture 1092 (or has been cut transversely), which divides the bone into a proximal piece and a distal piece. Each plate member is secured to one of the pieces with bone screws, although the screws are not shown here to simplify the presentation. FIGS. 82 and 83 show exemplary varus-valgus adjustment. FIGS. 84-86 show exemplary flexion-extension adjustment.

Example 5. Selected Embodiments I

The following selected embodiments, presented as a series of numbered paragraphs, are intended for illustration and should not limit the entire scope of the present disclosure.

1. A device for fixing bone, comprising: a pair of plate members connected to one another via a hinge joint, each plate member defining one or more apertures to receive fasteners that secure each of the pair of plates to bone.

2. The device of paragraph 1, wherein the hinge joint permits in-plane adjustment of the position of the plate members relative to one another.

3. The device of paragraph 1 or paragraph 2, wherein the pair of plate members define a pair of locking apertures that bracket the hinge joint.

4. The device of any of paragraphs 1 to 3, wherein the hinge joint includes a protrusion that is integral to one of the pair of plate members and that is received in a hole of the other of the pair of plate members.

5. The device of paragraph 4, wherein an end of the protrusion is swaged to prevent its removal from the hole.

6. The device of any of paragraphs 1 to 5, wherein the pair of plate members are mated with one another such that the plates cannot be separated from one another, at least when the plates are axially aligned with one another.

7. The device of paragraph 6, wherein one of the plate members defines a cavity, and wherein the other of the plate members has an end received in the cavity.

8. The device of paragraph 6 or paragraph 7, wherein the plate members are mated in a dovetail configuration.

9. The device of any of paragraphs 1 to 8, wherein the pair of plate members are a first plate member and a second plate member, further comprising a third plate member connected to the second plate member via another hinge joint.

10. The device of any of paragraphs 1 to 9, wherein one of the plate members is marked to indicate an axial zone within which each fracture of a bone should be located.

11. The device of any of paragraphs 1 to 10, wherein the pair of plate members define a pair of aligned apertures, further comprising a fastener configured (a) to be received in the pair of aligned apertures on an axis spaced from a pivot axis defined by the hinge joint and (b) to attach to at least one of the apertures of the pair of aligned apertures.

12. A device for fixing bone, comprising: a pair of plate members connected to one another at a rotatable joint, each plate member defining one or more apertures to receive fasteners that secure each of the pair of plate members to bone.

13. The device of paragraph 12, wherein the rotatable joint includes a deformable material disposed between the pair of plate members.

14. The device of paragraph 13, wherein the deformable material includes a polymer.

15. The device of paragraph 14, wherein the polymer includes polyether ether ketone (PEEK).

16. The device of any of paragraphs 12 to 15, wherein each plate member of the pair of plate members is formed of metal.

17. The device of any of paragraphs 12 to 16, wherein each plate member provides a joint surface of the rotatable joint, and wherein at least one of the joint surfaces defines a plurality of concavities.

18. The device of any of paragraphs 13 to 17, wherein at least one of the pair of plate members defines one or more concavities in which at least a portion of the deformable material is disposed before the rotatable joint is locked.

19. The device of any of paragraphs 13 to 18, wherein at least one of the pair of plate members defines a plurality of concavities configured to receive at least a portion of the deformable material when the deformable material is deformed by compression of the rotatable joint.

20. The device of paragraph 18 or paragraph 19, wherein the concavities include one or more grooves.

21. The device of any of paragraphs 18 to 20, wherein the one or more concavities are formed by a grid.

22. The device of any of paragraphs 18 to 21, wherein at least one of concavities is formed by machining, molding, etching, plasma coating, sintered particles, or a combination thereof.

23. The device of any of paragraphs 12 to 22, wherein joint surfaces of the pair of plate members contact one another, and wherein at least one of the joint surfaces is configured to deform when the rotatable joint is locked.

24. The device of any of paragraphs 12 to 23, wherein the rotatable joint permits the pair of plate members to pivot relative to one another in-plane and out-of-plane.

25. The device of any of paragraphs 12 to 24, wherein the rotatable joint has a center of rotation disposed above a top/outer side of the device.

26. The device of any of paragraphs 12 to 24, wherein the rotatable joint has a center of rotation disposed below a bottom/inner side of the device.

27. The device of any of paragraphs 12 to 26, further comprising a fastener extending from one plate member to the other plate member of the pair of plate members and adjustable to lock the rotatable joint.

28. The device of paragraph 27, wherein the fastener has a head and a shaft.

29. The device of paragraph 28, wherein the shaft extends toward a bottom/inner side of the device from the head.

30. The device of paragraph 28 or paragraph 29, wherein the head engages a collet to lock the rotatable joint.

31. The device of paragraph 30, wherein the collet is formed integrally by a plate member of the pair of plate members.

32. The device of paragraph 30 or 31, wherein the head is conical or at least tapers toward the shaft.

33. The device of any of paragraphs 28 and 30 to 32, wherein the shaft extends toward a top/outer side of the device from the head.

34. The device of paragraph 33, wherein a thread is formed on the shaft, and wherein the thread is reverse-handed (e.g., left-handed) relative to a thread formed on each fastener that attaches the bone plate to bone.

35. The device of any of paragraphs 12 to 34, wherein the rotatable joint has an unlocked configuration that restricts a range of motion of the pair of plate members relative to one another.

36. The device of paragraph 35, wherein one of the plate members defines a boss, wherein the other of the plate members defines an opening that receives the boss, wherein, optionally, a wall of the boss contacts a wall of the opening to restrict the range of motion, and wherein, optionally the range of motion is restricted in at least two nonparallel planes of rotation of the rotatable joint.

37. The device of paragraph 36, wherein the wall of the opening and/or the wall of the boss includes a pair of parallel wall regions that at least generally face one another.

38. A method of bone fixation, the method comprising: (A) selecting the device of any of paragraphs 1 to 37; and (B) securing the device to at least one bone with one or more fasteners, such as bone screws.

39. The method of paragraph 38, wherein the at least one bone is a distal radius, a clavicle, a proximal humerus, or a distal femur, among others.

40. The method of paragraph 38 or paragraph 39, further comprising a step of adjusting a position of the pair of plate members relative to one another before and/or after the step of securing, and a step of locking the joint after the step of adjusting.

41. The method of paragraph 40, wherein the step of adjusting is performed using one or more tools engaged with at least one of the plate members.

42. The method of any of paragraphs 38 to 41, further comprising a step of preventing movement of the plate members relative to one another with at least one fastener that extends into bone.

43. The method of paragraph 42, wherein the step of preventing movement includes a step of locking a bone screw to each plate member of the pair of plate members on opposite sides of the rotatable joint.

44. The method of any of paragraphs 38 to 41, further comprising a step of locking the joint with a fastener having a head disposed below joint surfaces of the plate members that face one another.

45. The method of any of paragraphs 38 to 41, further comprising a step of deforming a material and/or surface of the joint as the joint is being locked.

Example 6. Selected Embodiments II

The following selected embodiments, presented as a series of numbered paragraphs, are intended for illustration and should not limit the entire scope of the present disclosure. The embodiments relate to a bone plate having a hinge joint.

1. A bone plate for fixing bone, comprising: a pair of plate members overlapping and connected to one another in a region of overlap by a hinge joint that permits rotation of the plate members relative to one another about a pivot axis, each plate member defining one or more through-holes outside the region of overlap to receive one or more fasteners to attach the plate member to bone.

2. The bone plate of paragraph 1, further comprising a connector that connects the plate members to one another in the region of overlap to form the hinge joint, wherein the hinge joint permits in-plane rotation of the plate members relative to one another about a single pivot axis defined by the connector.

3. The bone plate of paragraph 2, wherein the hinge joint is adjustable between a movable configuration and a fixed configuration by manipulation of the connector.

4. The bone plate of any of paragraphs 1 to 3, wherein the bone plate defines a through-hole that is coaxial to the pivot axis and configured to receive a fastener that attaches the hinge joint to bone, wherein, optionally, the through-hole has an internal thread, and wherein, optionally, the through-hole is formed by a connector that connects the plate members to one another.

5. The bone plate of any of paragraphs 1 to 4, wherein contact between the pair of plate members sets a limit for pivotal motion in both rotational directions about the pivot axis.

6. The bone plate of any of paragraphs 1 to 5, wherein each plate member has a range of pivotal motion of no more than 20, 30, 40, or 50 degrees relative to the other plate member.

7. The bone plate of any of paragraphs 1 to 6, wherein the bone plate includes a third plate member, and wherein one of the plate members of the pair of plate members overlaps and is connected to the third plate member to form a pivotable connection that permits rotation of the one plate member and the third plate member relative to one another about another pivot axis.

8. The bone plate of paragraph 7, wherein the pivot axes are parallel to one another.

9. The bone plate of paragraph 7, wherein the pivot axes are not parallel to one another.

10. The bone plate of any of paragraphs 1 to 9, wherein the bone plate and/or one of the plate members defines a plane, and wherein each plate member remains in the plane as the plate member rotates about the pivot axis.

11. The bone plate of any of paragraphs 1 to 10, wherein the bone plate is configured to be attached to a clavicle.

12. A system including the bone plate of any of paragraphs 1 to 11 and further comprising a plurality of bone screws to occupy each of the one or more through-holes defined by each plate member and to occupy an additional through-hole that is coaxial to the pivot axis.

13. The bone plate of any of paragraphs 1 to 12, wherein the hinge joint creates a resistance to rotation of the plate members relative to one another about the pivot axis, and wherein the resistance is not adjustable off bone.

14. The bone plate of any of paragraphs 1 and 4 to 13, wherein one of the plate members includes an axle that extends into an aperture defined by the other plate member, and wherein the axle defines the pivot axis.

15. The bone plate of paragraph 14, further comprising a retainer that captures the axle in the aperture.

16. The bone plate of any of paragraphs 1 to 12, wherein the plate members are connected to one another by a connector having an external thread.

17. The bone plate of paragraph 16, wherein the connector has a head under a shaft.

18. The bone plate of paragraph 16 or paragraph 17, wherein the external thread is left-handed.

19. The bone plate of paragraph 16, wherein the connector is not removable.

20. The bone plate of paragraph 19, wherein one of the plate members obstructs travel of a head of the connector in both directions along the pivot axis.

21. The bone plate of any of paragraphs 1 to 20, wherein one of the plate members defines a slot, wherein the other plate member is attached to a pin that extends into the slot, and wherein the pin and the slot cooperatively define a range of rotation for the plate members about the pivot axis.

22. The bone plate of any of paragraphs 1 to 21, wherein one of the plate members forms a track, wherein the other plate member has an end region received in the track.

23. The bone plate of paragraph 22, wherein the track follows an arcuate path in a plane orthogonal to the pivot axis.

24. The bone plate of paragraph 23, wherein the arcuate path has a center of curvature on the pivot axis.

25. The bone plate of paragraph 22 or paragraph 23, wherein the end region and the track slide relative to one another along the arcuate path when the plate members are rotated about the pivot axis.

26. The bone plate of any of paragraphs 22 to 25, wherein the track is a channel.

27. The bone plate of paragraph 22, wherein the track is a first track and the end region is first end region, wherein the plate members form a second track and a second end region received in the track, and wherein the second track and the second end region are spaced from the first track and the first end region.

28. The bone plate of paragraph 27, wherein the pivot axis extends through the bone plate between the first track and the second track.

29. The bone plate of paragraph 27 or paragraph 28, wherein the other plate member forms the second track.

30. The bone plate of any of paragraphs 27 to 29, wherein each track and each end region is arcuate in a plane orthogonal to the pivot axis.

31. Method of making a device for bone fixation, the method comprising, in any order: (A) mating a first plate member with a second plate member, the plate members having complementary features such that the mated plate members are able to rotate relative to one another about a pivot axis until the plate members are unmated, and prevented from being separated, while mated, by movement relative to one another parallel to the pivot axis; and (B) installing a pin that establishes a range of rotation for the plate members to prevent rotational unmating of the plate members from one another.

32. A method of fixing bone, the method comprising, in any order: (A) placing a bone plate onto a bone as a unit, the bone plate including a pair of plate members overlapping and pre-connected to one another at a region of overlap to form a pivotable connection that permits rotation of the plate members relative to one another about a pivot axis; (B) attaching each plate member to the bone with one or more fasteners extending into the bone from one or more through-holes defined by the plate member outside the region of overlap; and (C) attaching the region of overlap of the bone plate to the bone with a threaded fastener extending along the pivot axis into the bone from the region of overlap.

33. The method of paragraph 32, further comprising a step of adjusting an orientation of the plate members relative to one another before, after, or both before and after the step of attaching each plate member to bone.

34. The method of paragraph 33, wherein the step of adjusting an orientation of the plate members is performed at least partially after the step of placing a bone plate onto a bone.

35. The method of paragraph 34, wherein the step of adjusting an orientation is performed at least partially off bone.

36. The method of any of paragraphs 32 to 35, wherein the step of attaching the region of overlap includes a step of placing the threaded fastener into threaded engagement with the bone plate.

37. The method of paragraph 36, wherein the step of placing the threaded fastener includes a step of placing the threaded fastener into threaded engagement with an integral portion of one of the plate members.

38. The method of paragraph 37, further comprising a step of placing the hinge joint in a locked configuration by expanding a region of the bone plate with a tapered portion of the threaded fastener.

39. The method of any of paragraphs 36 to 38, wherein the bone plate includes a connector that is discrete from each of the plate members and that connects the plate members to one another in the region of overlap, and wherein the step of placing the threaded fastener includes a step of placing the threaded fastener into threaded engagement with the connector.

40. The method of any of paragraphs 32 to 39, further comprising a step of placing the hinge joint in a fixed configuration that prevents pivotal motion of the plate members relative to one another.

41. The method of paragraph 40, wherein the step of attaching is performed after the step of placing the hinge joint in the fixed configuration.

42. The method of paragraph 40 or paragraph 41, wherein the step of placing the hinge joint in a fixed configuration includes a step of turning a connector that pre-connects the plate members to one another.

43. The method of any of paragraphs 32 to 42, wherein the bone is a clavicle.

44. The method of any of paragraphs 32 to 43, wherein the bone plate includes at least three plate members and at least two hinge joints at which the at least three plate members are pre-connected to one another permanently.

45. A method of making a device for bone fixation, the method comprising, in any order: (A) placing an integrally formed protrusion of a first plate member into an opening of a second plate member, each plate member defining one or more through-holes to receive fasteners to attach the plate member to bone; and (B) deforming the protrusion to prevent removal of the protrusion from the opening and form a pivotable connection that permits rotation of the plate members relative to one another about a pivot axis.

46. A method of making a device for bone fixation, the method comprising, in any order: (A) connecting a first plate member to a second plate member such that the plate members overlap one another at a region of overlap and are connected to one another in the region of overlap with a connector to form a pivotable connection that permits rotation of the plate members relative to one another about a pivot axis; and (B) deforming one of the plate members such that removal of the connector is prevented.

47. The method of paragraph 46, wherein one of the plate members forms a flange, and wherein the step of deforming includes a step of deforming the flange.

48. The method of paragraph 47, wherein the connector includes a head, and wherein the step of deforming the flange causes the flange to obstruct travel of the head out of the one plate member.

49. Method of making a device for bone fixation, the method comprising in any order: (A) placing a deformable region of a connector through an opening of a first plate member and into an opening of a second plate member to form a pivotable connection that permits rotation of the plate members relative to one another about a pivot axis; wherein the deformable region is deformed radially inward as the deformable region enters the opening of the second plate member and then expands radially outward to prevent removal of the connector from the opening of the second plate member.

50. The method of paragraph 49, wherein the deformable region includes a plurality of tabs each having a region that projects radially outward.

Example 7. Selected Embodiments III

The following selected embodiments, presented as a series of numbered paragraphs, are intended for illustration and should not limit the entire scope of the present disclosure. Paragraph 1. A method of manufacturing a bone plate, the method comprising, in any order: (A) forming one or more through-holes in each of a first plate member and a second plate member, the one or more through-holes being configured to receive one or more fasteners to attach each plate member to bone; (B) disposing an axle of the second plate member in an aperture defined by the first plate member; and (C) creating a retainer for the axle while the axle remains in the aperture; wherein the step of creating a retainer permanently connects the plate members to one another in a configuration that permits in-plane rotation of the plate members relative to one another about a pivot axis defined by the axle.

2. The method of paragraph 1, wherein the step of creating a retainer includes a step of plastically deforming a region of the axle to prevent the region from passing through the aperture.

3. The method of paragraph 1, wherein the step of creating a retainer includes a step of welding a retainer to the axle.

4. The method of any of paragraphs 1 to 3, wherein the step of creating a retainer includes a step of tightly engaging the first plate member with the retainer.

5. The method of paragraph 4, wherein the step of tightly engaging renders the plate members resistant to rotation relative to one another about the pivot axis when torque is applied directly to the bone plate with a user's hands.

6. The method of any of paragraphs 1 to 5, wherein the second plate member is formed integrally.

7. The method of any of paragraphs 1 to 6, wherein the step of disposing an axle is performed after the step of forming one or more through-holes.

8. The method of any of paragraphs 1 to 7, further comprising a step of creating a through-hole that extends through the axle and the retainer.

9. The method of paragraph 8, wherein the step of creating a through-hole includes a step of creating a through-hole having an internal thread.

10. The method of paragraph 8 or 9, wherein the step of disposing an axle includes a step of disposing an axle having a pre-formed through-hole, wherein, optionally, the step of creating a through-hole includes a step of modifying the pre-formed through-hole after the step of creating a retainer, and wherein, optionally the step of modifying the pre-formed through-hole includes a step of creating an internal thread in the pre-formed through-hole.

11. A bone plate for fixing bone, comprising: (A) a first plate member defining an aperture; and (B) a second plate member having an axle; wherein each plate member defines one or more through-holes to receive one or more fasteners to attach the plate member to bone, and wherein the axle is captured in the aperture such that the first and second plate members are permanently connected to one another and form a hinge joint that permits in-plane rotation of the plate members relative to one another about a pivot axis defined by the axle.

12. The bone plate of paragraph 11, wherein the second plate member includes a body defining the one or more through holes, wherein the axle projects from the body into the aperture, wherein the second plate member includes a retainer that is continuous with or fused to the axle opposite the body, and wherein the retainer is unable to pass through the aperture and is tightly engaged with the first plate member to prevent the hinge joint from moving freely.

13. The bone plate of paragraph 11 or 12, wherein the retainer and the axle are formed integrally with one another.

14. The bone plate of paragraph 11 or 12, wherein the retainer is welded to the axle.

15. The bone plate of any of paragraphs 11 to 14, wherein the bone plate defines a through-hole that is coaxial with the pivot axis and configured to receive a fastener to attach the hinge joint to bone.

16. The bone plate of paragraph 15, wherein the through-hole that is coaxial with the pivot axis has an internal thread.

17. The bone plate of any of paragraphs 11 to 16, wherein the hinge joint has an intrinsic resistance to pivotal motion of the plate members relative to one another, and wherein the intrinsic resistance is configured not to be adjustable off bone.

18. A system comprising the bone plate of paragraph 11, further comprising at least one tool to pivot the plate members relative to one another about the pivot axis, wherein the at least one tool is longer than at least one of the plate members.

19. The bone plate of any of paragraphs 11 to 17, wherein one of the plate members is elongated and is marked at its surface to indicate a fracture zone of the one plate member for overlap with each fracture of a bone to be fixed, and wherein the fracture zone extends along only a portion of the length of the one plate member.

20. A method of fixing bone, the method comprising, in any order: (A) selecting a bone plate including a first plate member defining an aperture and a second plate member having an axle that is captured in the aperture such that the first and second plate members are permanently connected to one another and form a hinge joint that permits in-plane rotation of the plate members relative to one another about a pivot axis defined by the axle; (B) rotating the plate members relative to one another about the pivot axis; and (C) attaching each plate member to a bone with one or more fasteners extending into the bone.

21. The method of paragraph 20, wherein the step of rotating the plate members is performed before both of the plate members are attached to the bone.

22. The method of paragraph 20 or 21, wherein the step of attaching each plate member includes a step of attaching each plate member to a clavicle.

23. The method of any of paragraphs 20 to 22, further comprising a step of attaching the hinge joint to the bone with a fastener extending into the bone along the pivot axis from a through-hole defined at least in part by the axle.

24. The method of any of paragraphs 20 to 23, wherein the step of rotating the plate members is performed by application of torque with one or more tools engaged with the plate members.

25. The method of paragraph 24, wherein the step of rotating the plate members includes a step of applying torque with a lever arm that is longer than at least one of the plate members.

26. The method of any of paragraphs 20 to 25, further comprising a step of making an incision in soft tissue over the bone, a step of placing the bone plate onto the bone, and a step of closing the incision after the steps of rotating the plate members and attaching each plate member, wherein the step of placing the bone plate is performed via the incision, and wherein resistance of the hinge joint to rotation of the plate members about the pivot axis is not adjusted after the step of rotating the plate members and before the step of closing the incision.

27. A bone plate for fixing bone, comprising: (A) a pair of plate members overlapping one another at a region of overlap, each plate member defining one or more through-holes outside the region of overlap to receive one or more fasteners to attach the plate member to bone; and (B) a connector that connects the plate members to one another in the region of overlap to form a hinge joint that permits in-plane rotation of the plate members relative to one another about a pivot axis defined by the connector; wherein the hinge joint is adjustable between a movable configuration and a fixed configuration by manipulation of the connector, and wherein the connector defines a through-hole that is coaxial to the pivot axis and configured to receive a fastener that attaches the region of overlap to bone.

28. The bone plate of paragraph 27, wherein the through-hole that is coaxial to the pivot axis has an internal thread.

29. The bone plate of paragraph 27 or 28, wherein the plate members are permanently connected to one another.

30. The bone plate of any of paragraphs 27 to 29, wherein the connector has a head and a shaft, and wherein one of the plate members forms a flange that obstructs axial travel of the head out of the bone plate in a direction away from the shaft.

31. The bone plate of any of paragraphs 27 to 30, wherein the through-hole defined by the connector has a same inner diameter as at least one of the through-holes defined outside the region of overlap.

32. The bone plate of any of paragraphs 27 to 31, wherein the bone plate has an inner surface configured to contact bone, wherein the connector has a head and a shaft, and wherein the head is under the shaft when the inner surface is facing down.

33. The bone plate of paragraph 32, wherein the shaft has an external thread that is left-handed.

34. The bone plate of paragraph 33, wherein at least one of the one or more through-holes has an internal thread that is right-handed.

35. The bone plate of any of paragraphs 27 to 34, wherein the connector is rotationally fixed with respect to one of the plate members in the movable configuration.

36. The bone plate of any of paragraphs 27 to 35, wherein the connector has a shaft defining a plurality of notches.

37. The bone plate of paragraph 36, wherein the notches divide an end region of the shaft into a plurality of sections, and wherein one or more of the sections include a locking feature that prevents removal of the connector in one direction along the pivot axis.

38. The bone plate of any of paragraphs 27 to 37, wherein the connector has a snap-fit connection to one of the plate members.

39. The bone plate of any of paragraphs 27 to 38, wherein each of the plate members is formed integrally.

40. The bone plate of any of paragraphs 27 to 39, wherein one of the plate members forms a track, and wherein an end region of the other plate member is received in the track.

41. A method of fixing bone, the method comprising, in any order: (A) selecting a bone plate including a pair of plate members overlapping one another at a region of overlap and a connector that connects the plate members to one another in the region of overlap to form a hinge joint having a pivot axis defined by the connector; (B) rotating the plate members relative to one another in-plane about the pivot axis; (C) attaching each plate member to a bone with one or more fasteners extending into the bone from one or more through-holes defined by the plate member outside the region of overlap; and (D) attaching the hinge joint to the bone with a fastener extending into the bone from a through-hole defined by the connector.

42. The method of paragraph 41, further comprising a step of manipulating the connector after the step of rotating the plate members to fix an orientation of the plate members relative to one another.

43. The method of paragraph 41 or 42, wherein the connector includes an external thread, and wherein the step of manipulating the connector includes a step of turning the connector about the pivot axis.

44. The method of any of paragraphs 41 to 43, wherein the bone is a clavicle.

45. The method of any of paragraphs 41 to 44, wherein the step of attaching the hinge joint includes a step of placing a fastener in threaded engagement with the connector.

46. The method of paragraph 45, wherein the fastener in threaded engagement with the connector has a right-handed external thread, and wherein the connector has a left-handed external thread.

47. The method of any of paragraphs 41 to 46, wherein the step of rotating the plate members is performed before at least one of the plate members is attached to bone.

48. The method of any of paragraphs 41 to 47, further comprising a step of placing the hinge joint in the fixed configuration, wherein the step of rotating the plate members and the step of placing the hinge joint in the fixed configuration are performed with the plate members off bone.

49. A bone plate for fixing bone, comprising: (A) a pair of plate members mated with one another via complementary mating features that (a) allow in-plane rotation of the plate members relative to one another about a pivot axis while the plate members remain mated and (b) prevent translational disassembly of the mated plate members, each plate member defining one or more through-holes to receive one or more fasteners to attach the plate member to bone; and (B) a pin attached to one of the plate members and extending into a slot defined by the other plate member; wherein the pin and the slot define a permitted range of rotation of the plate members relative to one another about the pivot axis, and wherein the permitted range of rotation prevents rotational disassembly of the mated plate members.

50. The bone plate of paragraph 49, further comprising a threaded member that attaches to one of the plate members and is adjustable to prevent rotation of the plate members relative to one another about the pivot axis.

51. The bone plate of paragraph 49 or 50, wherein the plate members are permanently connected to one another.

52. A method of creating a bone plate, the method comprising, in any order: (A) mating a pair of plate members with one another, the plate members having complementary features such that the mated plate members are (i) rotatable relative to one another about a pivot axis while the plate members remain mated with one another and (ii) prevented from translational disassembly; and (B) attaching a pin to one of the plate members such that the pin extends into a slot defined by the other plate member to establish a range of rotation for the plate members that prevents rotational disassembly of the mated plate members.

53. The method of paragraph 52, wherein the step of mating includes a step of rotationally mating the plate members with one another.

54. The method of paragraph 52, wherein the step of attaching a pin includes a step of press-fitting the pin into an opening defined by the one plate member.

55. The method of paragraph 52, wherein the step of mating includes a step of placing a boss of one of the plate members in a recess defined by the other plate member, and wherein the boss and the recess are each coaxial to the pivot axis after the step of mating.

56. The method of paragraph 55, wherein the step of mating includes a step of rotating the plate members relative to another about the pivot axis after the step of placing a boss, such that a track of one of the plate members is mated with an end region of the other plate member, and wherein the track mated with the end region prevents disassembly of the plate members from one another in both directions parallel to the pivot axis.

57. The method of paragraph 56, wherein each of the track and the end region is arcuate in a plane orthogonal to the pivot axis.

58. The method of paragraph 56, wherein the step of rotating the plate members includes a step of mating a first track with a first end region and a second track with a second end region, and wherein the pivot axis is disposed between the first track and end region and the second track and end region after the step of rotating the plate members.

59. The method of paragraph 58, wherein each track has a center of curvature on the pivot axis.

60. A bone plate for fixing bone, comprising: (A) a pair of plate members overlapping one another at a region of overlap, each plate member defining one or more through-holes outside the region of overlap to receive one or more fasteners to attach the plate member to bone; and (B) a connector attached to one of the plate members in the region of overlap to form a hinge joint that permits in-plane rotation of the plate members relative to one another about a pivot axis defined by the connector; wherein the hinge joint is adjustable between a movable configuration and a fixed configuration by manipulation of the connector, wherein the connector has a head and a shaft, and wherein one of the plate members obstructs travel of the head out of the bone plate in both directions along the pivot axis.

61. The bone plate of paragraph 60, wherein the plate members are permanently connected to one another.

62. The bone plate of paragraph 60, wherein the bone plate has an inner surface configured to contact bone, and wherein the head is under the shaft when the inner surface is facing down.

63. The bone plate of paragraph 60, wherein the one plate member has a flange that obstructs travel of the head along the pivot axis in a direction away from the shaft.

64. A bone plate for fixing bone, comprising: (A) a pair of plate members overlapping one another at a region of overlap, each plate member defining one or more through-holes outside the region of overlap to receive one or more fasteners to attach the plate member to bone; and (B) a connector attached to one of the plate members in the region of overlap to form a hinge joint that permits in-plane rotation of the plate members relative to one another about a pivot axis defined by the connector; wherein the hinge joint is adjustable between a movable configuration and a fixed configuration by manipulation of the connector, and wherein the connector is configured not to be removable, such that the plate members are permanently connected to one another.

65. A method of manufacturing a bone plate, the method comprising in any order: (A) connecting a pair of plate members to one another with a connector to form a hinge joint that permits the plate members to rotate relative to one another in-plane about a pivot axis defined by the connector, wherein the hinge joint is adjustable between a movable configuration and a fixed configuration by manipulation of the connector; (B) creating one or more through-holes in each plate member to receive one or more fasteners to attach each plate member to bone; and (C) deforming a region of one of the plate members to prevent removal of the connector, such that the plate members are permanently connected to one another.

66. The method of paragraph 65, wherein the one plate member has a flange projecting from an outer surface or an inner surface of the one plate member before the step of deforming, and wherein the step of deforming includes a step of deforming the flange.

67. The method of paragraph 66, wherein the step of deforming includes a step of deforming at least a portion of the flange toward the pivot axis.

68. The method of paragraph 66 or 67, wherein the connector has a head and a shaft, and wherein the step of deforming obstructs travel of the head out of the bone plate along the pivot axis in a direction away from the shaft.

69. The method of any of paragraphs 65 to 68, wherein the step of creating one or more through-holes is performed before the step of connecting.

70. A bone plate for fixing bone, comprising: (A) a first plate member and a second plate member overlapping one another at a region of overlap, each plate member defining one or more through-holes outside the region of overlap to receive one or more fasteners to attach the plate member to bone; and (B) a connector that connects the plate members to one another in the region of overlap to form a joint having (i) a movable configuration that permits changing an orientation of the plate members relative to one another in each of at least two nonparallel planes, and (ii) a fixed configuration in which the orientation of the plate members is fixed; wherein the first and second plate members have respective first and second surface regions that are complementary to and face one another, wherein the first plate member defines one or more protrusions that are raised with respect to the first surface region, wherein the second plate member defines one or more voids that are recessed with respect to the second surface region, and wherein the one or more protrusions are configured to deform and/or be deformed by the second plate member when the joint is placed in the fixed configuration, such that at least a portion of each protrusion extends beyond the second surface region into at least one of the one or more voids.

71. The bone plate of paragraph 70, wherein the first plate member has a body that forms the first surface region, and wherein the one or more protrusions are discrete from the body.

72. The bone plate of paragraph 71, wherein the body defines one or more recesses, wherein the first plate member includes one or more deformable elements that are disposed in the one or more recesses and project therefrom to form the one or more protrusions, and wherein the one or more deformable elements are deformed when the joint is placed in the fixed configuration.

73. The bone plate of paragraph 72, wherein deformation of the one or more deformable elements is predominant over deformation of the second plate member when the joint is placed in the fixed configuration.

74. The bone plate of any of paragraphs 71 to 73, wherein the one or more protrusions are formed of polymer and the first surface region is formed of metal.

75. The bone plate of any of paragraphs 71 to 73, wherein the one or more protrusions and the first surface region are each formed of metal.

76. The bone plate of any of paragraphs 70 to 75, wherein the second plate member has a body that forms the second surface region, and wherein the second plate member includes one or more deformable elements that are discrete from and attached to the body, and wherein the one or more deformable elements are deformed by contact with the one or more protrusions when the joint is placed in the fixed configuration.

77. The bone plate of paragraph 76, wherein the one or more deformable elements are recessed with respect to the second surface region and define at least a portion of each of the one or more voids.

78. The bone plate of paragraph 76, wherein the one or more protrusions and the second surface region are harder than the one or more deformable elements, such that deformation of the one or more deformable elements is predominant over deformation of the one or more protrusions and the second surface region when the joint is placed in the fixed configuration.

79. The bone plate of any of paragraphs 76 to 78, wherein the one or more protrusions and the first surface region are formed integrally with one another.

80. The bone plate of any of paragraph 70, wherein the one or more protrusions and the first surface region are formed integrally with one another.

81. The bone plate of paragraph 80, wherein the one or more protrusions and the at least one void are each deformed when the joint is placed in the fixed configuration.

82. The bone plate of any of paragraphs 70 to 75, wherein the second plate member include a same continuous surface that defines each of the one or more voids and forms the second surface region.

83. The bone plate of any of paragraphs 70 to 82, wherein the first and second surface regions are engaged with one another in the fixed configuration of the joint.

84. The bone plate of any of paragraphs 70 to 82, wherein the one or more voids have a depth, wherein the one or more protrusions have a height, and wherein the depth is at least one-fourth of the height.

85. The bone plate of paragraph 84, wherein the depth is equal to or greater than the height.

86. The bone plate of any of paragraphs 70 to 85, wherein each of the one or more protrusions has a height of at least 0.2 millimeter.

87. The bone plate of paragraph 70 to 86, wherein each of the one or more voids has a depth of at least 0.2 millimeter.

88. The bone plate of any of paragraphs 70 to 87, wherein the one or more voids form a pattern.

89. The bone plate of any of paragraphs 70 to 88, wherein the first surface region and the one or more protrusions collectively define an area, and wherein the first surface region constitutes a majority of the area, and optionally at least 70, 80, or 90% of the area.

90. The bone plate of any of paragraphs 70 to 89, wherein the second surface region is composed of a plurality of surface areas that are isolated from one another by the one or more voids.

91. The bone plate of any of paragraphs 70 to 90, wherein each protrusion extends beyond the second surface region into the second plate member in the movable configuration, and wherein each protrusion extends farther into the second plate member in the fixed configuration than in the movable configuration 92. The bone plate of any of paragraphs 70 to 91, wherein the one or more protrusions reduce or prevent contact between the first surface region and the second surface region in the movable configuration.

93. The bone plate of paragraph 70, wherein the one or more protrusions are harder than the first surface region.

94. The bone plate of any of paragraphs 70 to 93, wherein one of the plate members includes a deformable element that is deformed when the joint is placed in the fixed configuration, and wherein the deformable element is disposed inside a perimeter of the first or second surface region of the one plate member.

95. The bone plate of any of paragraphs 70 to 94, wherein the second surface region and the one or more voids collectively define an area, and wherein the one or more voids constitute a majority of the area.

96. The bone plate of any of paragraphs 70 to 95, wherein at least a portion of each protrusion enters at least one void when the joint is placed in the fixed configuration from the movable configuration.

97. The bone plate of any of paragraphs 70 to 96, wherein the one or more voids are formed by milling, sawing, sintering, photo-etching, or electrical discharge machining.

98. The bone plate of any of paragraphs 70 to 97, wherein each of the first and second surface regions defines a sphere having the same radius of curvature.

99. The bone plate of any of paragraphs 70 to 98, wherein at least one of the first and second surface regions is not continuous.

100. The bone plate of paragraph 99, wherein the at least one surface region is composed of a plurality of surface areas that are isolated from one another by the one or more protrusions or the one or more voids.

101. The bone plate of any of paragraphs 70 to 100, wherein the voids are regularly spaced.

102. The bone plate of any of paragraphs 70 to 101, wherein the voids intersect one another to form a grid.

103. A bone plate for fixing bone, comprising: (A) a first plate member and a second plate member overlapping one another at a region of overlap, each plate member defining one or more through-holes outside the region of overlap to receive one or more fasteners to attach the plate member to bone; and (B) a connector that connects the plate members to one another in the region of overlap to form a joint having (a) a movable configuration that permits changing an orientation of the plate members relative to one another in at least two nonparallel planes, and (b) a fixed configuration in which the orientation of the plate members is fixed; wherein the first plate member includes a body defining the one or more through-holes and also includes one or more discrete deformable elements disposed between the body and the second plate member in the region of overlap, and wherein each deformable element is configured to be deformed by compressive force applied to the deformable element by the body of the first plate member and the second plate member when the joint is placed in the fixed configuration.

104. The bone plate of paragraph 103, wherein the body defines one or more recesses, and wherein each deformable element is disposed in at least one of the recesses.

105. The bone plate of paragraph 104, wherein each deformable element projects from the at least one recess to form a protrusion.

106. The bone plate of any of paragraphs 103 to 105, wherein the first and second plate members have respective first and second surface regions that are complementary to and face one another in the region of overlap, and wherein each deformable element projects from the first surface region to form one of the protrusions.

107. The bone plate of any of paragraphs 103 to 106, wherein the plate members are rotatable relative to one another in the movable configuration about an axis defined by the connector.

108. The bone plate of any of paragraphs 103 to 107, wherein the connector has an external thread.

109. The bone plate of any of paragraphs 103 to 108, wherein the bone plate has an inner surface configured to contact bone, wherein the connector has a head and a shaft, and wherein the head is below the shaft when the inner surface is facing down.

110. The bone plate of paragraph 109, wherein the external thread is left-handed.

111. The bone plate of any of paragraphs 103 to 110, wherein the plate members are rotatable relative to one another in the movable configuration in a pair of planes that are orthogonal to one another.

112. The bone plate of any of paragraphs 103 to 111, wherein the first plate member and the second plate member have respective first and second surface regions that are complementary to one another, and wherein the second plate member defines one or more voids that are recessed with respect to the second surface region.

113. The bone plate of paragraph 112, wherein at least a portion of each deformable element extends into at least one of the one or more voids in the fixed configuration of the joint.

114. The bone plate of any of paragraphs 103 to 113, wherein the first plate member and the second plate member have respective first and second surface regions that are complementary to one another, and wherein the second plate member defines one or more protrusions that are raised with respect to the second surface region, and wherein each of the one or more protrusions deforms at least one of the deformable elements when the joint is placed in the fixed configuration.

115. The bone plate of paragraph 114, wherein the one or more protrusions include at least one ridge.

116. The bone plate of any of paragraphs 103 to 115, wherein each of the one or more deformable elements is formed of polymer, and wherein the body is formed of metal.

117. The bone plate of any of paragraphs 103 to 116, wherein the bone plate is configured to be attached to a distal radius.

118. The bone plate of any of paragraphs 103 to 117, wherein a length of the bone plate is adjustable when the joint is in the movable configuration.

119. A method of fixing bone, the method comprising in any order: (A) attaching the bone plate of paragraph 103 to a bone with fasteners disposed in the through-holes; (B) changing an orientation of the plate members relative to one another with the joint in the movable configuration; and (C) placing the joint in the fixed configuration.

120. The method of paragraph 119, wherein the step of changing is performed after the step of attaching, and wherein, optionally, the step of changing includes a step of applying torque to the bone plate with one or more tools that are engaged with the bone plate.

121. The method of paragraph 119 or 120, wherein the step of attaching the bone plate includes a step of attaching the bone plate to a distal portion of a radius.

122. The method of any of paragraphs 119 to 121, wherein the bone has a discontinuity, wherein the step of attaching is performed with the joint overlapping the discontinuity, and wherein, optionally, the discontinuity is a fracture.

123. A bone plate for fixing bone, comprising: (A) a first plate member and a second plate member overlapping one another at a region of overlap, each plate member defining one or more through-holes outside the region of overlap to receive one or more fasteners to attach the plate member to bone; and (B) a connector that connects the pair of plate members to one another in the region of overlap to form a joint having (i) a movable configuration that permits changing an orientation of the plate members relative to one another in at least two nonparallel planes, and (ii) a fixed configuration in which the orientation of the plate members is fixed; wherein the first and second plate members define respective first and second apertures in the region of overlap, wherein the connector extends from the first aperture to the second aperture, wherein the first plate member defines a projection that is received in the second aperture, and wherein the projection and the second aperture collectively define a range for the orientation in each of the nonparallel planes.

124. The bone plate of paragraph 123, wherein the first aperture extends through the projection.

125. The bone plate of paragraph 123 or 124, wherein the projection is centered on the first aperture.

126. The bone plate of any of paragraphs 123 to 125, wherein the connector has a head and a shaft, and wherein portions of the shaft are disposed in the first aperture and the second aperture.

127. The bone plate of any of paragraphs 123 to 126, wherein the second aperture has an internal thread for threaded engagement with an external thread of the connector.

128. The bone plate of any of paragraphs 123 to 127, wherein the first plate member has an inner or an outer surface that faces the second plate member, wherein the first aperture has a region of minimum width that prevents a head of the connector from passing through the first aperture, and wherein the first aperture widens as it extends from the region of minimum width to the inner or outer surface, to form a receiver for the projection.

129. The bone plate of paragraph 128, wherein the outer surface of the first plate member faces the second plate member, and wherein the head of the connector is disposed below the region of minimum width when the outer surface is facing up.

130. The bone plate of any of paragraphs 123 to 129, wherein the connector has a shaft with an external thread that is left-handed.

131. The bone plate of any of paragraphs 128 to 130, wherein the connector defines an axis, and wherein each of the receiver and the projection has a perimeter wall that is within 30 degrees of parallel to the axis.

132. The bone plate of any of paragraphs 123 to 131, wherein a wall of the first aperture limits rotation of the projection about an axis defined by the connector in the movable configuration of the joint.

133. The bone plate of paragraph 132, wherein the projection has a range of angular motion of less than 60, 45, or 30 degrees about the axis defined by the connector.

134. A bone plate for fixing bone, comprising: (A) a pair of plate members overlapping one another at a region of overlap, each plate member defining one or more through-holes outside the region of overlap to receive one or more fasteners to attach the plate member to bone; and (B) a connector that connects the pair of plate members to one another in the region of overlap to form a joint having (i) a movable configuration that permits changing an orientation of the plate members relative to one another continuously in a first plane and in discrete increments in a second plane that is transverse to the first plane, and (ii) a fixed configuration in which the orientation of the plate members is fixed.

135. The bone plate of paragraph 134, wherein one of the plate members includes a series of openings, and wherein the other plate member includes an edge region configured to be interchangeably received in each of the openings to provide the discrete increments by which the orientation is changed in the second plane.

136. The bone plate of paragraph 134 or 135, wherein one of the plate members includes a series of teeth, and wherein the other plate member includes an edge region configured to be interchangeably received between successive pairs of the teeth to provide the discrete increments by which the orientation is changed in the second plane.

137. The bone plate of any of paragraphs 135 or 136, wherein the edge region forms part of a perimeter of the one plate member.

138. The bone plate of any of paragraphs 135 to 137, wherein the edge region is arcuate in the first plane.

139. The bone plate of any of paragraphs 135, 137, and 138, wherein each opening is arcuate in the first plane.

140. The bone plate of any of paragraphs 134 to 139, wherein one of the plate members includes a tab that helps to define a range of motion of the plate members relative to one another in the first plane.

141. The bone plate of paragraph 140, wherein the tab is visible from above the bone plate and indicates the orientation in the first plane.

142. The bone plate of paragraph 140 or 141, wherein the tab is received in a slot defined by the other plate member, and wherein contact of the tab with a wall of the slot defines the range of motion in the first plane.

143. The bone plate of any of paragraphs 134 to 142, wherein the bone plate includes a ratchet that permits the orientation to be changed by the discrete increments.

144. A bone plate for fixing bone, comprising: (A) a first plate member forming a first joint surface defining one or more protrusions; (B) a second plate member defining one or more voids; and (C) a connector that connects the plate members to one another with the joint surfaces facing one another, to form a joint having (i) a movable configuration that permits changing an orientation of the plate members relative to one another in each of at least two nonparallel planes, and (ii) a fixed configuration in which the orientation of the plate members is fixed; wherein the one or more protrusions are configured to deform and/or be deformed by the second joint surface when the joint is placed in the fixed configuration, such that at least a portion of each protrusion enters least one of the voids.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

The invention is claimed as follows:

1. A system comprising:
   a fastener configured to be inserted into bone; and
   an adjustable bone plate including:
      a first plate member including a plurality of first openings;
      a second plate member including a plurality of second openings, wherein each of the plurality of first and second openings is configured to receive a respective fastener; and
      an elongate member permanently attached to one of the first or second plate members,
   wherein the first and second plate members are mated such that the first and second plate members may rotate relative to one another about a pivot axis extending through one of the plurality of first openings and one of the plurality of second openings,
   wherein the fastener is positioned through the first and second plate members along the pivot axis and configured to be positioned into the bone,
   wherein the first or second plate member without the permanently attached elongate member includes a slot and wherein the elongate member is positioned within the slot thereby establishing a range of rotation for the mated first and second plate members.

2. The system of claim 1, wherein the slot is non-threaded.

3. The system of claim 1, wherein a quantity of the plurality of second openings is greater than a quantity of the plurality of first openings.

4. The system of claim 1, wherein the first or second plate member includes a boss and the other of the first or second plate member includes a recess, and wherein the boss is positioned within the recess.

5. The system of claim 4, wherein each of the boss and the recess is coaxial with the pivot axis.

6. The system of claim 4, wherein the first plate member includes a first mating surface and the second plate member includes a second mating surface in contact with the first mating surface, and wherein the boss is formed on the first or second mating surface and the recess is formed in the other of the first or second mating surface.

7. The system of claim 1, wherein the one of the plurality of first openings and/or the one of the plurality of second openings is threaded.

8. The system of claim 7, wherein the fastener is disposed in threaded engagement with the one of the plurality of first openings and/or the one of the plurality of second openings.

9. The system of claim 1, wherein the first plate member and the second plate member are secured together using a connector disposed through the one of the plurality of first openings and the one of the plurality of second openings.

10. The system of claim 9, wherein the connector comprises a cannulation for receiving the fastener.

11. The system of claim 10, wherein the cannulation is non-threaded.

12. The system of claim 10, wherein the cannulation is threaded.

13. The system of claim 1, wherein the second plate member has a greater length than the first plate member.

14. The system of claim 1, wherein the first plate member includes a first track and the second plate member includes a second end region, and wherein the second end region is positioned within the first track.

15. The system of claim 14, wherein the first track has a center of curvature on the pivot axis.

16. The system of claim 14, wherein the second end region positioned within the first track prevents disassembly of the first and second plate members from one another in both directions parallel to the pivot axis.

17. The system of claim 14, wherein the first track and the second end region are each arcuate in a plane orthogonal to the pivot axis.

18. The system of claim 14, wherein the first plate member further includes a first end region and the second plate member further includes a second track, and wherein the first end region is positioned within the second track.

19. The system of claim 1, wherein the elongate member is not configured to be inserted into the bone.

20. The system of claim 1, wherein the elongate member includes a head and a shaft, wherein the shaft is non-threaded.

* * * * *